US009644016B2

(12) United States Patent
Stagliano et al.

(10) Patent No.: US 9,644,016 B2
(45) Date of Patent: May 9, 2017

(54) SOLUBLE NOTCH RECEPTOR PROPROTEINS AND METHODS OF USE THEREOF

(71) Applicant: CytomX Therapeutics, Inc., South San Francisco, CA (US)

(72) Inventors: Nancy E. Stagliano, Santa Barbara, CA (US); James W. West, San Mateo, CA (US); Kathryn Kamath, Santa Barbara, CA (US); Paul H. Bessette, Camarillo, CA (US); Jason G. Sagert, San Mateo, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 14/673,175

(22) Filed: Mar. 30, 2015

(65) Prior Publication Data
US 2015/0203559 A1 Jul. 23, 2015

Related U.S. Application Data

(63) Continuation of application No. 13/721,528, filed on Dec. 20, 2012, now Pat. No. 8,993,266, which is a continuation of application No. 12/711,199, filed on Feb. 23, 2010, now Pat. No. 8,399,219.

(60) Provisional application No. 61/154,730, filed on Feb. 23, 2009.

(51) Int. Cl.
| | |
|---|---|
| *C07K 14/71* | (2006.01) |
| *C07K 19/00* | (2006.01) |
| *A61K 38/00* | (2006.01) |
| *C07K 14/56* | (2006.01) |
| *A61K 47/48* | (2006.01) |
| *C07K 14/00* | (2006.01) |
| *C07K 14/555* | (2006.01) |
| *C07K 14/565* | (2006.01) |
| *C07K 14/57* | (2006.01) |
| *C07K 16/00* | (2006.01) |
| *G01N 33/68* | (2006.01) |

(52) U.S. Cl.
CPC ........ *C07K 14/56* (2013.01); *A61K 47/48246* (2013.01); *A61K 47/48338* (2013.01); *C07K 14/00* (2013.01); *C07K 14/555* (2013.01); *C07K 14/565* (2013.01); *C07K 14/57* (2013.01); *C07K 16/00* (2013.01); *C07K 19/00* (2013.01); *G01N 33/6866* (2013.01); *A61K 38/00* (2013.01); *C07K 2319/31* (2013.01); *C07K 2319/33* (2013.01); *C07K 2319/50* (2013.01); *C07K 2319/70* (2013.01); *C07K 2319/90* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,379,145 | A | 4/1983 | Masuho et al. |
| 4,671,958 | A | 6/1987 | Rodwell et al. |
| 4,816,567 | A | 3/1989 | Cabilly et al. |
| 4,867,973 | A | 9/1989 | Goers et al. |
| 4,952,394 | A | 8/1990 | Senter |
| 4,975,278 | A | 12/1990 | Senter et al. |
| 5,010,176 | A | 4/1991 | Barton |
| 5,144,012 | A | 9/1992 | Johnson et al. |
| 5,162,218 | A | 11/1992 | Schultz |
| 5,223,409 | A | 6/1993 | Ladner et al. |
| 5,272,253 | A | 12/1993 | Koppel et al. |
| 5,306,731 | A | 4/1994 | Epstein |
| 5,403,484 | A | 4/1995 | Ladner et al. |

(Continued)

FOREIGN PATENT DOCUMENTS

| | | |
|---|---|---|
| EP | 0 329 185 B1 | 4/1994 |
| EP | 0 444 158 B1 | 1/1996 |

(Continued)

OTHER PUBLICATIONS

Zhou et al., Proteolytic processing in the secretory pathway. J Biol. Chem. 274, 20745-20748, 1999.*

(Continued)

*Primary Examiner* — Elly-Gerald Stoica

(74) *Attorney, Agent, or Firm* — Cooley LLP; Ivor R. Elrifi

(57) ABSTRACT

The present disclosure provides for proprotein and activatable proprotein compositions. A proprotein contains a functional protein (i.e. a full length protein or functional fragment thereof) which is coupled to a peptide mask that inhibits the binding of the functional protein to its target or binding partner. An activatable proprotein contains a functional protein coupled to a peptide mask, and further coupled to an activatable linker, wherein in an non-activated state, the peptide mask inhibits binding of the functional protein to its target or binding partner and in an activated state the peptide mask does not inhibit binding of the functional protein to its target or binding partner. Proproteins can provide for reduced toxicity and adverse side effects that could otherwise result from binding of a functional protein at non-treatment sites if it were not inhibited from binding its binding partner. Proproteins can further provide improved biodistribution characteristics. Proproteins containing a peptide mask can display a longer in vivo or serum half-life than the corresponding functional protein not containing a peptide mask. The disclosure further provides methods of screening for, making, and using these proproteins.

28 Claims, 3 Drawing Sheets

(56) References Cited

U.S. PATENT DOCUMENTS

| | | |
|---|---|---|
| 5,468,785 A | 11/1995 | Greuel et al. |
| 5,571,698 A | 11/1996 | Ladner et al. |
| 5,637,288 A | 6/1997 | Goldenberg et al. |
| 5,665,358 A | 9/1997 | Barton et al. |
| 5,679,548 A | 10/1997 | Barbas et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,834,247 A | 11/1998 | Comb et al. |
| 5,837,500 A | 11/1998 | Ladner et al. |
| 5,866,341 A | 2/1999 | Spinella et al. |
| 5,922,845 A | 7/1999 | Deo et al. |
| 5,985,626 A | 11/1999 | Barbas et al. |
| 5,990,286 A | 11/1999 | Khawli et al. |
| 6,015,557 A | 1/2000 | Tobinick et al. |
| 6,054,297 A | 4/2000 | Carter et al. |
| 6,066,719 A | 5/2000 | Zapata |
| 6,107,059 A | 8/2000 | Hart |
| 6,165,464 A | 12/2000 | Hudziak et al. |
| 6,217,866 B1 | 4/2001 | Schlessinger et al. |
| 6,235,883 B1 | 5/2001 | Jakobovits et al. |
| 6,258,562 B1 | 7/2001 | Salfeld et al. |
| 6,265,540 B1 | 7/2001 | Isaacs et al. |
| 6,268,488 B1 | 7/2001 | Barbas et al. |
| 6,342,221 B1 | 1/2002 | Thorpe et al. |
| 6,399,063 B1 | 6/2002 | Hudziak et al. |
| 6,407,213 B1 | 6/2002 | Carter et al. |
| 6,534,061 B1 | 3/2003 | Goddard et al. |
| 6,548,249 B1 | 4/2003 | Anderson et al. |
| 6,682,736 B1 | 1/2004 | Hanson et al. |
| 6,884,879 B1 | 4/2005 | Baca et al. |
| 6,903,196 B1 | 6/2005 | Roben et al. |
| 6,955,900 B1 | 10/2005 | Barbas et al. |
| 6,979,538 B2 | 12/2005 | Ladner et al. |
| 6,984,720 B1 | 1/2006 | Korman et al. |
| 6,992,174 B2 | 1/2006 | Gillies et al. |
| 7,029,874 B2 | 4/2006 | Baker et al. |
| 7,060,269 B1 | 6/2006 | Baca et al. |
| 7,060,808 B1 | 6/2006 | Goldstein et al. |
| 7,087,409 B2 | 8/2006 | Barbas et al. |
| 7,098,002 B1 | 8/2006 | Rubinstein et al. |
| 7,118,879 B2 | 10/2006 | Ladner et al. |
| 7,157,418 B1 | 1/2007 | McDonald et al. |
| 7,169,901 B2 | 1/2007 | Baca et al. |
| 7,208,293 B2 | 4/2007 | Ladner et al. |
| 7,226,596 B2 | 6/2007 | Bodary et al. |
| 7,256,038 B2 | 8/2007 | Daugherty et al. |
| 7,297,334 B2 | 11/2007 | Baca et al. |
| 7,304,143 B2 | 12/2007 | Goddard et al. |
| 7,341,720 B2 | 3/2008 | Stefano |
| 7,365,166 B2 | 4/2008 | Baca et al. |
| 7,375,193 B2 | 5/2008 | Baca et al. |
| 7,452,535 B2 | 11/2008 | Davis et al. |
| 7,465,790 B2 | 12/2008 | Waldmann et al. |
| 7,608,591 B2 | 10/2009 | Liu et al. |
| 2002/0048578 A1 | 4/2002 | Waldmann et al. |
| 2003/0021791 A1 | 1/2003 | Kassis et al. |
| 2003/0134824 A1 | 7/2003 | Breslow et al. |
| 2003/0219402 A1 | 11/2003 | Rutter |
| 2004/0014652 A1 | 1/2004 | Trouet et al. |
| 2004/0053829 A1 | 3/2004 | Pfizenmaier et al. |
| 2004/0082039 A1 | 4/2004 | Gillies et al. |
| 2004/0146516 A1 | 7/2004 | Roben et al. |
| 2004/0147444 A1 | 7/2004 | Chemajovsky et al. |
| 2004/0185053 A1 | 9/2004 | Govindan |
| 2004/0213797 A1 | 10/2004 | Bodmer et al. |
| 2004/0265274 A1 | 12/2004 | Wei et al. |
| 2005/0025751 A1 | 2/2005 | Bodmer et al. |
| 2005/0042680 A1 | 2/2005 | Filpula et al. |
| 2005/0106100 A1 | 5/2005 | Harris et al. |
| 2005/0136049 A1 | 6/2005 | Ledbetter et al. |
| 2005/0196754 A1 | 9/2005 | Drmanac et al. |
| 2005/0208558 A1 | 9/2005 | Venter et al. |
| 2005/0255042 A1 | 11/2005 | Lam et al. |
| 2005/0255555 A1 | 11/2005 | Johns et al. |
| 2005/0277160 A1 | 12/2005 | Shiba et al. |
| 2005/0287155 A1 | 12/2005 | Santi et al. |
| 2006/0018911 A1 | 1/2006 | Ault-Riche et al. |
| 2006/0078901 A1 | 4/2006 | Buchrieser et al. |
| 2006/0121570 A1 | 6/2006 | Barbas et al. |
| 2006/0228348 A1 | 10/2006 | Stefano |
| 2006/0246066 A1 | 11/2006 | Morgan et al. |
| 2006/0252130 A1 | 11/2006 | Boehm et al. |
| 2006/0265274 A1 | 11/2006 | Commins et al. |
| 2007/0041904 A1 | 2/2007 | Jiang et al. |
| 2007/0061916 A1 | 3/2007 | Kovalic et al. |
| 2007/0065158 A1 | 3/2007 | Shindou et al. |
| 2007/0065878 A1 | 3/2007 | Daugherty et al. |
| 2007/0083334 A1 | 4/2007 | Mintz et al. |
| 2008/0107660 A1 | 5/2008 | Self |
| 2009/0023602 A1 | 1/2009 | Fellouse et al. |
| 2009/0123467 A1 | 5/2009 | Bedi et al. |
| 2009/0304719 A1 | 12/2009 | Daugherty et al. |
| 2010/0189651 A1 | 7/2010 | Stagliano et al. |

FOREIGN PATENT DOCUMENTS

| | | |
|---|---|---|
| EP | 0 623 679 B1 | 6/2003 |
| EP | 1 550 729 B1 | 7/2005 |
| EP | 1 579 873 A1 | 9/2005 |
| EP | 1 770 099 A1 | 4/2007 |
| WO | WO 95/11703 A1 | 5/1995 |
| WO | WO 96/05863 A1 | 2/1996 |
| WO | WO 96/34892 A1 | 11/1996 |
| WO | WO 97/31024 A1 | 8/1997 |
| WO | WO 00/04192 A1 | 1/2000 |
| WO | WO 00/18962 A1 | 4/2000 |
| WO | WO 00/23472 A2 | 4/2000 |
| WO | WO 00/34519 A1 | 6/2000 |
| WO | WO 02/30460 A2 | 4/2002 |
| WO | WO 02/060488 A1 | 8/2002 |
| WO | WO 02/066058 A1 | 8/2002 |
| WO | WO 02/066656 A2 | 8/2002 |
| WO | WO 03/012105 A2 | 2/2003 |
| WO | WO 03/020212 A2 | 3/2003 |
| WO | WO 2004/009638 A1 | 1/2004 |
| WO | WO 2005/007198 A2 | 1/2005 |
| WO | WO 2005/042034 A1 | 5/2005 |
| WO | WO 2005/051315 A2 | 6/2005 |
| WO | WO 2006/090813 A1 | 8/2006 |
| WO | WO 2007/014744 A2 | 2/2007 |
| WO | WO 2007/026972 A2 | 3/2007 |
| WO | WO 2007/027935 A2 | 3/2007 |
| WO | WO 2007/066106 A1 | 6/2007 |
| WO | WO 2007/066106 A2 | 6/2007 |
| WO | WO 2007/099348 A2 | 9/2007 |
| WO | WO 2007/105027 A1 | 9/2007 |
| WO | WO 2007/106415 A2 | 9/2007 |
| WO | WO 2007/109254 A2 | 9/2007 |
| WO | WO 2008/011603 A2 | 1/2008 |
| WO | WO 2008/048680 A2 | 4/2008 |
| WO | WO 2009/018500 A1 | 2/2009 |
| WO | WO 2009/025846 A2 | 2/2009 |
| WO | WO 2009/026274 A1 | 2/2009 |
| WO | WO 2009/039409 A1 | 3/2009 |
| WO | WO 2009/088805 A2 | 7/2009 |
| WO | WO 2010/077643 A1 | 7/2010 |

OTHER PUBLICATIONS

Hook et al., Proteases for processing proneuropeptides into peptide neurotransmitters and hormones. Annual Rev. Pharmacol. Toxicol. 48, 393-423, 2008).*

Chrétien et al., Proprotein convertases as therapeutic agents, Exp. Op. Therap. Targ., 12, 1289-1300, 2008).*

Black et al., Generation of biologically active Interleukin-1β by proteolytic cleavage of the inactive precursor. J Biol. Chem. 263, 9437-9442, 1988.*

Hailey et al., Pro-interleukin (IL)-1β shares a core region of stability as compared with mature IL-1β while maintaining a distinctly different configuration landscape. J Biol. Chem. 284, 26137-26148, 2009.*

(56) References Cited

OTHER PUBLICATIONS

Parry et al., Molecular mechanism of plasminogen activation: bacterial cofactors provide clues. Trends Biol. Sci. 25, 53-59, 2000.*
Anderson et at. "Selective photothermolysis: precise microsurgery by selective absorption of pulsed radiation", Science, 1983; 220(4596):524-7.
Armentano et al. "Induction of covalent binding antibodies", Immunol Lett. Feb. 28, 2006; 103(1):51-7.
Baron, Narula, From Cloning to a Commercial Realization: Human Alpha Interferon, Critical Review in Biotechnology. 1990; 1 0(3): 179-190.
Bartenschlager et al. "Substrate determinants for cleavage in cis and in trans by the hepatitis C virus N53 proteinase", J Virol. 1995. 69(1): 198-205.
Bessette et al. "Construction of designed protein libraries using gene assembly mutagenesis", Methods Mol Biol., 2003; 231:29-37.
Bessette et al. "Rapid isolation of high-affinity protein binding peptides using bacterial display", Protein Eng Des Sel, Oct. 17, 2004(10):731-9.
Bessette, U.S. Appl. No. 61/249,416, entitled "Activatable Antibody Complexes," filed Oct. 7, 2009.
Boder et al. "Yeast surface display for screening combinatorial polypeptide Libraries", Nat Biotechnol. 1997; 15(6):553-7.
Boder et al. Directed evolution of antibody fragments with monovalent femtomolar antigen-binding affinity. Proc Natl Acad Sci U S A. 2000; 97(20): 10701-5.
Bupp et al. "Altering retroviral tropism using a random-display envelope library", Mol Ther. 2002; 5(3):329-35.
Caliceti et al. "Preparation and properties of monomethoxy poly(ethyleneglycol) doxorubicin conjugates linked by an amino acid or a peptide as spacer", Farmaco 1993; 48(7):919-32.
Caron et al. "Murine and humanized constructs of monoclonal antibody M 195 (anti-CD33) for the therapy of acute myelogenous leukemia", Cancer, Feb. 1, 1994; 73(3 Suppl): 1049-56.
Chang et al., "Intratumoral delivery of IL-18 naked DNA induces T-cell activation and Th1 response in a mouse hepatic cancer model", BMC Cancer, 2007; 87(7): 1-6.
Chari et al. "C242-DM 1: A tumor-activated prodrug that shows exceptional activity in human colon tumor xenograft models at non-toxic doses", Proceedings of the American Association for Cancer Research Annual Meeting, Mar. 1998, 39:643 (89th annual meeting.
Chari et al. "Integration of SB-40875 into combination treatments of human colon xenograft models of SCID mice", Proceedings of the American Association for Cancer Research Annual Meeting, Mar. 2000, 41 :291 (91 st annual meeting of the American Association).
Chari, "Targeted Cancer Therapy: Conferring Specificity to Cytotoxic Drugs", Accounts of Chemical Research, Jan. 2008; 41 (1):98-107.
Chari, "Targeted delivery of chemotherapeutics: Tumor-activated prodrug Therapy", Advanced Drug Delivery Reviews, Apr. 6, 1998; 31(1-2):89-104.
Chen et al. "Selection and analysis of an optimized anti-VEGF antibody: crystal structure of an affinity-matured fab in complex with antigen", J Mol Biol, Nov. 5, 1999; 293( 4 ): 865-881.
Chmura et al. "Antibodies with infinite affinity", Proc Natl Acad Sci USA. 2001; 98(15):8480-4.
Cho et al. "N-terminal processing is essential for release of epithin, a mouse type II membrane serine protease", J Biol Chem. 2001. 276(48):44581-9.
Co et al. "Chimeric and humanized antibodies with specificity for the CD33 Antigen", J Immunol, Feb. 15, 1992; 148(4):1149-54.
Cooper et al. "Galactose oxidase from Polyporus circinatus", Fr. J Biol Chem. Mar. 1959; 234(3):445-8.
Daugherty et al. "Quantitative analysis of the effect of the mutation frequency on the affinity maturation of single chain Fv antibodies", Proc Natl Acad Sci USA, Feb. 29, 2000; 97(5):2029-34.

Daugherty et at. "Flow cytometric screening of cell-based libraries", J Immunol Methods, Sep. 21, 2000; 243(1-2):211-27.
Daugherty, et al., U.S. Appl. No. 60/957,449, entitled "Activatable Binding Polypeptides and Methods of Identification and Use Thereof," filed Aug. 22, 2007.
Daugherty, et al., U.S. Appl. No. 60/957,453, entitled "Activatable Binding Polypeptides Capable of Binding Multiple Targets and Methods of Identification and Use Thereof," filed Aug. 22, 2007.
Daugherty, U.S. Appl. No. 61/052,986, entitled "Protease Activated Probody Constructs and Methods of Use," filed 05113/2008.
Doerks et al., "Protein annotation: detective work for function prediction", Trends in Genetics, vol. 14, No. 6, p. 248-250, 1998.
Donaldson et al. "Design and development of masked therapeutic antibodies to limit off-target effects—Application to anti-EGFR antibodies", Cancer Biology & Therapy, Nov. 2009, 8(22):1-6.
Facchiano et al. "Identification of a novel domain of fibroblast growth factor 2 controlling its angiogenic properties", The Journal of Biological Chemistry, 2003, 278(10):8751-8760.
Ford et al. "Fusion tails for the recovery and purification of recombinant Proteins", Protein expression and purification, 1991, 2:95-107.
Fricker, "MMP-8: a new target for atherosclerosis?" Drug Discov Today, Jan. 15, 2002; 7(2):86-8.
Funahashi et al. "A notch 1 ectodomain construct inhibits endothelial notch signaling, tumor growth, and angiogenesis", Cancer Res. 2008, 68(12):4727-35.
Georgiou "Analysis of large libraries of protein mutants using flow cytometry", Adv Protein Chem, 2000; 55:293-315.
Georgiou et al. "Display of heterologous proteins on the surface of microorganisms: from the screening of combinatorial libraries to live recombinant vaccines", Nat Biotechnol. Jan. 1997; 15(1):29-34.
Gerspach et al. "Restoration of membrane TNF-like activity by cell surface targeting and matrix metalloproteinase-mediated processing of a TNF prodrug", Cell Death and Differentiation, 2006, 13:273-284.
Gilliland et al. "Elimination of the Immunogenicity of Therapeutic Antibodies", Journal of Immunology, 1999, 162:3663-3671.
Gilliland et al. "Rapid and reliable cloning of antibody variable regions and generation of recombinant single chain antibody fragments", Tissue Antigens, Jan. 1996; 47(1):1-20.
Grussenmeyer et al. "Complexes of polyoma virus medium T antigen and cellular proteins", Proc Natl Acad Sci USA, Dec. 1985; 82(23):7952-4.
Guay et al. "Potency and selectivity of inhibition of cathepsin K, L and S by their respective propeptides", Eur J Biochem., 2000, 267(20):6311-8.
Hagedorn et al., "A short peptide domain of platelet factor 4 blocks angiogenic key events induced by FGF-2" FASEB J. Mar. 15, 2001(3):550-2.
Hale, "Synthetic peptide mimotope of the CAMPATH-1 (CD52) antigen, a small glycosylphosphatidylinositol-anchored glycoprotein", Immunotechnology, Dec. 1995; 1(3):175-187.
Harris et al. "Generation of Anti-complement 'Prodrugs'" The Journal of Biological Chemistry, Sep. 2003, 278(38):36068-36076.
Hillmen et al., "The complement inhibitor eculizumab in paroxysmal nocturnal Hemoglobinuria", N Engl J Med. Sep. 21, 2006; 355(12):1233-43.
Hopp et al. "A Short Polypeptide Marker Sequence Useful for Recombinant Protein Identification and Purification", Nature Biotechnology 1988 6: 1204-1210.
Horton et al. "Engineering hybrid genes without the use of restriction enzymes: gene splicing by overlap extension" Gene, Apr. 15, 1989; 77(1):61-8.
Iiyama et al. "Patterns of Vascular Cell Adhesion Molecule-1 and Intercellular Adhesion Molecule-1 Expression in Rabbit and Mouse Atherosclerotic Lesions and at Sites Predisposed to Lesion Formation", Circulation Research, Am Heart Assoc.1999; 85: 199-207.
Immordino et al. "Stealth liposomes: review of the basic science, rationale, and clinical applications, existing and potential", Int J Nanomedicine, Sep. 2006; 1(3):297-315.
International Search report dated Nov. 13, 2007 for PCT application PCT/US2006/34096.

(56) References Cited

OTHER PUBLICATIONS

International Search report dated Nov. 5, 2010 for PCT application PCT/US2010/025121.
International Search report dated Sep. 14, 2010 for PCT application PCT/US2010/020820.
Isaacs et al. "Helplessness as a Strategy for Avoiding Antiglobulin responses to Therapeutic Monoclonal Antibodies", Therapeutic Immunology, Dec. 1994; 1(6):303-312.
Jensen-Jarolim et al. "Peptide mimotopes displayed by phage inhibit antibody binding to bet v 1, the major birch pollen allergen, and induce specific IgG response in mice", FASEB J. Dec. 1998; 12(15):1635-42.
Johnson et al. "Development of a humanized monoclonal antibody (MEDI-493) with potent in vitro and in vivo activity against respiratory syncytial virus", J Infect Dis, Nov. 1997; 176(5): 1215-24.
Kam et al. "MUC1 synthetic peptide inhibition of intercellular adhesion molecule-1 and MUC1 binding requires six tandem repeats", Cancer Res. 1998, 58(23):5577-81.
Kamath, et al., U.S. Appl. No. 61/249,441, entitled "Methods and Compositions for Serum Half-Life Extension of Antibodies and Antibody Derivatives," filed Oct. 7, 2009.
Karush et al. "Interaction of a bivalent ligand with IgM anti-lactose antibody", Biochemistry, May 29, 1979; 18(11):2226-32.
Knight et al. "Construction and initial characterization of a mouse-human chimeric anti-TNF antibody", Mol Immunol. Nov. 1993; 30(16): 1443-53.
La Rocca et al. "Zymographic detection and clinical correlations of MMP-2 and MMP-9 in breast cancer sera", Br J Cancer. Apr. 5, 2004; 90(7):1414-21.
Lambert et al. "Pharmacokinetics, in vivo stability, and toxicity of the tumor activated prodrug", Proceedings of the American Association for Cancer Research Annual Meeting, Mar. 1998, 39:522 (89th annual meeting of the American Association for Cancer Research).
Lamoyi et al. "Preparation of F(ab')2 fragments from mouse IgG of various Subclasses", J Immunol Methods, Jan. 28, 1983; 56(2):235-43.
Leger et al. Humanization of a mouse antibody against human alpha-4 integrin: a potential therapeutic for the treatment of multiple sclerosis. Hum Antibodies, 1997; 8(1):3-16.
Li et al., "Self-masking in an intact ERM-merlin protein: an active role for the central alpha-helical domain", J. Mol. Biol., vol. 365, p. 1446-1459, 2007.
Liu et al. "Overexpression of legumain in tumors is significant for invasion/metastasis and a candidate enzymatic target for prodrug therapy", Cancer Res. Jun. 1, 2003; 63(11):2957-64.
Lowman et al. "Selecting high-affinity binding proteins by monovalent phage Display", Biochemistry, Nov. 12, 1991; 30(45):10832-8.
Lozano et al. "Solution structure and interaction with basic and acidic fibroblast growth factor of a 3-kDa human platelet factor-4 fragment with anti-angiogenic activity", The Journal of Biological Chemistry, 2001, 276(38):35723-35734.
Mathieu et al., "Substrate specificity of schistosome versus human legumain determined by PI-P3 peptide libraries", Mol Biochem Parasitol, Apr. 30, 2002; 121(1):99-1 05.
Mattheakis et al. An in vitro polysome display system for identifying ligands from very large peptide libraries. Proc Natl Acad Sci U S A. Sep. 13, 1994; 91 ( 19):9022-6.
Mitra et al. "Reagents for the crosslinking of proteins by equilibrium transfer Alkylation", J. Am. Chem. Soc., 1979; 101(11):3097-3110.
Muller et al. "Random peptide libraries displayed on adeno-associated virus to select for targeted gene therapy vectors", Nat Biotechnol. Sep. 2003; 21(9): 1040-6. Epub Aug. 3, 2003.
Nagahira et al. "Humanization of a mouse neutralizing monoclonal antibody Against tumor necrosis factor-alpha (TNF-alpha)", J Immunol Methods. Jan. 1, 1999; 222(1-2):83-92.
Ngo et al., "Computational Complexity, Protein Structure Prediction, and the Levinthal Paradox", The Protein Folding Problem and Tertiary Structure Prediction, p. 492-495, 1994.
Nicaise et al. "Affinity transfer by CDR grafting on a non-immunoglobulin scaffold", Protein Sci. 2004, 13(7): 1882-91.
Nicolaisen-Strouss et al. "Natural feline leukemia virus variant escapes neutralization by a monoclonal antibody via an amino acid change outside the antibody-binding epitope" Journal of Virology, 1987, 61(11):3410-3415.
Nilsson et al. "Expression and purification of recombinant insulin-like growth factors from *Escherichia coli*", Methods Enzymol, 1991; 198:3-16.
Nilsson et al. "Immobilization and purification of enzymes with *staphylococcal* protein A gene fusion vectors", EMBO J. Apr. 1985; 4(4):1075-80.
Olsen et al. "High-throughput FACS method for directed evolution of substrate Specificity", Methods Mol Biol. 2003; 230:329-42.
Palandoken et al. "Amiloride peptide conjugates: prodrugs for sodium-proton exchange inhibition", J. Pharmacol. Exp: Ther, Mar. 2005, 312(3):961-967.
Parham, "On the fragmentation of monoclonal IgG 1, IgG2a, and IgG2b from BALB/c mice", J Immunol. Dec. 1983; 131(6):2895-902.
Presta et al. "Humanization of an anti-vascular endothelial growth factor monoclonal antibody for the therapy of solid tumors and other disorders", Cancer Res. Oct. 15, 1997; 57(20):4593-9.
Putnam et al. "Complete amino acid sequence of the Mu heavy chain of a human IgM immunoglobulin", Science, Oct. 19, 1973; 182(1 09):287-91.
Rader et al. "Chemically programmed monoclonal antibodies for cancer therapy: adaptor immunotherapy based on a covalent antibody catalyst", Proc Natl Acad Sci U S A, Apr. 29, 2003; 100(9):5396-400.
Ribas et al. "Tremelimumab (CP-675,206), a Cytotoxic T Lymphocyte-Associated Antigen 4 Blocking Monoclonal Antibody in Clinical Development for Patients with Cancer", Oncologist, Jul. 2007; 12:873-883.
Rice et al. Bacterial display using circularly permuted outer membrane protein OmpX yields high affinity peptide ligands. Protein Sci. Apr. 2006; 15(4):825-36.
Rodwell et al. "Linker Technology: Antibody-Mediated Delivery Systems", Biotechnology, 1985. 3:889-894.
Samel et al. "Generation of a FasL-based Proapoptotic Fusion Protein Devoid of Systemic Toxicity due to Cell-surface Antigen-restricted Activation", The Journal of Biological Chemistry, Aug. 2003, 278(34):32077-32082.
Scheraga "Predicting three-dimensional structures of oligopeptides, In: Reviews in Computational Chemistry", vol. III, Lipkowitz and Boyd, eds., New York; 1992:73-142.
Scott et al. "Searching for peptide ligands with an epitope library", Science, Jul. 27, 1990; 249(4967):386-90.
Self et al. "Light-Directed Activation of Human T-Cells", Chem Med Chem, 2007; 2:1587-1590.
Self T., "Light activatable antibodies: Models for remotely activatable Proteins", Nature Medicine, Jul. 1996, 2(7):817-820.
Self, T., "How specific are therapeutic monoclonal antibodies?" www.thelancet.com. Apr. 2006 367(960):1038-1039.
Shusta et al. "Biosynthetic polypeptide libraries. Curr Opin Biotechnol", Apr. 1999; 1 0(2): 117-22.
Sidhu et al. "Exploring protein-protein interactions with phage display" Chembiochem, 2003, 4(1): 14-25.
Skolnick et al., "From genes to protein structure and function: novel applications of computational approaches in the genomic era", Trends in Biotech, vol. 18, No. 1, p. 34-39, 2000.
Smith et al. "Protein loop grafting to construct a variant of tissue-type plasminogen activator that binds platelet integrin alpha lib beta 3", J Biol Chem. 1995, 270(51):30486-90.
Smith et al. "Single-step purification of polypeptides expressed in *Escherichia coli* as fusions with glutathione S-transferase", Gene, Jul. 15, 1988; 67(1):31-40.
Stagliano, et al. U.S. Appl. No. 61/144,105, entitled "Activatable Antibodies and Methods of Identification and Use Thereof," filed 01112/2009.

(56) References Cited

OTHER PUBLICATIONS

Stagliano, et al. U.S. Appl. No. 611144,110, entitled "Activatable Antibody Conjugates and Methods of Identification and Use Thereof," filed 01112/2009.

Stagliano, et al. U.S. Appl. No. 611154,730, entitled "Proproteins and Methods of Use Thereof," filed Feb. 23, 2009.

Stanworth, et al. "Handbook of experimental immunology", vol. 1, 2nd ed., Weir ed., chapter 10, Blackwell Scientific Publications, London; 1973.

Takagi et al., "A new approach for alteration of protease functions: pro-sequence engineering", Appl. Microbiol. Biotechnol., vol. 63, p. 1-9, 2003.

Thompson et al. "A simple procedure for the photoregulation of chymotrypsin Activity", Photochemical & Photobiological Sciences, 2006, 5:326-330.

Thompson et al. "Light Activation of Anti-CD3 in vivo Reduces the Growth of an Aggressive Ovarian Carcinoma", Chem Med Chem, 2007, 2:1591-1593.

Thompson et al. "Photocleavable Nitrobenzyl-Protein Conjugates", Biochemical and Biophysical Research Communications, Jun. 1994, 201(3):1213-1219.

Thompson et al. "The construction and in vitro testing of photoactivatable cancer targeting folated anti-CD3 conjugates", Biochemical and Biophysical Research Communication, 2008, 366:526-531.

Thompson et al. "The Construction of a Functional Photoactivatable Cancer Targeting Bispecific Antibody Conjugate", Chem Med Chem, 2007, 2:1162-1164.

Thompson, et al. "The modulation of Protein A-IgG(Fc) binding by the reversible addition of 2-nitrobenzyl groups", Biochemical Society Transactions, May 1995; vol. 23(2):1555.

Trouet et al. "CPI-0004Na: An extracellular tumor-activated prodrug of Doxorubicin", Proceedings of the American Association for Cancer Research Annual Meeting, Mar. 2000, 41:522 (91 st annual meeting of the American Association for Cancer Research, San Francisco).

Trouet et al. "Extracellularly tumor-activated prodrugs for the selective chemotherapy of cancer: application to doxorubicin and preliminary in vitro and in vivo studies", Cancer Research Apr. 2001, 61(7):2843-6.

Tsuji et al., "Molecular cloning of the large subunit of transforming growth factor type 13 masking protein and expression of the mRNA in various rat tissues", PNAS Sci. USA, vol. 87, p. 8835-8839, 1990.

Tuve et al. "Combination of tumor site-located CTL-associated antigen-4 blockade and systemic regulatory T-cell depletion induces tumor-destructive immune responses", Cancer Res. Jun. 15, 2007; 67(12):5929-39.

Vartak, G., "Matrix metalloproteases: Underutilized targets for drug delivery", Journal of Drug Targeting Jan. 2007, 15(1):1-20.

Weisel, M., "The Structure and Function of the αC Domains of Fibrinogen", Annals New York Academy of Sciences, 2001, 312-327.

Wells, "Additivity of Mutational Effects in Proteins", Biochemistry, vol. 29, No. 7, p. 8509-8517, 1990.

Werther et al. "Humanization of an anti-lymphocyte function-associated antigen (LF A)-1 monoclonal antibody and reengineering of the humanized antibody for binding to rhesus LFA-1. J Immunol", Dec. 1, 1996; 157(11):4986-95.

Wiebe et al. "Concepts for the design of anti-HIV nucleoside prodrugs for treating cephalic HIV infection", Advanced Drug Delivery Reviews Oct. 18, 1999; 39(1-3):63-80.

Wilson et al., "The use of mRNA display to select high-affinity protein-binding Peptides", Proc Natl Acad Sci US A. Mar. 27, 2001; 98(7):3750-5. Epub Mar. 13, 2001.

Wuest et al. "TNF-Selectokine: a novel prodrug generated for tumor targeting and site-specific activation of tumor necrosis factor", Oncogene, 2002, 21:4257-4265.

Xie et al. "Identification of the fibroblast growth factor (FGF)-interacting domain in a secreted FGF-binding protein by phage display", The Journal of Biological Chemistry, 2006, 281(2):1137-1144.

Yang et al. "Ipilimumab (anti-CTLA4 antibody) causes regression of metastatic renal cell cancer associated with enteritis and hypophysitis", J Jmmunother, Nov.-Dec. 2007; 30(8):825-30.

Zhou et at. "Specific Antibodies to the External Vestibule of Voltage-gated Potassium Channels Block Current", J. Gen. Physiol. 1998. 111:555-563.

* cited by examiner

US 9,644,016 B2

SOLUBLE NOTCH RECEPTOR PROPROTEINS AND METHODS OF USE THEREOF

CROSS-REFERENCE

This application is a continuation of U.S. patent application Ser. No. 13/721,528, filed Dec. 20, 2012 and issued as U.S. Pat. No. 8,993,266, which is a continuation of U.S. patent application Ser. No. 12/711,199, filed Feb. 23, 2010 and issued as U.S. Pat. No. 8,399,219, which claims the benefit of U.S. Provisional Application No. 61/154,730, filed Feb. 23, 2009, each of which application is incorporated herein by reference in its entirety.

INCORPORATION-BY-REFERENCE OF SEQUENCE LISTING

The contents of the text file named "CYTM015C02US_ST25.txt," which was created on Jun. 16, 2015 and is 31.6 KB in size, are hereby incorporated by reference in their entirety.

BACKGROUND OF THE INVENTION

Protein-based therapies have changed the face of medicine, finding application in a variety of different diseases. As with any therapies, however, the need and desire for improved specificity and selectivity for targets is of great interest.

In the realm of small molecule drugs, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects. Drugs used to target hypoxic cancer cells, through the use of redox-activation, utilize the large quantities of reductase enzyme present in the hypoxic cell to convert the drug into its cytotoxic form, essentially activating it. Since the prodrug has low cytotoxicity prior to this activation, there is a markedly decreased risk of damage to non-cancerous cells, thereby providing for reduced side-effects associated with the drug. There is a need in the field for a strategy for providing features of a prodrug to protein-based therapeutics, especially in developing second generation of protein drugs having known targets to which they bind. Increased targeting to the disease site could reduce systemic mechanism-based toxicities and lead to broader therapeutic utility.

SUMMARY OF THE INVENTION

The present disclosure provides for proprotein and activatable proprotein compositions.

In one aspect the present disclosure provides for a composition comprising a functional protein that is not an antibody or an antibody fragment, wherein the functional protein is coupled to a peptide mask that: (i) inhibits binding of the functional protein to its binding partner and (ii) does not have an amino acid sequence of the binding partner. In one embodiment, the functional protein is further coupled to a cleavable linker capable of being cleaved, such that: (i) in an uncleaved state, the peptide mask inhibits binding of the functional protein to its binding partner and (ii) in a cleaved state, the peptide mask does not inhibit binding of the functional protein to its binding partner. In one embodiment, the cleavable linker is capable of being specifically cleaved by an enzyme, capable of being reduced by a reducing agent, or capable of being photolysed. In one embodiment, the cleavable linker is capable of being specifically cleaved by an enzyme at a rate of at least $5 \times 10^4$ $M^{-1}$ S.

In another embodiment, the peptide mask is recombinantly expressed. In one embodiment, the peptide mask is unique for the functional protein.

In another embodiment, the peptide mask has a therapeutic effect once uncoupled from the functional protein.

In one embodiment, the peptide mask is 8-15 amino acids in length.

In one embodiment, the peptide mask has less than 50% amino acid sequence homology to its binding partner.

In one embodiment, the peptide mask contains less than 50% genetically non-encoded amino acids. In a related embodiment, the genetically non-encoded amino acids are D-amino acids, β-amino acids, or γ-amino acids.

In one embodiment the functional protein is a full-length protein, a functional fragment of a full-length protein, a globular protein, a fibrous protein, or a multimeric protein. In a specific embodiment, the functional protein is a ligand. In a related embodiment, the ligand is an interferon protein and is selected from the group consisting of interferon type I, interferon type II, and interferon type III or is selected from the group consisting of IFN-α, IFN-β, IFN-ω and IFN-γ. In a specific embodiment, the interferon protein is IFN-α. In a specific embodiment, the IFN-α protein is selected from the group consisting of 2a, 2b, and con1. In a related embodiment, the binding partner is a receptor for the interferon protein. In such an embodiment, the receptor for the interferon protein is selected from the group consisting of IFNAR, IFNAR1, IFNAR2, IFNGR, and IFNLR1. In a related embodiment, the peptide mask contains a sequence selected from those presented in Table 3 or a sequence at least having 90% homology thereof. In a specific embodiment, the peptide mask contains the consensus sequence TDVDYYREWXXXXXXXX (SEQ ID NO: 1).

In another embodiment, the functional protein is a soluble membrane protein or a functional fragment thereof. In another embodiment, the functional protein is a soluble receptor or fragment thereof. In a related embodiment, the functional protein is the extracellular domain of a receptor protein or a fraction thereof. In specific embodiments, the peptide mask inhibits the binding of the soluble receptor to its ligand or the peptide mask inhibits the receptor's ligand binding domain. In a more specific embodiment, the receptor is Notch and can be selected from the group consisting Notch1, Notch2, Notch3 and Notch4. In a related embodiment, the Notch ligand is selected from the group consisting DLL1, DLL3, DLL4, Jagged1, and Jagged2. In a specific embodiment, the peptide mask contains a sequence selected from those presented in Table 14 or a sequence having at least 90% homology thereof.

In other embodiments, the cleavable linker is a substrate for an enzyme selected from the substrates in Table 2. In related embodiments, the cleavable linker is a substrate for an enzyme selected from the group consisting of matriptase, plasmin, MMP-9, uPA, HCV-NS3/4, PSA, and legumain, or specifically is a substrate for matriptase or HCV-NS3/4. In one embodiment, the consensus sequence for a matriptase substrate comprises XXQAR(A/V)X (SEQ ID NO: 87) or AGPR (SEQ ID NO: 2). In another embodiment, the consensus sequence for a HCV-NS3/4 substrate comprises DEXXXC(A/S) (SEQ ID NO: 85) or DLXXXT(A/S) (SEQ ID NO: 86). In another embodiment, the sequence for an MMP-9 substrate comprises VHMPLGFLGP (SEQ ID NO: 3). In another embodiment, the sequence for a plasmin substrate comprises QGPMFKSLWD (SEQ ID NO: 4).

In another embodiment the composition further contains an Fc region of an immunoglobulin.

In yet another embodiment, the coupling of the peptide mask to the functional protein is non-covalent.

In some embodiments, the peptide mask inhibits binding of the functional protein to its binding partner allosterically. In other embodiments, the peptide mask inhibits binding of the functional protein to its binding partner sterically.

In most embodiments, the binding affinity of the peptide mask to the functional protein is less than the binding affinity of the binding partner to the functional protein. In a specific embodiment, the dissociation constant ($K_d$) of the peptide mask towards the functional protein is at least 100 times greater than the $K_d$ of the functional protein towards its binding partner. In a more specific embodiment, the $K_d$ of the peptide mask towards the functional protein is lower than about 5 nM.

In another embodiment, when the composition is not in the presence of an enzyme capable of cleaving the cleavable linker, the peptide mask inhibits the binding of the functional protein to its binding partner by at least 90% when compared to when the composition is in the presence of the enzyme capable of cleaving the cleavable linker and the peptide mask does not inhibit the binding of the functional protein to its binding partner.

In another aspect, the present disclosure provides for a pharmaceutical composition, wherein said pharmaceutical composition comprises a therapeutically effective amount of a composition comprising a functional protein that is not an antibody or an antibody fragment, wherein the functional protein is coupled to a peptide mask that: (i) inhibits binding of the functional protein to its binding partner and (ii) does not have an amino acid sequence of the binding partner and a pharmaceutically acceptable excipient. In one specific embodiment of this pharmaceutical composition, the functional protein is further coupled to a cleavable linker capable of being cleaved, such that: (i) in an uncleaved state, the peptide mask inhibits binding of the functional protein to its binding partner and (ii) in a cleaved state, the peptide mask does not inhibit binding of the functional protein to its binding partner.

In another aspect, the present disclosure also provides a method of treating a disease or disorder, wherein a pharmaceutical composition comprising a therapeutically effective amount of a composition comprising a functional protein that is not an antibody or an antibody fragment, wherein the functional protein is coupled to a peptide mask that: (i) inhibits binding of the functional protein to its binding partner and (ii) does not have an amino acid sequence of the binding partner and a pharmaceutically acceptable excipient is administered. In one specific embodiment of this method, the functional protein is further coupled to a cleavable linker capable of being cleaved, such that: (i) in an uncleaved state, the peptide mask inhibits binding of the functional protein to its binding partner and (ii) in a cleaved state, the peptide mask does not inhibit binding of the functional protein to its binding partner. In a specific embodiment, the disease or disorder is cancer. In another specific embodiment, the disease or disorder is a liver condition such as Hepatitis C infection or hepatocellular cancer. In yet another specific embodiment, the disease or disorder involves angiogenesis.

In another aspect, the present disclosure provides for a library comprising a plurality of candidate activatable functional proteins, displayed on the surface of a replicable biological entity. In one embodiment, the functional protein is an interferon or a soluble Notch receptor protein.

In another aspect, the present disclosure provides a method of making a library of candidate peptide masks, comprising: introducing into genomes of replicable biological entities a collection of recombinant DNA constructs that each encode a peptide mask, said introducing producing recombinant replicable biological entities; and culturing said recombinant replicable biological entities under conditions suitable for expression and display of the candidate peptide masks. In a related embodiment, the candidate peptide masks are screened for the ability to bind an interferon protein or a soluble Notch receptor. In a specific embodiment, the interferon protein is pro-IFN-α.

In another aspect, the present disclosure provides a method of screening for a peptide mask, said method comprising: contacting a plurality of candidate peptide masks with a functional protein; and screening a first population of members with a functional protein; wherein said method provides for selection of peptide masks. In one embodiment, the candidate peptide masks are screened for the ability to bind an interferon protein or a soluble Notch receptor. In a specific embodiment, interferon protein is pro-IFN-α.

In another aspect, the present disclosure provides a method of screening for an activatable functional protein coupled to a peptide mask, said method comprising: contacting a plurality of candidate activatable proteins with a binding partner capable of binding the functional protein and an enzyme capable of cleaving a cleavable linker of the activatable protein; screening a first population of members of said plurality which bind to said binding partner in the presence of the enzyme; contacting said first population with the binding partner in the absence of the enzyme; and screening a second population of members from said first population by depleting said first population for members that bind the binding partner in the absence of the enzyme, wherein said method provides for selection of candidate activatable functional proteins which exhibit decreased binding to its binding partner in the absence of the enzyme as compared to binding partner binding in the presence of the enzyme. In one embodiment, the candidate peptide masks are screened for the ability to bind an interferon protein or a soluble Notch receptor. In one specific embodiment, the interferon protein is pro-IFN-α.

In another aspect, the present disclosure provides a method of making a library of candidate activatable functional proteins, each coupled to a peptide mask, said method comprising: introducing into genomes of replicable biological entities a collection of recombinant DNA constructs that encode a plurality of candidate activatable functional proteins, said introducing producing recombinant replicable biological entities; and culturing said recombinant replicable biological entities under conditions suitable for expression and display of the candidate activatable functional proteins. In one embodiment, the candidate activatable functional proteins differ in the sequence of their coupled peptide masks. In a specific embodiment, the functional protein is an interferon or a soluble Notch receptor protein.

In another aspect, the present disclosure provides a method of screening for an activatable functional protein coupled to a peptide, said method comprising: contacting a plurality of candidate activatable proteins with a binding partner capable of binding the functional protein and an enzyme capable of cleaving a cleavable linker of the activatable protein; screening a first population of members of said plurality which bind to said binding partner in the presence of the enzyme; contacting said first population with the binding partner in the absence of the enzyme; and screening a second population of members from said first population by depleting said first population for members that bind the binding partner in the absence of the enzyme; wherein said method provides for selection of candidate activatable functional proteins which exhibit decreased binding to its binding partner in the absence of the enzyme as compared to binding partner binding in the presence of the enzyme. In one embodiment, the functional protein is an interferon or a soluble Notch receptor protein.

In another aspect, the present disclosure provides a vector encoding a functional protein and a peptide mask wherein the peptide mask is capable of inhibiting the functional protein's ability to bind its binding partner. In one embodiment, the functional protein is an interferon protein or a soluble Notch receptor protein.

In one specific aspect the present disclosure provides a modified IFN-α protein comprising a substrate capable of cleavage by matriptase.

In another specific aspect the present disclosure provides a modified IFN-α protein comprising a substrate capable of cleavage by HCV-NS3/4.

In another specific aspect the present disclosure provides a modified soluble Notch receptor protein comprising a substrate capable of cleavage by a matrix metalloproteinase.

In another specific aspect the present disclosure provides a modified soluble Notch receptor protein comprising a substrate capable of cleavage by plasmin.

In another specific aspect the present disclosure provides a modified soluble Notch receptor protein comprising a substrate capable of cleavage by legumain.

In another specific aspect the present disclosure provides a modified soluble Notch receptor protein comprising a substrate capable of cleavage by uPA.

In another specific aspect the present disclosure provides a modified soluble Notch receptor protein comprising a substrate capable of cleavage by PSA.

In another aspect the present disclosure provides a protein therapeutic for the treatment of Hepatitis C having an improved bioavailability comprising a functional protein coupled to a peptide mask and a cleavable linker, wherein the affinity of binding of the protein therapeutic to its target is higher in liver tissue when compared to the binding of the protein therapeutic to its target in a non-liver tissue, wherein target is present in both tissues. In one embodiment, the cleavable linker comprises a substrate specific for a matriptase or HCV NS3/4 enzyme.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Proproteins: Introduction and General Features

Figure 1:
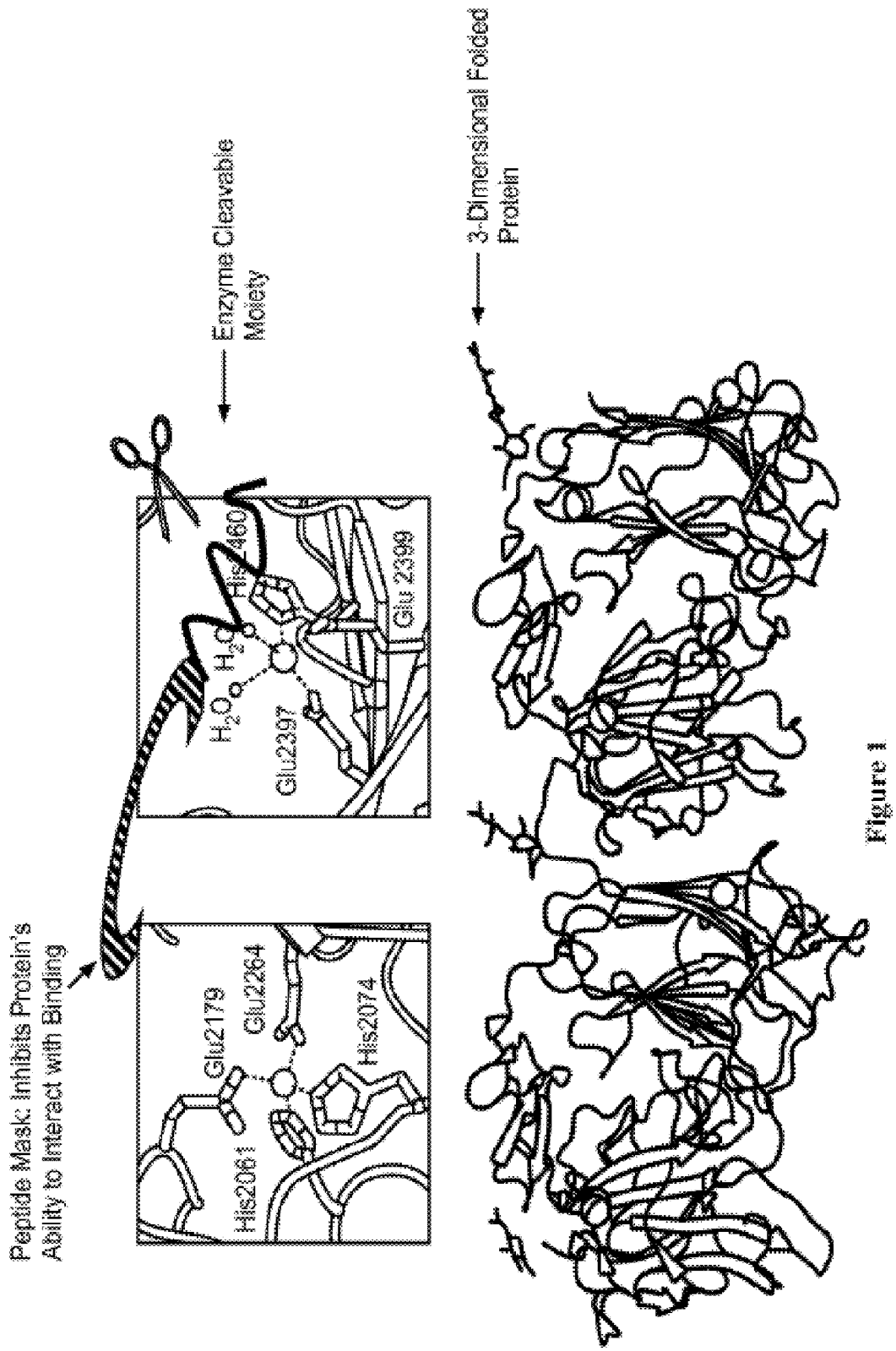
FIG. 1 depicts an exemplary masked activatable folded proprotein. The figures display a protein not capable of binding partner due to Interaction with specific and unique peptide mask.

The present disclosure provides for proproteins.

The proprotein compositions described herein contain a full length protein or a functional fragment of a full-length protein (collectively referred to as 'functional protein' herein) coupled to a peptide mask. The peptide mask can inhibit binding of the functional protein to its binding partner or target (binding partner and target used interchangeably herein). The peptide mask can inhibit binding of the functional protein to its binding partner sterically or allosterically. Generally, the functional protein displays two distinct levels of binding to its binding partner, based on the presence and/or location of the peptide mask.

When a functional protein is coupled to a peptide mask and is in the presence of its binding partner, specific binding of the functional protein to its binding partner can be reduced or inhibited, as compared to the specific binding of the functional protein to its binding partner not coupled to the peptide mask.

A functional protein is a full-length protein or functional fragment thereof and has functional activity or physiological activity (e.g., in vivo or in vitro), such as, for example, binding affinity to a target or binding partner, capability of effecting signaling pathways, has enzymatic activity, or the like. A functional protein fragment also retains functional activity or physiological activity (e.g., in vivo or in vitro). Such activity can be, for example, retaining relevant biological activity of the full length protein, i.e. binding, targeting, signaling, triggering a particular signaling cascade, modulating a particular pathway, and the like.

In one embodiment the functional protein is not an antibody or an antibody fragment.

A functional protein of the present invention can be naturally occurring or non-naturally occurring.

The proproteins of the present invention or the functional protein can be post-translationally modified.

A functional protein can be globular, fibrous, or multimeric.

A functional protein can be an ligand, an extracellular ligand, such as, for example a interferon protein, or more specifically, for example, an IFN-α full length protein, an IFN-β full length protein, an IFN-γ full length protein, or a IFN-w full length protein.

A functional protein can be a soluble membrane protein, for example, a soluble receptor, for example a soluble Notch Receptor, for example Notch1, Notch2, Notch3, or Notch4 receptor.

A functional protein can be taken up intracellularly or can remain extracellular.

Proproteins of the present invention can contain naturally occurring amino acids or non-naturally occurring amino acids, or both. Proproteins of the present invention can contain L-amino acids, D-amino acids, or a mixture of both. In specific embodiments, the functional proteins of the present invention can be coupled to peptide masks that contain naturally occurring or non-naturally occurring amino acids, or both.

Proproteins of the present invention can contain a mutated variant of a naturally occurring full length protein or functional protein fragment. That is, a functional protein can be a mutant of a naturally occurring protein.

The proproteins of the present invention can be synthetically generated.

The proproteins of the present invention can be recombinantly expressed, and purified.

The present disclosure further also provides activatable proproteins.

An activatable proprotein comprises a functional protein or functional fragment thereof, coupled to a peptide mask, and further coupled to an activatable moiety (or activatable linker such as a cleavable linker), wherein in an uncleaved state the peptide mask inhibits binding of the protein to its binding partner and in a cleaved state the peptide mask does not inhibit binding of the protein to a binding partner.

The activatable moiety or activatable linker of activatable proprotein compositions, when activated, can change the conformation of the peptide mask in relationship to the functional protein. By activating the activatable linker, the functional protein can have a different binding affinity to its binding partner or target.

In some instances, the activatable linker is a cleavable linker, containing a substrate capable of being specifically cleaved by an enzyme, protease, or peptidase. In other instances the activatable linker is reducible by a reducing agent. In yet other instances, the activatable linker is a photo-sensitive substrate, capable of being activated by photolysis. As used herein cleavage is used interchangeably to denote activation by an enzyme, a reducing agent, or photolysis.

A schematic of an activatable proprotein is provided in FIG. 1. As illustrated, the elements of the activatable proprotein are arranged so that in an uncleaved state (or relatively inactive state) binding of the protein to the target binding partner is inhibited due to the masking of the protein by the peptide mask.

By activatable it is meant that the proprotein exhibits a first level of binding to a binding partner when in a native or non-activated state (i.e., a first conformation), and a second level of binding to a binding partner in the activated state (i.e., a second conformation), wherein the second level of binding is greater than the first level of binding. In general, access of a binding partner to the functional protein is greater in the presence of an enzyme/reducing agent/light capable of activating the activatable linker than in the absence of such enzyme/reducing agent/light. Thus, in the non-activated or uncleaved state the protein is masked from target binding (i.e., the first conformation is such that the peptide mask inhibits access of the binding partner to the protein), and in the activated state the protein is unmasked to the binding partner.

When the functional protein is coupled to both a peptide mask and an activatable moiety, and is in the presence of its binding partner but not in the presence of sufficient enzyme/reductase/light to activate the activatable moiety, specific binding of the functional protein to its binding partner is inhibited, as compared to the specific binding of the functional protein to its binding partner when in the presence of sufficient enzyme/reductase/light to activate the activatable moiety.

Proproteins can provide for reduced toxicity and/or adverse side effects that could otherwise result from binding of a functional protein at non-treatment sites if it were not inhibited from binding its binding partner. Proproteins can provide for improved biodistribution characteristics. Proproteins containing a masked protein can display a longer in vivo or serum half-life than the corresponding unmasked protein.

In general, a proprotein can be designed by selecting a full length or functional fragment of a protein of interest, and constructing the remainder of the proprotein so that, when conformationally constrained, the peptide mask sterically or allosterically provides for masking of the binding site of the protein. Structural design criteria can be taken into account to provide for the masking feature. Preferably, the proprotein is genetically encoded and recombinantly expressed, but can also be synthetically produced.

Proproteins exhibiting an activatable phenotype of a desired dynamic range for target binding in a cleaved versus uncleaved conformation are provided. Dynamic range generally refers to a ratio of (a) a detected level of a parameter under a first set of conditions to (b) a detected value of that parameter under a second set of conditions. For example, in the context of a proprotein, the dynamic range refers to the ratio of (a) a detected level of target protein binding to a proprotein in the presence of an enzyme such as a protease capable of cleaving the cleavable linker of the proprotein to (b) a detected level of target protein binding to a proprotein in the absence of the protease. The dynamic range of a proprotein can be calculated as the ratio of the equilibrium dissociation constant of a proprotein cleaving agent (e.g., enzyme) treatment to the equilibrium dissociation constant of the proprotein cleaving agent treatment. The greater the dynamic range of a proprotein, the better the activatable phenotype of the proprotein. Proproteins having relatively higher dynamic range values (e.g., greater than 1, 2, 3, 4, 5, or more) exhibit more desirable activating phenotypes such that target protein binding by the proprotein occurs to a greater extent (e.g., predominantly occurs) in the presence of a cleaving agent (e.g., enzyme) capable of cleaving the cleavable linker of the proprotein than in the absence of a cleaving agent.

Activatable proproteins can be provided in a variety of structural configurations. Exemplary formulae for proproteins are provided below. It is specifically contemplated that the N- to C-terminal order of the functional protein, the peptide mask, and the cleavable linker may be reversed within a proprotein. It is also specifically contemplated that the cleavable linker and peptide mask may overlap in amino acid sequence, e.g., such that the cleavable linker is contained within the peptide mask.

For example, proproteins can be represented by the following formula (in order from an amino (N) terminal region to carboxyl (C) terminal region.

(peptide mask)-(linker)-(functional protein)

(functional protein)-(linker)-(peptide mask)

(peptide mask)-(activatable linker)-(functional protein)

(functional protein)-(activatable linker)-(peptide mask)

It should be noted that although the peptide mask and cleavable linker are indicated as distinct components in the formula above, in all exemplary embodiments disclosed herein it is contemplated that the amino acid sequences of the peptide mask and the cleavable linker could overlap, e.g., such that the cleavable linker is completely or partially contained within the peptide mask. In addition, the formulae above provide for additional amino acid sequences that may be positioned N-terminal or C-terminal to the proprotein elements.

In many embodiments it may be desirable to insert one or more linkers, e.g., flexible linkers, into the proprotein construct so as to provide for flexibility at one or more of the peptide mask-activatable/cleavable linker junction, the activatable/cleavable linker-protein junction, or both. For example, the functional protein, peptide mask, and/or activatable/cleavable linker may not contain a sufficient number of amino acid residues (e.g., Gly, Ser, Asp, Asn, especially Gly and Ser, particularly Gly) to provide the desired flexibility. The linkers may comprise stretches of amino acids that are or that are not naturally occurring. As such, the activatable phenotype of such proprotein constructs may benefit from introduction of one or more amino acids to provide for a flexible linker.

Exemplary flexible linkers include glycine polymers (G), glycine-serine polymers (including, for example, $(GS)_n$, $(GSGGS)_n$ (SEQ ID NO: 5) and $(GGGS)_n$ (SEQ ID NO: 6), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 7), Gly-Gly-Ser-Gly-Gly (SEQ ID NO: 8), Gly-Ser-Gly-Ser-Gly (SEQ ID NO: 9), Gly-Ser-Gly-Gly-Gly (SEQ ID NO: 10), Gly-Gly-Gly-Ser-Gly (SEQ ID NO: 11), Gly-Ser-Ser-Ser-Gly (SEQ ID NO: 12), and the like. The ordinarily skilled artisan will recognize that design of a proprotein can include linkers that are all or partially flexible, such that the linker can include a flexible linker as well as one or more portions that confer less flexible structure to provide for a desired proprotein structure.

Linkers suitable for use in proproteins are generally ones that provide flexibility of the proprotein to facilitate a masked conformation. Such linkers are generally referred to as flexible linkers. Suitable linkers can be readily selected and can be of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19 or 20 amino acids.

For example, proproteins containing these optional flexible linkers can be represented by the following formulas (in order from an amino (N) terminal region to carboxyl (C) terminal region.

(peptide mask)-(optional flexible linker)-(activatable linker)-(optional flexible linker)-(functional protein)

(functional protein)-(optional flexible linker)-(activatable linker)-(optional flexible linker)-(peptide mask)

In addition to the elements described above, the proproteins can be coupled to additional elements or extra features, such as an additional therapeutic moiety, a targeting moiety to facilitate delivery to a cell or tissue of interest, a moiety to direct binding to a target receptor to facilitate localization of the proprotein, a Fc region of an immunoglobulin to increase serum half-life of the proprotein, for example, and the like.

For example, proproteins containing these optional additional elements or features can be represented by the following formulas (in order from an amino (N) terminal region to carboxyl (C) terminal region).

(targeting moiety for cellular uptake)-(peptide mask)-(activatable linker)-(functional protein)

(functional protein)-(activatable linker)-(peptide mask)-(targeting moiety for cellular uptake)

(Fc)-(peptide mask)-(activatable linker)-(functional protein)

(functional protein)-(activatable linker)-(peptide mask)-(Fc)

The dissociation constant ($K_d$) of the functional protein towards its binding partner when coupled to a peptide mask is greater than the $K_d$ of the functional protein towards its binding partner when not coupled to a peptide mask. Conversely, the binding affinity of the functional protein towards its binding partner when coupled to a peptide mask is lower than the binding affinity of the functional protein towards its binding partner when not coupled to a peptide mask.

The $K_d$ of the peptide mask towards the functional protein is generally greater than the $K_d$ of the functional protein towards its binding partner. Conversely, the binding affinity of the peptide mask towards the functional protein is generally lower than the binding affinity of the functional protein towards its binding partner.

The peptide mask can inhibit the binding of the functional protein to its binding partner. The peptide mask can bind a binding domain of the functional protein and inhibit binding of the functional protein to its binding partner. The peptide mask can sterically interfere with the binding of the functional protein to its binding partner. The peptide mask can allosterically inhibit the binding of the functional protein to its binding partner. In these embodiments when the functional protein is modified or coupled to a peptide mask and in the presence of binding partner, there is no binding or substantially no binding of the functional protein to its binding partner as compared to the binding of the functional protein not coupled to a peptide mask. This can be measured in vivo or in vitro in a Mask Efficiency Assay, an immunoabsorbant assay, as described herein.

When a functional protein is coupled to a peptide mask, the peptide mask can 'mask' or reduce, or inhibit the specific binding of the functional protein to its binding partner. When a functional protein is coupled to a peptide mask, such coupling or modification can effect a structural change which reduces or inhibits the ability of the functional protein to specifically bind its binding partner.

The disclosure further provides methods of use, methods of screening, and methods of making peptide-masked functional proteins.

The components of the proprotein compositions provided herein are described in greater detail following.

Functional Proteins and Binding Partners

The present disclosure provides for a full-length protein or a functional protein fragment coupled to a peptide mask that inhibits the functional protein from interacting with a binding partner or target. The functional proteins for use contemplated by the present disclosure can be any full length protein or functional fragment thereof (referred to interchangeably as 'functional proteins'). By functional protein, it is indicated that the full length protein, or functional fragment thereof, retains relevant biological activity, i.e. binding, targeting, signaling, etc. Once unmasked, the binding of the functional protein to its binding partner or target can provide for a desired biological effect, e.g., inhibition of activity of the target protein and/or detection of a target protein. Once unmasked, a functional protein can bind to one binding partner or multiple binding partners.

The functional protein can be a naturally or non-naturally occurring protein.

The functional protein can be recombinantly expressed, genetically encoded, and/or post translationally modified. The functional protein can be synthetically constructed.

The functional protein can be a mutant of a naturally occurring protein. The mutated functional protein can retain no more than 95%, 90%, 80%, 75%, 70,%, 60%, 50%, 40%, 30%, 25%, or 20% nucleic acid or amino acid sequence homology to the non-mutated functional protein.

The functional protein can be globular, fibrous, or multimeric. The functional protein can exhibit folding, and can exhibit primary, secondary, or quaternary structure.

The functional protein can be a ligand, for example, an interferon protein, for example an IFN-α protein (type 2a, 2b or con1), IFN-β protein, IFN-γ protein, or an IFN-ω protein. The functional protein can be a soluble membrane protein, for example, a soluble receptor, for example a soluble Notch Receptor (for example Notch1, Notch2, Notch3, or Notch4 receptor).

The functional protein can be designed to remain extracellularly or designed for cellular uptake in its unmasked state.

Throughout the present disclosure the terms binding partner and target are used interchangeably. The binding partner of the functional protein can be extracellular, intracellular, or a transmembrane protein. In one embodiment its binding partner of the functional protein is an extracellular protein, such as a ligand or a soluble receptor. In another embodiment the binding partner of the functional protein is an intracellular protein and the functional protein is capable of cellular uptake and is designed to be unmasked inside a cell. In another embodiment, the binding partner of the functional protein is a membrane-associated receptor.

Exemplary binding partners/targets are interferon protein receptors, or specifically IFNAR, IFNAR1, IFNAR2, and IFNLR1. Other exemplary binding partner/targets are Notch ligands such as DLL1, DLL3, DLL4, Jagged1, and Jagged 2.

A functional protein of the invention can specifically bind to its target or binding partner with a dissociation constant ($K_d$) of no more than 1000 nM, 100 nM, 50 nM, 10 nM, 5 nM, 1 nM, 500 pM, 400 pM, 350 pM, 300 pM, 250 pM, 200 pM, 150 pM, 100 pM, 50 pM, 25 pM, 10 pM, 5 pM, 1 pM, 0.5 pM, or 0.1 pM.

In certain embodiments the functional protein coupled with a peptide mask is not an antibody or antibody fragment.

Exemplary sources for the functional protein to generate interferon-related proproteins contemplated are provided in Table 1.

TABLE 1

Exemplary Sources for Interferon-related proproteins

Peginterferon Lambda
PEGASYS (Peginterferon alfa-2a)

TABLE 1-continued

Exemplary Sources for Interferon-related proproteins

Peginterferon (Rebetol)
Actimmune (Interferon γ1b)
Avonex (Interferon β1a)
Betaseron (Interferon β1b)
Rebif (Interferon β1a)
INTRON A (Interferon α-2b)
PegIntron (Peginterferon α-2b)

Peptide Masks

The present disclosure provides for a functional protein coupled to a peptide mask (also interchangeably referred to as a masking peptide or a masking moiety) which inhibits the functional protein from interacting with a binding partner. The peptide mask can specifically interact with the functional protein and reduce or inhibit the interaction between the functional protein and its binding partner.

When the functional protein is in a 'masked' state, even in the presence of a binding partner for the functional protein, the peptide mask interferes with or inhibits the binding of the functional protein to its binding partner. However, in the unmasked state of the functional protein, the peptide mask's interference with target binding to the functional protein is reduced, thereby allowing greater access of the functional protein to the target and providing for target binding.

For example, when the proprotein comprises an activatable moiety, the functional protein can be unmasked upon cleavage of the activatable moiety, in the presence of enzyme, preferably a disease-specific enzyme. Thus, the peptide mask is one that when the proprotein is uncleaved provides for masking of the functional protein from target binding, but does not substantially or significantly interfere or compete for binding of the target to the functional protein when the proprotein is in the cleaved conformation. Thus, the combination of the peptide mask and the activatable moiety facilitates the switchable/activatable phenotype, with the peptide mask decreasing binding of target when the proprotein is uncleaved, and cleavage of the activatable moiety by protease providing for increased binding of target.

The structural properties of the peptide mask can vary according to a variety of factors such as the minimum amino acid sequence required for interference with protein binding to target, the target protein-protein binding pair of interest, the size of the functional protein, the length of the activatable moiety, whether the activatable moiety is positioned within the peptide mask and also serves to mask the functional protein in the uncleaved proprotein, the presence or absence of linkers, the presence or absence of a cysteine within or flanking the functional protein that is suitable for providing an activatable moiety of a cysteine-cysteine disulfide bond, and the like.

In one embodiment, the peptide mask can be coupled to the functional protein by covalent binding. In another embodiment, the functional protein is prevented from binding to its target by binding the peptide mask to an N-terminus of the functional protein. In yet another embodiment, the functional protein is coupled to the peptide mask by cysteine-cysteine disulfide bridges between the peptide mask and the functional protein.

The peptide mask can be provided in a variety of different forms. The peptide mask can be selected from a known binding partner of the functional protein, provided that the peptide mask binds the functional protein with less affinity and/or avidity than the target protein to which the functional protein is designed to bind, following cleavage of the activatable moiety so as to reduce interference of peptide mask in target-protein binding. Stated differently, as discussed above, the peptide mask is one that masks the functional protein from target binding when the proprotein is uncleaved, but does not substantially or significantly interfere or compete for binding for target when the proprotein is in the cleaved conformation.

Generally, the peptide mask is unique for the functional protein of interest. Examples of peptide masks that specifically interact with the functional protein of the proprotein include peptide masks that were specifically screened to bind a binding domain of the functional protein or protein fragment. Methods for screening peptide masks to obtain peptide masks unique for the functional protein and those that specifically and/or selectively bind a binding domain of a binding partner/target are provided herein and can include protein display methods.

The present disclosure provides for peptide masks that can specifically inhibit the interaction between the functional protein and its binding partner. Each peptide mask has a certain binding affinity for the functional protein. The binding affinity is generally lower than the binding affinity between the functional protein and its binding partner.

The peptide mask of the present disclosure generally refers to an amino acid sequence coupled to a functional protein and is positioned such that it reduces the functional protein's ability to specifically bind its binding partner. In some cases the peptide mask is coupled to the functional protein by way of a linker.

When the functional protein is coupled to a peptide mask and is in the presence of its binding partner, specific binding of the functional protein to its binding partner can be reduced or inhibited, as compared to the specific binding of the functional protein not coupled to a peptide mask or the specific binding of the parental protein to its binding partner. When the functional protein is coupled to both an activatable moiety and a peptide mask and is in the presence of its binding partner but not sufficient enzyme or enzyme activity to cleave the activatable moiety, specific binding of the modified protein to its binding partner is reduced or inhibited, as compared to the specific binding of the functional protein coupled to an activatable moiety and a peptide mask in the presence of its binding partner and sufficient enzyme/enzyme activity/reducing agent/reducing agent activity/light to activate the activatable moiety.

The peptide mask can inhibit the binding of the functional protein to its binding partner. The peptide mask can bind the binding domain of the functional protein and inhibit binding of the functional protein to its binding partner. The peptide mask can sterically inhibit the binding of the functional protein to its binding partner. The peptide mask can allosterically inhibit the binding of the functional protein to its binding partner.

When a functional protein is coupled to a peptide mask and in the presence of binding partner, there is no binding or substantially no binding of the functional protein to the binding partner, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the functional protein to its binding partner, as compared to the binding of the functional protein not coupled to a peptide mask, the binding of the parental protein, or the binding of the functional protein not coupled to a peptide mask to its binding partner, for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a Mask Efficiency Assay, an in vitro immunoabsorbant assay, as described herein.

The peptide mask can be a synthetically produced string of amino acids that are capable of inhibiting the interaction of a functional protein with its binding partner. The peptide mask can be part of a linker or activatable moiety. In related embodiments the peptide mask can be selected in an unbiased manner upon screening for specific and selective binding to the functional protein.

In certain embodiments, the peptide mask can have at least partial or complete amino acid sequence of a naturally occurring binding partner of the functional protein. The peptide mask can be a fragment of a naturally occurring binding partner. The fragment can retain no more than 95%, 90%, 80%, 75%, 70,%, 60%, 50%, 40%, 30%, 25%, or 20% nucleic acid or amino acid sequence homology to the naturally occurring binding partner.

In some instances the peptide mask has an amino acid sequence that is not naturally occurring or does not contain the amino acid sequence of a naturally occurring binding partner or target protein. In certain embodiments the peptide mask is not a natural binding partner of the functional protein. The peptide mask may be a modified binding partner for the functional protein which contains amino acid changes that at least slightly decrease affinity and/or avidity of binding to the functional protein. In some embodiments the peptide mask contains no or substantially no nucleic acid or amino acid homology to the functional protein's natural binding partner. In other embodiments the peptide mask is no more than 5%, 10%, 15%, 20%, 25%, 30%, 35%, 40%, 45%, 50%, 55%, 60%, 65%, 70%, 75%, or 80% similar to the natural binding partner of the functional protein.

The present disclosure also provides for variants for a given peptide mask. The sequence of the peptide masks can be varied to retain at least 95%, 90%, 80%, 75%, 70,%, 60%, 50%, 40%, 30%, 25%, or 20% nucleic acid or amino acid sequence homology to the peptide mask. Such sequence variations may afford an improved masking ability.

The efficiency of the peptide mask to inhibit the binding of the functional protein to its target when coupled can be measured by a Masking Efficiency Assay, using an in vitro immunoabsorbant assay, as described herein in the Examples section of the disclosure. Masking efficiency of peptide masks is determined by at least two parameters: affinity of the peptide mask for the functional protein and the spatial relationship of the peptide mask relative to the binding interface of the functional protein to its target.

Regarding affinity, by way of example, a peptide mask may have high affinity but only partially inhibit the binding site on the functional protein, while another peptide mask may have a lower affinity for the functional protein but fully inhibit target binding. For short time periods, the lower affinity peptide mask may show sufficient masking; in contrast, over time, that same peptide mask may be displaced by the target (due to insufficient affinity for the functional protein).

In a similar fashion, two peptide masks with the same affinity may show different extents of masking based on how well they promote inhibition of the binding site on the functional protein or prevention of the functional protein from binding its target. In another example, a peptide mask with high affinity may bind and change the structure of the functional protein so that binding to its target is completely inhibited while another peptide mask with high affinity may only partially inhibit binding. As a consequence, discovery of an effective peptide mask is often not based only on affinity but can include an empirical measure of Masking Efficiency. The time-dependent target displacement of the peptide mask in the functional protein can be measured to optimize and select for peptide masks. A novel Masking Efficiency Assay is described herein for this purpose.

A peptide mask can be identified and further optimized through a screening procedure from a library of candidate proproteins having variable peptide masks. For example, a functional protein and activatable moiety can be selected to provide for a desired enzyme/target combination, and the amino acid sequence of the peptide mask can be identified by the screening procedure described below to identify a peptide mask that provides for a switchable phenotype. For example, a random peptide library (e.g., from about 2 to about 40 amino acids or more) may be used in the screening methods disclosed herein to identify a suitable peptide mask. In specific embodiments, peptide masks with specific binding affinity for a functional protein can be identified through a screening procedure that includes providing a library of peptide scaffolds consisting of candidate peptide masks wherein each scaffold is made up of a transmembrane protein and the candidate peptide mask. The library is then contacted with an entire or portion of a protein such as a full length protein, a naturally occurring protein fragment, or a non-naturally occurring fragment containing a protein (also capable of binding the binding partner of interest), and identifying one or more candidate peptide masks having detectably bound protein. Screening can include one more rounds of magnetic-activated sorting (MACS) or fluorescence-activated sorting (FACS). Screening can also included determination of the dissociation constant ($K_d$) of peptide mask towards the functional protein and subsequent determination of the Masking Efficiency.

In this manner, proproteins having a peptide mask that inhibits binding of the functional protein to its binding partner in an non-activated state and allows binding of the functional protein to its binding partner in a activated state can be identified, and can further provide for selection of a proprotein having an optimal dynamic range for the switchable phenotype. Methods for identifying proproteins having a desirable switching phenotype are described in more detail herein. Alternatively, the peptide mask may not specifically bind the functional protein, but rather interfere with protein-binding partner binding through non-specific interactions such as steric hindrance. For example, the peptide mask may be positioned in the uncleaved proprotein such that the tertiary or quaternary structure of the proprotein allows the peptide mask to mask the functional protein through charge-based interaction, thereby holding the peptide mask in place to interfere with binding partner access to the functional protein.

Proproteins can also be provided in a conformationally constrained structure, such as a cyclic structure, to facilitate the switchable phenotype. This can be accomplished by including a pair of cysteines in the proprotein construct so that formation of a disulfide bond between the cysteine pairs places the proprotein in a loop or cyclic structure. Thus the proprotein remains cleavable by the desired protease while providing for inhibition of target binding to the functional protein. Upon activation of the activatable moiety, the cyclic structure is opened, allowing access of binding partner to the functional protein.

The cysteine pairs can be positioned in the proprotein at any position that provides for a conformationally constrained proprotein, but that, following activatable moiety reduction, does not substantially or significantly interfere with target binding to the functional protein. For example, the cysteine residues of the cysteine pair are positioned in the peptide mask and a linker flanked by the peptide mask and protein, within a linker flanked by the peptide mask and protein, or other suitable configurations. For example, the peptide mask or a linker flanking a peptide mask can include one or more cysteine residues, which cysteine residue forms a disulfide bridge with a cysteine residue positioned opposite the peptide mask when the proprotein is in a folded state. It is generally desirable that the cysteine residues of the cysteine pair be positioned outside the functional protein so as to avoid interference with target binding following cleavage of the proprotein. Where a cysteine of the cysteine pair to be disulfide bonded is positioned within the functional protein, it is desirable that it be positioned to as to avoid interference with protein-target binding following exposure to a reducing agent.

In certain embodiments, once an activatable proprotein is activated, the peptide mask is uncoupled from the functional protein, whereby unmasking the functional protein. In some embodiments, once uncoupled from the functional protein and in a free state, the peptide has biological activity or a therapeutic effect, such as binding capability. For example, the free peptide can bind with the same or a different binding partner. In certain embodiments the free peptide mask (uncoupled peptide mask) can exert a therapeutic effect, providing a secondary function to the compositions of this invention.

The peptide masks contemplated by this disclosure can range from 1-50 amino acids; in some instances can be at least than 3, 4, 5, 6, 7, 8, 9, 10, 12, 15, 20, 30, or 40 amino acids, or no greater than 40, 30, 20, 15, 12, 10, 9, 8, 7, 6, 5, 4, or 3 amino acids. In specific embodiments the peptide masks of the present invention are 8-15 amino acids in length.

The peptide masks of the present invention can contain genetically encoded or genetically non-encoded amino acids. Examples of genetically non-encoded amino acids are but not limited to D-amino acids, β-amino acids, and γ-amino acids. In specific embodiments, the peptide masks contain no more than 50%, 40%, 30%, 20%, 15%, 10%, 5% or 1% of genetically non-encoded amino acids.

The dissociation constant ($K_d$) of the functional protein towards the target or binding partner when coupled to a peptide mask can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the functional protein towards its binding partner when not coupled to a peptide mask or the parental protein. Conversely, the binding affinity of the functional protein towards its binding partner when coupled to a peptide mask can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times lower than the binding affinity of the functional protein towards its binding partner when not coupled to a peptide mask.

The $K_d$ of the peptide mask towards the functional protein is generally greater than the $K_d$ of the functional protein towards its binding partner. The $K_d$ of the peptide mask towards the functional protein can be at least 5, 10, 25, 50, 100, 250, 500, 1,000, 2,500, 5,000, 10,000, 100,000, 1,000,000 or even 10,000,000 times greater than the $K_d$ of the functional protein towards its binding partner. Conversely, the binding affinity of the peptide mask towards the functional protein is generally lower than the binding affinity of the functional protein towards its binding partner. The binding affinity of peptide mask towards the functional protein can be at least 5, 10, 25, 50, 100, 250, 500, 1,000, 2,500, 5,000, 10,000, 100,000, 1,000,000 or even 10,000,000 times lower than the binding affinity of the functional protein towards its binding partner.

When the functional protein is coupled to a peptide mask and is in the presence of the binding partner, specific binding of the functional protein to its binding partner can be reduced or inhibited, as compared to the specific binding of the functional protein not coupled to a peptide mask to its binding partner. When compared to the binding of the functional protein not coupled to a peptide mask to its binding partner, the functional protein's ability to bind the binding partner when coupled to a peptide mask can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Mask Efficiency Assay, an in vitro immunoabsorbant assay, as described herein.

The peptide mask can inhibit the binding of the functional protein to its binding partner. The peptide mask can bind a binding domain of the functional protein and inhibit binding of the functional protein to its binding partner. The peptide mask can sterically interfere with the binding of the functional protein to its binding partner. The peptide mask can allosterically inhibit the binding of the functional protein to its binding partner. In these embodiments when the functional protein is coupled to a peptide mask and in the presence of binding partner, there is no binding or substantially no binding of the functional protein to its binding partner, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the functional protein to its binding partner, as compared to the binding of the functional protein not coupled to a peptide mask, or the functional protein not coupled to a peptide mask to its binding partner, for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Masking Efficiency Assay, as described herein.

When a functional protein is coupled to or coupled to a peptide mask, the peptide mask can 'mask' or reduce, or inhibit the specific binding of the functional protein to its binding partner. When a functional protein is coupled to or coupled to a peptide mask, such coupling or modification can effect a structural change which reduces or inhibits the ability of the functional protein to specifically bind its binding partner.

A functional protein coupled to or coupled to a peptide mask can be represented by the following formulae (in order from an amino (N) terminal region to carboxyl (C) terminal region. As depicted in the formula, it may be further desirable to insert one or more linkers, e.g. flexible linkers, in to the composition to provide for increased flexibility.

(peptide mask)-(functional protein)

(functional protein)-(peptide mask)

(peptide mask)-(linker)-(functional protein)

(functional protein)-(linker)-(peptide mask)

Exemplary peptide masks can contain sequences as presented in Tables 3 and 14. A peptide mask of the invention can contain a sequence selected from those presented in Table 3 or a sequence at least having 20%, 30%, 40%, 50%, 60%, 70%, 80%, 90% or 95% homology thereof. A peptide mask of the invention can contain a sequence selected from those presented in Table 14 or a sequence at least having 20%, 30%, 40%, 50%, 60%, 70%, 80%, 90% or 95% homology thereof.

An exemplary peptide mask can contain the consensus sequence TDVDYYREWXXXXXXXX (SEQ ID NO: 1).

Other exemplary peptide masks can be specific for an interferon protein, for example an IFN-$\alpha$ protein (type 2a, 2b or con1), IFN-$\beta$ protein, IFN-$\gamma$ protein, or an IFN-$\omega$ protein. Other exemplary peptide masks can be specific for a Notch Receptor, for example Notch1, Notch2, Notch3, or Notch4 receptor.

Activatable Moieties

The present invention provides for activatable proproteins containing both a peptide mask and an activatable moiety or domain which modulates the proprotein's ability to bind its binding partner. Such compositions are referred to as activatable proproteins.

By activatable it is meant that the proprotein exhibits a first level of binding to a binding partner when in a native (e.g., uncleaved state) (i.e., a first conformation), and a second level of binding to its binding partner in the activated (e.g., cleaved state) (i.e., a second conformation). The second level of binding partner binding is greater than the first level of binding.

For example, a proprotein can comprise a full-length protein or functional fragment thereof, a peptide mask and an activatable moiety that modulates the functional protein's ability to bind its target or binding partner. The activatable moiety can be a cleavable linker. In such an example, in an uncleaved state, the functional protein is coupled to the peptide mask and the peptide mask interferes with the functional protein's ability to bind its binding partner but in a cleaved state, the functional protein is uncoupled and the functional protein can interact with its binding partner. Methods for screening for substrates for enzymes that can be utilized as cleavable linkers according to the present invention are described herein.

The cleavable linkers of the present disclosure may include an amino acid sequence that can serve as a substrate for a protease, reductase, or photolysis. The cleavable linker is positioned in the masked functional protein such that when the linker is cleaved by a such as an enzyme or a protease in the presence of a binding partner, resulting in a cleaved state, the functional protein binds the binding partner, and in an uncleaved state, in the presence of the binding partner, binding of the functional protein to its binding partner is inhibited by the peptide mask. It should be noted that the amino acid sequence of the cleavable linker may overlap with or be included within the peptide mask, such that all or a portion of the cleavable linker facilitates "masking" of the functional protein when the proprotein is in the uncleaved conformation.

In general, access of binding partner to the functional protein is greater in the presence of an enzyme capable of cleaving the cleavable linker than in the absence of such an enzyme. Thus, in the native or uncleaved state the proprotein is prevented from binding to its partner (i.e., the first conformation is such that it interferes with access of the binding partner to the proprotein), and in the cleaved state the functional protein is unmasked to binding its partner.

The activatable moiety may be selected based on a protease that is co-localized in tissue with the desired binding partner of the functional protein. A variety of different conditions are known in which a binding partner of interest is co-localized with a protease, where the substrate of the protease is known in the art. In the example of cancer, the binding partner tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-liming examples of disease include: all types of cancers (breast, lung, colorectal, prostate, head and neck, pancreatic, etc), rheumatoid arthritis, Crohn's disease, melanomas, SLE, cardiovascular damage, ischemia, etc. Furthermore, anti-angiogenic targets, such as VEGF, are known. As such, where the functional protein is selected such that it is capable of binding an anti-angiogenic target such as Notch 1, a suitable activatable moiety will be one which comprises a peptide substrate that is cleavable by a protease that is present at the cancerous treatment site, particularly that is present at elevated levels at the cancerous treatment site as compared to non-cancerous tissues. In one exemplary embodiment, a functional protein can bind an Interferon receptor and the activatable moiety can be a matrix metalloprotease (MMP) substrate, and thus is cleavable by an MMP. In other embodiments, the functional protein can bind a target of interest and the activatable moiety can be, for example, legumain, plasmin, matriptase, HCV-NS3/4, TMPRSS-3/4, MMP-9, MT1-MMP, cathepsin, caspase, human neutrophil elastase, beta-secretase, uPA, or PSA. In other embodiments, the proprotein is activated by other disease-specific proteases, in diseases other than cancer such as Hepatitis C.

The unmodified or uncleaved activatable moiety can allow for efficient inhibition or masking of the functional protein by tethering the peptide mask to the functional protein. When the activatable moiety is modified (cleaved, reduced, photolysed), the functional protein is no longer inhibited or unmasked and can bind its binding partner.

The activatable moiety is capable of being specifically modified (cleaved, reduced or photolysed) by an agent (i.e. enzyme, reducing agent, light) at a rate of about 0.001-1500×104 M-1S-1 or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500 \times 10^4$ $M^{-1}$ $S^{-1}$.

For specific cleavage by an enzyme, contact between the enzyme and activatable moiety is made. When the proprotein comprising a functional protein coupled to a peptide mask and an activatable moiety is in the presence of target and sufficient enzyme activity, the activatable moiety can be cleaved. Sufficient enzyme activity can refer to the ability of the enzyme to make contact with the activatable moiety and effect cleavage. It can readily be envisioned that an enzyme may be in the vicinity of the activatable moiety but unable to cleave because of other cellular factors or protein modification of the enzyme.

Exemplary substrates can include but are not limited to substrates cleavable by one or more of the following enzymes or proteases in Table 2.

TABLE 2

Exemplary Enzymes/Proteases

| | | | |
|---|---|---|---|
| ADAM10 | Caspase 8 | Cathepsin S | MMP 8 |
| ADAM12 | Caspase 9 | FAP | MMP 9 |
| ADAM17 | Caspase 10 | Granzyme B | MMP-13 |
| ADAMTS | Caspase 11 | Guanidinobenzoatase (GB) | MMP 14 |
| ADAMTS5 | Caspase 12 | Hepsin | MT-SP1 |
| BACE | Caspase 13 | Human Neutrophil Elastase (HNE) | Neprilysin |
| Caspases | Caspase 14 | Legumain | HCV-1\153/4 |
| Caspase 1 | Cathepsins | Matriptase 2 | Plasmin |
| Caspase 2 | Cathepsin A | Meprin | PSA |
| Caspase 3 | Cathepsin B | MMP 1 | PSMA |
| Caspase 4 | Cathepsin D | MMP 2 | TACE |
| Caspase 5 | Cathepsin E | MMP 3 | TMPRSS 3/4 |
| Caspase 6 | Cathepsin K | MMP 7 | uPA |
| Caspase 7 | MT1-MMP | neurosin | calpain |
| tPA | HCV-NS3/4A | | |

Exemplary consensus sequences for specific enzymes are presented in Tables 11 and 12. In one embodiment the consensus sequence for a matriptase substrate comprises XXQAR(A/V)X (SEQ ID NO: 87) or AGPR (SEQ ID NO: 2). In another embodiment the consensus sequence for a HCV-NS3/4 substrate comprises DEXXXC(A/S) (SEQ ID NO: 85) or DLXXXT(A/S) (SEQ ID NO: 86).

In one embodiment the sequence for a MMP-9 substrate is VHMPLGFLGP (SEQ ID NO: 3). In another embodiment the sequence for a plasmin substrate is QGPMFKSLWD (SEQ ID NO: 4).

Identifying and Optimizing Proproteins and Components Thereof

Methods for identifying and/or optimizing proproteins and components thereof, as well as compositions useful in such methods, are described below.

Libraries of Candidate Proproteins and their Components, and Display on Replicable Biological Entities In general, the screening methods to identify a proprotein, its components such as the peptide mask/peptide and the cleavable linker and/or to optimize a proprotein for an activatable phenotype involve production of a library of replicable biological entities (as exemplified by cells) that display on their surface a plurality of different candidate proproteins. These libraries can then be subjected to screening methods to identify candidate proproteins and components having one or more desired characteristics of a proprotein and its components.

The candidate proprotein libraries can contain candidate proproteins that differ by one or more of the peptide mask, linker (which may be part of the peptide mask), cleavable linker (which may be part of the peptide mask), and protein. To identify candidate peptide masks or peptides, the candidate proproteins in the library are variable for the peptide mask and/or the linker.

Suitable replicable biological entities include cells (e.g., bacteria (e.g., E. coli), yeast (e.g., S. cerevisiae), mammalian cells), bacteriophage, and viruses. Bacterial host cells and bacteriophage, particularly bacterial host cells, are of interest.

A variety of display technologies using replicable biological entities are known in the art. These methods and entities include, but are not limited to, display methodologies such as mRNA and ribosome display, eukaryotic virus display, and phage, bacterial, yeast, and mammalian cell surface display. See Wilson, D. S., et al. 2001 PNAS USA 98(7):3750-3755; Muller, O. J., et al. (2003) Nat. Biotechnol. 3:312; Bupp, K. and M. J. Roth (2002) Mol. Ther.

5(3):329 3513; Georgiou, G., et al., (1997) Nat. Biotechnol. 15(1):29 3414; and Boder, E. T. and K. D. Wittrup (1997) Nature Biotech. 15(6):553 557. Surface display methods are attractive since they enable application of fluorescence-activated cell sorting (FACS) for library analysis and screening. See Daugherty, P. S., et al. (2000) J. Immunol. Methods 243(1 2):211 2716; Georgiou, G. (2000) Adv. Protein Chem. 55:293 315; Daugherty, P. S., et al. (2000) PNAS USA 97(5):2029 3418; Olsen, M. J., et al. (2003) Methods Mol. Biol. 230:329 342; Boder, E. T. et al. (2000) PNAS USA 97(20):10701 10705; Mattheakis, L. C., et al. (1994) PNAS USA 91(19): 9022 9026; and Shusta, E. V., et al. (1999) Curr. Opin. Biotech. 10(2):117 122. Exemplary phage display and cell display compositions and methods are described in U.S. Pat. Nos. 5,223,409; 5,403,484; 7,118,879; 6,979,538; 7,208,293; 5571698; and 5,837,500. Additional display methodologies which may be used to identify a peptide capable of binding to a biological target of interest are described in U.S. Pat. No. 7,256,038, the disclosure of which is incorporated herein by reference.

Optionally, the display scaffold can include a protease cleavage site (different from the protease cleavage site of the cleavable linker) to allow for cleavage of a proprotein or candidate proprotein from a surface of a host cell.

Methods of making a proprotein libraries and/or candidate proprotein libraries comprises: (a) constructing a set of recombinant DNA vectors as described below that encode a plurality of proproteins and/or candidate proproteins; (b) transforming host cells with the vectors of step (a); and (c) culturing the host cells transformed in step (b) under conditions suitable for expression and display of the fusion polypeptides.

Constructs Encoding Candidate Proproteins and Candidate Proprotein Components

The disclosure further provides vectors and nucleic acid constructs which include sequences coding for proproteins and/or candidate proproteins. Suitable nucleic acid constructs include, but are not limited to, constructs which are capable of expression in prokaryotic or eukaryotic cells. Expression constructs are generally selected so as to be compatible with the host cell in which they are to be used. In certain embodiments, the vector encodes a protein and a peptide mask or a protein, a peptide mask, and a cleavable linker.

For example, non-viral and/or viral constructs vectors may be prepared and used, including plasmids, which provide for replication of proprotein- or candidate proprotein-encoding DNA and/or expression in a host cell. The choice of vector will depend on the type of cell in which propagation is desired and the purpose of propagation. Certain constructs are useful for amplifying and making large amounts of the desired DNA sequence. Other vectors are suitable for expression in cells in culture. The choice of appropriate vector is well within the skill of the art. Many such vectors are available commercially. Methods for generating constructs can be accomplished using methods well known in the art.

In order to effect expression in a host cell, the polynucleotide encoding a proprotein or candidate proprotein is operably linked to a regulatory sequence as appropriate to facilitate the desired expression properties. These regulatory sequences can include promoters, enhancers, terminators, operators, repressors, and inducers. Expression constructs generally also provide a transcriptional and translational initiation region as may be needed or desired, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Constructs, including expression constructs, can also include a selectable marker operative in the host to facilitate, for example, growth of host cells containing the construct of interest. Such selectable marker genes can provide a phenotypic trait for selection of transformed host cells such as dihydrofolate reductase or neomycin resistance for eukaryotic cell culture.

Production of Nucleic Acid Sequences Encoding Candidate Proproteins

Production of candidate proproteins for use in the screening methods can be accomplished using methods known in the art. Polypeptide display, single chain antibody display, antibody display and antibody fragment display are methods well know in the art. In general, an element of a proprotein e.g., peptide mask, to be varied in the candidate proprotein library is selected for randomization. The candidate proproteins in the library can be fully randomized, partially randomized or biased in their randomization, e.g. in nucleotide/residue frequency generally or in position of amino acid(s) within an element. For example, the proprotein element (e.g., candidate peptide mask) can be partially randomized so as to provide for only a subset of amino acids at a selected position (e.g., to provide for a flexible linker at a selected position in the amino acid sequence, to provide for an amino acid residue of a desired characteristic (e.g., hydrophobic, polar, positively charged, negatively charged, etc.). In another example, the proprotein element (e.g., candidate peptide mask) can be partially randomized so that one or more residues within the otherwise randomized amino acid sequence is selected and held as invariable among a population or subpopulation of proprotein library members (e.g., so as to provide a cysteine at a desired position within the candidate peptide mask).

Methods of Screening for Proproteins and Components Thereof

Methods of Screening for Peptide Masks

Generally, the method for screening for peptide masks and peptide masks having a desired masking phenotype is accomplished through a positive screening step (to identify members that bind the functional protein) and a negative screening step (to identify members that do not bind the functional protein). The negative screening step can be accomplished by, for example, depleting from the population members that bind the functional protein in the absence of the peptide mask. It should be noted that the library screening methods described herein can be initiated by conducting the negative screening first to select for candidates that do not bind the functional protein and then conducting the positive screening (i.e., exposing library of replicable biological entities displaying candidate peptide masks to a functional protein and selecting for members which bind the functional protein.).

The positive and negative screening steps can be conveniently conducted using flow cytometry to sort candidate masks based on binding of a detectably labeled functional protein. One "round" or "cycle" of the screening procedure involves both a positive selection step and a negative selection step. The methods may be repeated for a library such that multiple cycles (including complete and partial cycles, e.g., 1.5 cycles, 2.5 cycles, etc.) are performed. In this manner, members of the plurality of candidate masks that exhibit binding to the functional protein of interest may be enriched in the resulting population.

Proprotein Mask Efficiency Assay: Choosing an effective peptide mask is not necessarily based solely on affinity but can include an empirical measure of 'masking efficiency.' Two exemplary assays can be used. The first is the measurement of the affinity of a Proprotein binding to a cell surface displaying a candidate peptide mask by, for example, FACS. In the second assay the ability of a peptide mask to inhibit Proprotein binding to its binding partner at therapeutically relevant concentrations and times can be measured. For this second method, an immunoabsorbant assay (MEA, Mask Efficiency Assay) to measure the time-dependent binding of proprotein binding to its binding partner has been developed.

Choosing an effective peptide mask cannot be based solely on affinity but must include an empirical measure of masking efficiency. To do this we have used two assays. The first is the measurement of the affinity of protein binding to the cell surface displayed peptide mask by FACS. In the second assay we measure the ability of a peptide mask to inhibit proprotein binding to its target at therapeutically relevant concentrations and times. To do this we developed an immunoabsorbant assay (MEA, Masking efficiency assay) to measure the time dependent binding partner displacement of the peptide mask in the Proprotein context.

In general, the screening methods are conducted by first generating a nucleic acid library encoding a plurality of candidate masks in a display scaffold, which is in turn introduced into a display scaffold for expression on the surface of a replicable biological entity.

Prior to the screening method, it may be desirable to enrich for cells expressing an appropriate peptide display scaffold on the cell surface. The optional enrichment allows for removal of cells from the cell library that (1) do not express peptide display scaffolds on the cell outer membrane or (2) express non-functional peptide display scaffolds on the cell outer membrane. By "non-functional" is meant that the peptide display scaffold does not properly display a candidate mask, e.g., as a result of a stop codon or a deletion mutation.

Enrichment for cells can be accomplished by growing the cell population and inducing expression of the peptide display scaffolds. The cells are then sorted based on, for example, detection of a detectable signal or moiety incorporated into the scaffold or by use of a detectably-labeled antibody that binds to a shared portion of the display scaffold or the proprotein. These methods are described in greater detail in U.S. Pat. No. 7,256,038 and U.S. Patent Application Publication No: 2007/0065878, published Mar. 22, 2007 and are incorporated by reference in their entirety.

Methods of Screening for Protease Substrates for Use as Cleavable Linkers

In general, the method for screening for candidate substrates to achieve the desired activatable phenotype for the proprotein is accomplished through a positive screening step (to identify members cleave the substrate following exposure to enzyme) and a negative screening step (to identify members that do not cleave the substrate when exposed to enzyme). The negative screening step can be accomplished by, for example, depleting from the population members that cleave the substrate absence of the protease. It should be noted that the library screening methods described herein can be initiated by conducting the negative screening first to select for candidates that do not cleave the substrate in the absence of enzyme treatment, and then conducting the positive screening (i.e., treating with enzyme and selecting for members which cleave the substrate.

The positive and negative screening steps can be conveniently conducted using flow cytometry to sort candidate substrates based on cleavage. One "round" or "cycle" of the screening procedure involves both a positive selection step and a negative selection step. The methods may be repeated for a library such that multiple cycles (including complete and partial cycles, e.g., 1.5 cycles, 2.5 cycles, etc.) are performed. In this manner, members of the plurality of candidate substrates that exhibit the activating characteristics may be enriched in the resulting population.

In general, the screening methods are conducted by first generating a nucleic acid library encoding a plurality of candidate substrates in a display scaffold, which is in turn introduced into a display scaffold for expression on the surface of a replicable biological entity.

Prior to the screening method, it may be desirable to enrich for cells expressing an appropriate peptide display scaffold on the cell surface. The optional enrichment allows for removal of cells from the cell library that (1) do not express peptide display scaffolds on the cell outer membrane or (2) express non-functional peptide display scaffolds on the cell outer membrane. By "non-functional" is meant that the peptide display scaffold does not properly display a candidate substrate, e.g., as a result of a stop codon or a deletion mutation.

Enrichment for cells can be accomplished by growing the cell population and inducing expression of the peptide display scaffolds. The cells are then sorted based on, for example, detection of a detectable signal or moiety incorporated into the scaffold or by use of a detectably-labeled antibody that binds to a shared portion of the display scaffold or the proprotein. These methods are described in greater detail in U.S. Pat. No. 7,256,038 and U.S. Patent Application Publication No: 2007/0065878, published Mar. 22, 2007 and are incorporated by reference in their entirety.

Methods of Screening for Activatable Proproteins

In general, the method for screening for candidate proproteins having a desired activatable phenotype is accomplished through a positive screening step (to identify members that bind a binding partner following exposure to enzyme) and a negative screening step (to identify members that do not bind a binding partner when not exposed to enzyme). The negative screening step can be accomplished by, for example, depleting from the population members that bind the binding partner in the absence of the protease. It should be noted that the library screening methods described herein can be initiated by conducting the negative screening first to select for candidates that do not bind labeled binding partner in the absence of enzyme treatment (i.e., do not bind labeled binding partner when not cleaved), and then conducting the positive screening (i.e., treating with enzyme and selecting for members which bind labeled binding partner in the cleaved state).

The positive and negative screening steps can be conveniently conducted using flow cytometry to sort candidate proproteins based on binding of a detectably labeled binding partner. One "round" or "cycle" of the screening procedure involves both a positive selection step and a negative selection step. The methods may be repeated for a library such that multiple cycles (including complete and partial cycles, e.g., 1.5 cycles, 2.5 cycles, etc.) are performed. In this manner, members of the plurality of candidate proproteins that exhibit the activating characteristics of a proprotein may be enriched in the resulting population.

In general, the screening methods are conducted by first generating a nucleic acid library encoding a plurality of candidate proproteins in a display scaffold, which is in turn introduced into a display scaffold for expression on the surface of a replicable biological entity.

Prior to the screening method, it may be desirable to enrich for cells expressing an appropriate peptide display scaffold on the cell surface. The optional enrichment allows for removal of cells from the cell library that (1) do not express peptide display scaffolds on the cell outer membrane or (2) express non-functional peptide display scaffolds on the cell outer membrane. By "non-functional" is meant that the peptide display scaffold does not properly display a candidate proprotein, e.g., as a result of a stop codon or a deletion mutation.

Enrichment for cells can be accomplished by growing the cell population and inducing expression of the peptide display scaffolds. The cells are then sorted based on, for example, detection of a detectable signal or moiety incorporated into the scaffold or by use of a detectably-labeled antibody that binds to a shared portion of the display scaffold or the proprotein. These methods are described in greater detail in U.S. Pat. No. 7,256,038 and U.S. Patent Application Publication No: 2007/0065878, published Mar. 22, 2007 and are incorporated by reference in their entirety.

Detectable Labels

As used herein, the terms "label", "detectable label" and "detectable moiety" are used interchangeably to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. The term "fluorescer" refers to a substance or a portion thereof which is capable of exhibiting fluorescence in the detectable range. Exemplary detectable moieties suitable for use as labels include, affinity tags and fluorescent proteins.

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Screening Methods

Any suitable method that provides for separation and recovery of proproteins of interest may be utilized. For example, a cell displaying a proprotein of interest may be separated by FACS, immunochromatography or, where the detectable label is magnetic, by magnetic separation. As a result of the separation, the population is enriched for cells that exhibit the desired characteristic, e.g., exhibit binding to binding partner following cleavage or have decreased or no detectable binding to binding partner in the absence of cleavage.

For example, selection of candidate proproteins having bound detectably labeled binding partner can be accomplished using a variety of techniques known in the art. For example, flow cytometry (e.g., FACS®) methods can be used to sort detectably labeled candidate proproteins from unlabeled candidate proproteins. Flow cytometry methods can be implemented to provide for more or less stringent requirements in separation of the population of candidate proproteins, e.g., by modification of gating to allow for "dimmer" or to require "brighter" cell populations in order to be separated into the second population for further screening.

In another example, immunoaffinity chromatography can be used to separate target-bound candidate proproteins from those that do not bind target. For example, a support (e.g., column, magnetic beads) having bound anti-target antibody can be contacted with the candidate proproteins that have been exposed to protease and to binding partner. Candidate proproteins having bound target bind to the anti-target antibody, thus facilitating separation from candidate proproteins lacking bound target. Where the screening step is to provide for a population enriched for uncleaved candidate proproteins that have relatively decreased target binding or no detectable target binding (e.g., relative to other candidate proproteins), the subpopulation of interest is those members that lack or have a relatively decreased detectably signal for bound target. For example, where an immunoaffinity technique is used in such negative selection for bound target, the subpopulation of interest is that which is not bound by the anti-target support.

Therapeutic Uses of Proproteins

Proproteins described herein can be selected for use in methods of treatment of suitable subjects according to the cleavable linker-protein combination provided. Exemplary non-limiting uses for proproteins are for hepatitis C, cancer, and angiogenesis. For example, a patient suffering from a condition (e.g., such as described above) can be administered a therapeutically effective amount of a proprotein.

Use of a proprotein can allow for decreased dosing frequency compared to the unmodified or parent protein.

The proprotein can be administered by any suitable means, including parenteral, subcutaneous, intraperitoneal, intrapulmonary, and intranasal, and, if desired for local injection (e.g., at the site of a solid tumor). Parenteral administration routes include intramuscular, intravenous, intraarterial, intraperitoneal, or subcutaneous administration.

The appropriate dosage of proprotein will depend on the type of disease to be treated, the severity and course of the disease, the patient's clinical history and response to the proprotein, and the discretion of the physician. Proproteins can suitably be administered to the patient at one time or over a series of treatments.

Depending on the type and severity of the disease, about 1 ug/kg to 100 mg/kg, or at least 1 ug/kg, 5 ug/kg, 10 ug/kg, 50 ug/kg, 100 ug/kg, 250 ug/kg, 500 ug/kg, 1 mg/kg, 5 mg/kg, 10 mg/kg, 20 mg/kg, 25 mg/kg, 50 mg/kg, or 100 mg/kg of proprotein can serve as an initial candidate dosage for administration to the patient, whether, for example, by one or more separate administrations, or by continuous infusion. A typical daily dosage might range from about 1 ug/kg to 100 mg/kg or more, depending on factors such as those mentioned herein. For repeated administrations over several days or longer, depending on the condition, the treatment is sustained until a desired suppression of disease symptoms occurs. However, other dosage regimens may be useful.

The proprotein composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the proprotein, the method of administration, the scheduling of administration, and other factors known to medical practitioners. The "therapeutically effective amount" of a proprotein to be administered will be governed by such considerations, and is the minimum amount necessary to prevent, ameliorate, or treat a disease or disorder.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject or mammal.

Proproteins can substantially reduce the known side-effects and improve the efficacy of know drugs, for example those known drugs listed in Table 1.

Proproteins can be used in combination (e.g., in the same formulation or in separate formulations) with one or more additional therapeutic agents or treatment methods ("combination therapy"). A proprotein can be administered in admixture with another therapeutic agent or can be administered in a separate formulation. Therapeutic agents and/or treatment methods that can be administered in combination with a proprotein, and which are selected according to the condition to be treated, include surgery (e.g., surgical removal of cancerous tissue), radiation therapy, bone marrow transplantation, chemotherapeutic treatment, certain combinations of the foregoing, and the like.

Exemplary Embodiments

The compositions and proproteins provided here in can be useful for a variety of purposes including therapeutics and diagnostics.

Use of Proproteins that Modulate Interferon Signaling Pathways in the Treatment of Liver Conditions Where the proprotein contains a functional protein that modulates interferon signaling, for example when the functional protein is IFN-α, the proprotein finds use in treatment of conditions such as Hepatitis C viral infection and liver cancers (for e.g. hepatocellular cancer).

An IFN-α proprotein can be used as a therapeutic and/or diagnostic agent. Such a proprotein would be activatable by a cleaving agent (e.g., enzyme, such as a matriptase, HCV-NS3/4, plasmin or other enzyme as discussed herein) which co-localizes at the liver. Exemplary proproteins for the treatment of Hepatitis C infection are Matriptase-activated pro-IFN-α and HCV-NS3/4-activated pro-IFN-α.

An exemplary proprotein useful for the treatment and/or diagnosis of Hepatitis C infection can be a PEGylated pro-interferon alfa-2a or an enzyme-activatable masked PEGylated interferon alfa-2a, such as a proprotein form of PEGASYS® or an enzyme-activatable masked PEGASYS®. For example, the proprotein can be Matriptase or HCV NS3/4 activatable. Other exemplary proteins available for use in interferon-related proprotein compositions are presented in Table 1.

Cancer Inhibiting Proproteins

Cancer inhibiting proproteins find use in treatment of several types of tumors.

Where the proprotein contains a functional protein that modulates the Notch pathway, the proprotein finds use in treatment of conditions such as cancers, for example breast cancer and prostate cancer. In one embodiment the proprotein can contain an enzyme-activatable soluble Notch receptor or Notch receptor fragment. Exemplary enzyme-activatable Notch containing proproteins for the treatment of various cancers include but are not limited to a legumain-activatable pro-Notch1 for the treatment of colorectal cancer, legumain-activatable pro-Notch1 for the treatment of head and neck cancer, legumain-activatable pro-Notch1 for the treatment of pancreatic cancer, legumain-activatable pro-Notch1 for the treatment of lung cancer, legumain-activatable pro-Notch1 for the treatment of ovarian cancer, PSA-activatable pro-Notch1 for the treatment of prostate cancer, plasmin-activatable pro-Notch1 for the treatment of triple negative breast cancer, plasmin-activatable pro-Notch1 for the treatment of colorectal cancer, plasmin-activatable pro-Notch1 for the treatment of head and neck cancer, plasmin-activatable pro-Notch1 for the treatment of pancreatic cancer, plasmin-activatable pro-Notch1 for the treatment of lung cancer, plasmin-activatable pro-Notch1 for the treatment of ovarian cancer, uPA-activatable pro-Notch1 for the treatment of triple negative breast cancer, uPA-activatable pro-Notch1 for the treatment of colorectal cancer, uPA-activatable pro-Notch1 for the treatment of head and neck cancer, uPA-activatable pro-Notch1 for the treatment of pancreatic cancer, uPA-activatable pro-Notch1 for the treatment of lung cancer, or a uPA-activatable pro-Notch1 for the treatment of ovarian cancer.

Angiogenesis inhibiting proproteins find use in treatment of solid tumors in a subject (e.g., human), particularly those solid tumors that have an associated vascular bed that feeds the tumor such that inhibition of angiogenesis can provide for inhibition or tumor growth. Anti-angiogenesis proproteins also find use in other conditions having one or more symptoms amenable to therapy by inhibition of abnormal angiogenesis.

In general, abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularization, especially diabetic blindness, retinopathies, primarily diabetic retinopathy or age-induced macular degeneration and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive neplirosclerosis; various imflammatory diseases, such as arthritis, especially rheumatoid arthritis, inflammatory bowel disease, psorsasis, sarcoidosis, arterial arteriosclerosis and diseases occurring after transplants, endometriosis or chronic asthma and other conditions that will be readily recognized by the ordinarily skilled artisan. The new blood vessels can feed the diseased tissues, destroy normal tissues, and in the case of cancer, the new vessels can allow tumor cells to escape into the circulation and lodge in other organs (tumor metastases).

Proprotein-based anti-angiogenesis therapies can also find use in treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases that may be treated using anti-angiogenic proproteins as described herein include angiofibroma (abnormal blood of vessels which are prone to bleeding), neovascular glaucoma (growth of blood vessels in the eye), arteriovenous malformations (abnormal communication between arteries and veins), non-union fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

Amounts of proproteins for administration to provide a desired therapeutic effect will vary according to a number of factors such as those discussed above. In general, in the context of cancer therapy, a therapeutically effective amount of a proprotein is an amount that that is effective to inhibit angiogenesis, and thereby facilitate reduction of, for example, tumor load, atherosclerosis, in a subject by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood or serum; and the like.

In some embodiments, the methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, "effective amounts" of a proprotein are amounts that are sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be tumor growth rate in a genetically identical animal not treated with the agent. In non-experimental systems, a suitable control may be the tumor load or tumor growth rate present before administering the agent. Other suitable controls may be a placebo control.

Whether growth of a tumor is inhibited can be determined using any known method, including, but not limited to, an in vivo assay for tumor growth; an in vitro proliferation assay; a 3H-thymidine uptake assay; and the like.

Biodistribution Considerations

The therapeutic potential of the compositions described herein allow for greater biodistribution and bioavailability of the modified functional protein. The compositions described herein provide a protein therapeutic having an improved bioavailability wherein the affinity of binding of the functional protein therapeutic to its binding partner is lower in a healthy tissue when compared to a diseased tissue. A pharmaceutical composition comprising a functional protein coupled to a peptide mask can display greater affinity to its binding partner in a diseased tissue than in a healthy tissue. In preferred embodiments, the affinity in the diseased tissue is 5-10,000,000 times greater than the affinity in the healthy tissue. In an exemplary embodiment, the affinity in the diseased tissue is about 10,000 times greater than the affinity in the healthy tissue.

Generally stated, the present disclosure provides for a proprotein therapeutic having an improved bioavailability wherein the affinity of binding of the therapeutic to its binding partner is lower in a first tissue when compared to the binding of the therapeutic to its binding partner in a second tissue. By way of example in various embodiments, the first tissue is a healthy tissue and the second tissue is a diseased tissue; the first tissue is an early stage tumor and the second tissue is a late stage tumor; the first tissue is a benign tumor and the second tissue is a malignant tumor; the first tissue is liver tissue and the second tissue is non liver tissue; the first tissue is uninfected liver tissue and the second tissue is virally infected liver tissue; or the first tissue and second tissues are spatially separated. In the specific example where the first tissue is a healthy tissue and the second tissue is a diseased tissue, the diseased tissue can be a tumor-containing tissue, an inflamed tissue, or a viral infected tissue. In another specific example, the first tissue is epithelial tissue and the second tissue is breast, head, neck, lung, pancreatic, nervous system, liver, prostate, urogenital, or cervical tissue.

In one exemplary embodiment, the invention provides for a proprotein therapeutic for the treatment of Hepatitis C having an improved bioavailability. Such a proprotein contains a functional protein coupled to a peptide mask and a cleavable linker, wherein the affinity of binding of the functional protein therapeutic to its target is higher in liver tissue when compared to the binding of the functional protein therapeutic to its target in a non-liver tissue, wherein target is present in both tissues. Furthermore, the proprotein can contain a cleavable linker comprising a substrate specific for an enzyme upregulated in Hepatitis C or a hepatocellular cancer affected tissue, for example a substrate for a matriptase or HCV NS3/4 enzyme.

Pharmaceutical Compositions

Proproteins of the present disclosure can be incorporated into pharmaceutical compositions containing, for example, a therapeutically effective amount of an activatable masked protein of interest and a carrier pharmaceutically acceptable excipient (also referred to as a pharmaceutically acceptable carrier). Many pharmaceutically acceptable excipients are known in the art, are generally selected according to the route of administration, the condition to be treated, and other such variables that are well understood in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. Pharmaceutical compositions can also include other components such as pH adjusting and buffering agents, tonicity adjusting agents, stabilizers, wetting agents and the like. In some embodiments, nanoparticles or liposomes carry a pharmaceutical composition comprising a proprotein.

Suitable components for pharmaceutical compositions of proproteins can be guided by pharmaceutical compositions that may be available for the functional protein to be masked.

In general, pharmaceutical formulations of one or more proproteins are prepared for storage by mixing the proprotein having a desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations to be used for in vivo administration must be sterile. This is readily accomplished by filtration through sterile filtration membranes. Pharmaceutical formulations may also contain more than one active compound as necessary for the particular indication being treated, where the additional active compounds generally are those with activities complementary to the proprotein.

The pharmaceutical formulation can be provided in a variety of dosage forms such as a systemically or local injectable preparation. The components can be provided in a carrier such as a microcapsule, e.g., such as that prepared by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

Sustained-release preparations are also within the scope of proprotein-containing formulations. Exemplary sustained-release preparations can include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Proproteins can be conjugated to delivery vehicles for targeted delivery of an active agent that serves a therapeutic purpose. For example, proproteins can be conjugated to nanoparticles or liposomes having drugs encapsulated therein or associated therewith. In this manner, specific, targeted delivery of the drug can be achieved. Methods of linking polypeptides to liposomes are well known in the art and such methods can be applied to link proproteins to liposomes for targeted and or selective delivery of liposome contents. By way of example, polypeptides can be covalently linked to liposomes through thioether bonds. PEGylated gelatin nanoparticles and PEGylated liposomes have also been used as a support for the attachment of polypeptides, e.g., single chain antibodies. See, e.g., Immordino et al. (2006) Int J Nanomedicine. September; 1(3): 297-315, incorporated by reference herein for its disclosure of methods of conjugating polypeptides, e.g., antibody fragments, to liposomes.

In certain embodiments the proproteins of the present are further conjugated to protective chains such as PEG or mPEG, or any alkyl-PEG. Such conjugates would be less susceptible to non specific in vivo hydrolytic cleavage, have enhanced in vivo half life, and reduce the immunogenicity of the functional protein while maintaining biological activity.

Non-Therapeutic Uses of Proproteins

Proproteins can also be used in diagnostic and/or imaging methods. For example, proproteins having an enzymatically cleavable linker can be used to detect the presence or absence of an enzyme that is capable of cleaving the cleavable linker. Such proproteins can be used in diagnostics, which can include in vivo detection (e.g., qualitative or quantitative) of enzyme activity accompanied by presence of a binding partner of interest through measured accumulation of activated proproteins in a given tissue of a given host organism.

For example, the cleavable linker can be selected to be an enzyme substrate for an enzyme found at the site of a tumor, at the site of a viral or bacterial infection at a biologically confined site (e.g., such as in an abscess, in an organ, and the like). Using methods familiar to one skilled in the art, a detectable label (e.g., a fluorescent label) can be conjugated to the functional protein or other region of the proprotein. Using a functional protein specific to a disease target, along with an enzyme whose activity is elevated in the disease tissue of interest, proproteins can exhibit increased rate of binding to disease tissue relative to tissues where the cleavable linker-specific enzyme is not present at a detectable level or is present at a lower level than in disease tissue. Because the enzyme specific for the cleavable linker is not present at a detectable level (or is present at lower levels) in non-diseased tissues, accumulation of activated proprotein in the diseased tissue is enhanced relative to non-disease tissues.

Non-limiting examples of detectable labels that can be used as diagnostic agents include imaging agents containing radioisotopes such as indium or technetium; contrasting agents for MRI and other applications containing iodine, gadolinium or iron oxide; enzymes such as horse radish peroxidase, alkaline phosphatase, or B-galactosidase; fluorescent substances and fluorophores such as GFP, europium derivatives; luminescent substances such as N-methylacrydium derivatives or the like.

EXAMPLES

Example 1

Screening of a Peptide Library and Identification of Peptide Masks Specific for IFN-α

Figure 2:
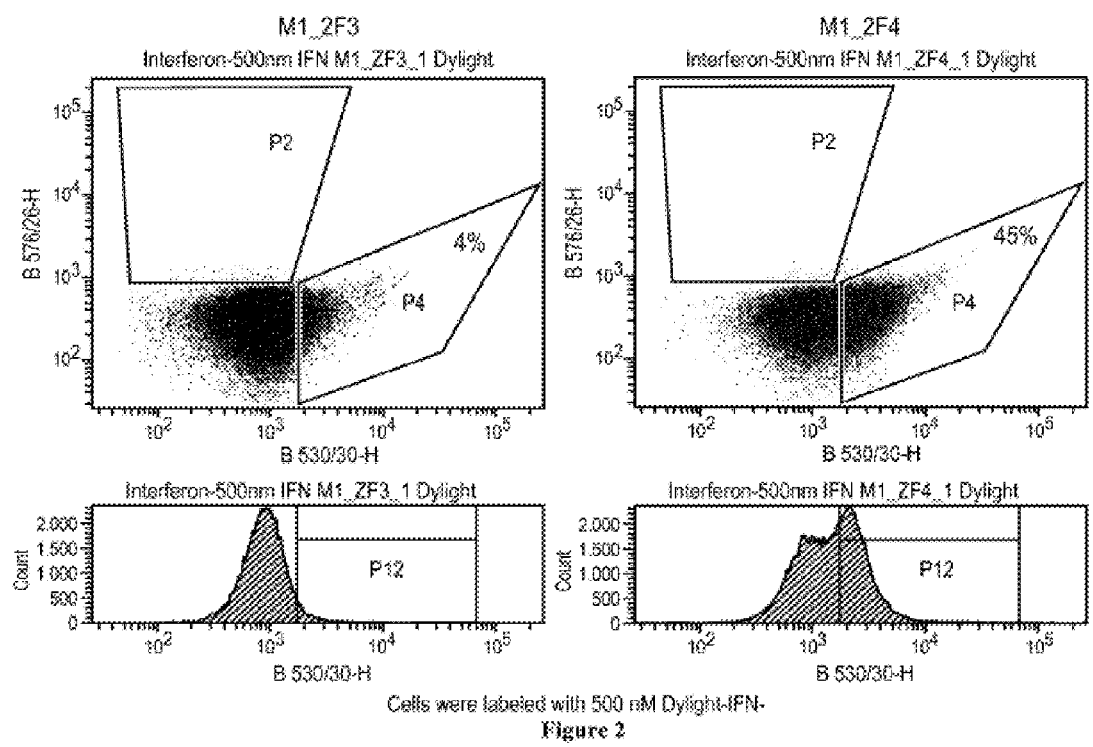
FIG. 2 depicts enrichment of IFN-α binding peptides for use as masks, as assayed by FACS.

In order to identify peptide masks for Interferon-α (IFN-α), a peptide library was screened. IFN-α was used to screen a random 15X peptide library, where X is any amino acid, with a total diversity of $5 \times 10^{10}$. The screening consisted of an initial round of MACS (magnetic activated cell sorting) followed by four rounds of FACS (fluorescence activated cell sorting). The initial MACS and three rounds of FACS were done with biotinylated IFN-α at a concentration of 500 nM. For MACS, approximately $1 \times 10^{11}$ cells were screened for binding and $3.4 \times 10^7$ cells were collected. NeutrAvidin-PE was used as a fluorescent probe for the initial FACS rounds. The fourth round of FACS selections was done with 500 nM Dylight labeled IFN-α (Dylight-IFN-α). The third and fourth round of FACS sorting is shown labeled with Dylight-IFN-α in FIG. 2.

Exemplary binding peptides are shown in Table 3 below.

TABLE 3

| | IFN-α Binding peptides |
|---|---|
| 47 | IAYLEYYEHLHMAYG (SEQ ID NO: 13) |
| 49 | TDVDYYREWCWTQVS (SEQ ID NO: 14) |
| 49CS | TDVDYYREWSWTQVS (SEQ ID NO: 15) |

Example 2

Construction and Expression of Pro-IFN-α

Construction of Interferon-α Under PhoA Control:

The human Interferon-α gene was purchased from Open Biosystems. IFN-α was cloned into the Phagmid X (PhoA driven bacterial expression vector) in the following manner. IFN-α was amplified using primers CX0573 and CX0566. The PhoA promoter was amplified from the Phagmid X using the primers CX0571 and CX0572. These two overlapping products were combined into one polymerase chain reaction and amplified using the primers CX0581 and CX0572. The final product was cloned into Phagmid X using the HindIII and EcoRI restriction sites.

Construction of Masked Interferon-α Under PhoA Control:

A mask accepting vector with GGS linker and no protease substrate was constructed as follows. The overlapping forward primers CX0577, CX0579, and CX0580 were used with the reverse primer CX0566 to amplify the IFN-α cDNA with a GGS linker and mask accepting site. This product was cloned into the STII containing Phagmid X vector using the BamHI and EcoRI restriction sites. This vector was then used as a template for the construction of the MMP-9 substrate containing vector. Two overlapping PCR products were amplified using the primer pair CX0573/CX0612 and CX0611/CX0566. These two products were combined into a PCR, amplified with the primers CX0573 and CX0566, and cloned into the Phagmid X using the HindIII and EcoRI restriction sites.

The IFN-α peptide masks were cloned into the MMP-9 Pro-protein vector using the SfiI and XhoI sites. The 47 and 49 peptide masks (Table 3) were then amplified using CX0289/CX0448 and CX0582/CX0583, respectively, using the ecpX3.0 clones that encoded the bacterial displayed masking peptide indicated. The CX0582/CX0583 primer pair mutated the Cys in the 49 masking peptide to a Ser creating the masking peptide 49CS (Table 3).

TABLE 4

Primer Sequences for Construction of Masked IFN-α

CX0289 gctttcaccgcaggtacttccgtagctggccagtctggcc (SEQ ID NO: 16)

CX0448 gagttttgtcggatccaccagagccaccgctgccaccgct cgagcc (SEQ ID NO: 17)

CX0566 gcgttatcccgaattcctagtggtgatggtgatgatgttc cttacttcttaaactttcttgc (SEQ ID NO: 18)

CX0571 agtgaattgtaagctttggagattatcgtcac (SEQ ID NO: 19)

CX0572 caggctgtgggtttgaggcagatcacacattttattttct ccatgtacaaatac (SEQ ID NO: 20)

CX0573 tgtgatctgcctcaaacccacagcctg (SEQ ID NO: 21)

CX0577 ggtggcagcatgtgtgatctgcctcaaacccac (SEQ ID NO: 22)

CX0579 ggctcgagcggcggctccggcggtagcggtggctctggtg gcagcatgtgtgatctgc (SEQ ID NO: 23)

CX0580 tgcgtatgcaggatccggccagtctggccagcaagtcatt ctgagaagcggctcgagcggcggctcc (SEQ ID NO: 24)

CX0582 ttccgtagctggccagtctggccagacggacgtggactat tatagggagtggtc (SEQ ID NO: 25)

CX0583 gctgccaccgctcgagcctgatacttgagtccaggaccac tccctataatagtc (SEQ ID NO: 26)

CX0611 catgccactgggcttcctgggtccgggtggcagcatgtgt gatc (SEQ ID NO: 27)

CX0612 ccaggaagcccagtggcatgtgcacggagccgccgctcga gccgc (SEQ ID NO: 28)

Interferon-α Expression and Inclusion Body Purification:

Interferon and pro-Interferon-α constructs were expressed in the cytoplasm of *E. coli* under control of the PhoA promoter. Inclusion bodies were purified as follows: bacteria from 1 Liter of fresh overnight culture were grown in phosphate limiting media (per Liter=3.57 g $(NH_4)_2SO_4$, 0.71 g Na citrate-$2H_2O$, 1.07 g KCl, 5.36 g Yeast Extract, 5.36 g HycaseSF-Sheffield, pH adjusted to 7.3 with KOH, volume adjusted to 872 ml, autoclaved. Supplemented post-autoclave with 110 peptide mask MOPS pH7.3, 0.5% glucose, 7 uM $MgSO_4$ and 50 ug/ml carbenicillin). The culture was pelleted and then lysed with 20 mL of BPERII (Pierce). The lysate was centrifuged at 14,000×g and the supernatant discarded. The pellet was then resuspended in a 1:10 BPERII to water solution, 720 Ku of lysozyme and 40 Ku of DNAseI were added, and lysate was incubated at room temperature for 1 hr. The lysate was centrifuged at 14,000×g and the inclusion bodies (IBs) were washed an additional time in 1:20 BPERII. Pelleted inclusion bodies were stored at −20° C. until further use.

Interferon-α Purification and Refolding:

Inclusion bodies isolated from 1 Liter of culture were solubilized in 20 mL of IB solubilization buffer (50 peptide mask Tris, 8 M Urea, 1 peptide mask TCEP, pH 8.0). Insoluble protein was removed by centrifugation before adding the solubilized protein to a Ni-NTA column (Qiagen). The bound protein was washed with 5 mL of IB solubilization buffer followed by 5 mL of IB solubilization buffer with 5 peptide mask β-mercaptoethanol instead of TCEP. Purified protein was eluted with Elution Buffer (0.2M Glycine, 8M Urea, pH 3.0) and added in a drop-wise fashion to 100 mL of stirring chilled Refolding Buffer (0.75 M Arginine, 0.055% PEG (w/v), 2.2 mM $CaCl_2$, 2.2 mM $MgCl_2$, 55 mM Tris, 0.44 mM KCL, 10.56M NaCl, 4 mM reduced glutathione, 0.4 mM oxidized glutathione, pH 7.5). Refolding was allowed to proceed overnight at 4° C. with constant slow stirring. Following refolding, the protein was dialyzed extensively into PBS before being applied to a Ni-NTA column. Bound protein was washed with PBS and Eluted with Imidizole Elution Buffer (50 mM Tris, 300 mM NaCl, 250 mM Imidizole). Purified protein was concentrated and buffer exchanged to PBS, pH 7.4 using an Amicon Centrifuge concentrator.

Example 3

Analysis of Pro-IFN-α Masking and Unmasking

To demonstrate masking of the Pro-IFN-α, the refolded proteins, 47-MMP-IFN-α or 49-MMP-IFN-α were diluted 1:1 in MMP-9 digestion buffer (50 mM Tris, 20 mM NaCl, 2 mM $CaCl_2$, 100 μM $ZnCl_2$, pH 6.82) and half of the sample was digested with about 35 Units of MMP-9 for 3 hrs at 37° C. Subsequently, 60, 40, 20, and 6.6 μL of the digested and undigested material was added to 400 μL of 2% non-fat dry milk in PBS-T (PBS, 0.05% TWEEN, pH 7.4) and analyzed by ELISA, as described:

Interferon ELISA's: A recombinant Interferon receptor 1-Fc (IFNR1-Fc) fusion protein (R & D Systems) was used to detect IFN-α binding. Briefly, the receptor was absorbed to ELISA plates at a concentration of 5 μg/mL in PBS for 1 hr at RT. Wells were then blocked with 2% non-fat dry milk in PBS-T for 1 hr at RT. Interferon-α was added at three concentrations, 60, 40, 20 and 6.6 nM, to the wells in 100 μL of 2% non-fat dry milk in PBS-T. Wells were washed 3 times with PBS-T and the interferon was detected with an anti-$His_6$ (SEQ ID NO: 84) monoclonal antibody (Invitrogen) at a titer of 1:1000 mixed with an anti-muFc-HRP conjugate (Fisher) at a titer of 1:2000 in a 100 uL of 2% non-fat dry milk in PBS-T per well. The ELISA was developed with 100 μL of TMB (Pierce) following the manufacturer's protocol (FIG. 3). FIG. 3 shows the binding of two Pro-Interferon-α molecules, Pro-Interferon-α-47 (Tables 7 and 8) and Pro-Interferon-α-49CS (Tables 8 and 9), before and after treatment with MMP-9. The first four bars of FIG. 3 (small checked) show that before treatment Pro-Interferon-α-49CS cannot bind to IFNRA, however after MMP-9 removal of Mask 49CS the resulting IFN-α (second set of four bars, Figure, large checked) molecule binds to IFNRA. In contrast Mask 47 weakly blocks IFN-α binding to IFNRA when incorporated into Pro-Interferon-α-47 (FIG. 3, third set of bars, horizontal lines) which is restored by treatment with MMP9 (FIG. 3, final four bars, vertical lines).

TABLE 5

| Nucleotide Sequence of Interferon-α |
|---|
| atgtgtgatctgcctcaaacccacagcctgggtagcaggaggaccttg |
| atgctcctggcacagatgaggagaatctctcttttctcctgcttgaag |
| gacagacatgactttggatttccccaggaggagtttggcaaccagttc |
| caaaaggctgaaaccatccctgtcctccatgagatgatccagcagatc |
| ttcaatctcttcagcacaaaggactcatctgctgcttgggatgagacc |
| ctcctagacaaattctacactgaactctaccagcagctgaatgacctg |
| gaagcctgtgtgatacaggggtgggggtgacagagactcccctgatg |
| aaggaggactccattctggctgtgaggaaatacttccaaagaatcact |
| ctctatctgaaagagaagaaatacagcccttgtgcctgggaggttgtc |
| agagcagaaatcatgagatcttttgtcaacaaacttgcaagaaagtt |
| taagaagtaaggaacatcaccatcatcaccat (SEQ ID NO: 29) |

TABLE 6

| Amino Acid Sequence of Interferon-α: Parentheses delineate the demarcations between the various sequence domains: (IFN-α)--(affinity tag) |
|---|
| (MCDLPQTHSLGSRRTLMLLAQMRRISLFSCLKDRHDFGFPQEEFGNQFQ |
| KAETIPVLHEM IQ QIFNLF STKD SSAAWDETLLDKFYTELYQ QLN |
| DLEACVIQGVGVTETPLMKEDSILAV RKYF QRITLYLKEKKY SP CA |
| WEVVRAEIMRSFSLSTNLQESLRSKE)(HHHHHH) |
| (SEQ ID NO: 30) |

TABLE 7

| Nucleotide Sequence of Pro-Interferon-α-47 |
|---|
| ggccagtctggccagattgcgtaccttgagtattatgagcacctacatat |
| ggcctacggctcgagcggcggctccgtgcacatgccactgggcttcctgg |
| gtccgggtggcagcatgtgtgatctgcctcaaacccacagcctgggtagc |

TABLE 7-continued

Nucleotide Sequence of Pro-Interferon-α-47 aggaggaccttgatgctcctggcacagatgaggagaatctctcttttctc ctgcttgaaggacagacatgactttggatttccccaggaggagtttggca accagttccaaaaggctgaaaccatccctgtcctccatgagatgatccag cagatcttcaatctcttcagcacaaaggactcatctgctgcttgggatga gaccctcctagacaaattctacactgaactctaccagcagctgaatgacc tggaagcctgtgtgatacaggggtggggtgacagagactccctgatg aaggaggactccattctggctgtgaggaaatacttccaaagaatcactct ctatctgaaagagaagaaatacagcccttgtgcctggaggttgtcagag cagaaatcatgagatcttttctttgtcaacaaacttgcaagaaagttta agaagtaaggaacatcaccatcatcaccat (SEQ ID NO: 31)

TABLE 8

Amino Acid Sequence of Pro-Interferon-α-47
Parentheses delineate the demarcations between the
various sequence domains: (Linker)--(Masking
Peptide)--(Linker)--(MMP-9 substrate)--(Linker)--
(IFN-α)--(Affinity tag)

(GQSGQ) (IAYLEYYEHLHMAY) (GSSGGS) (VHMPLGFLGP) (GGS)

(MCDLPQTHSLGSRRTLMLLAQM RRISLF SCLKDRHDFGFPQEEFGNQ

FQKAETIPVLHEMIQQIFNLF STKDSSAAWDETLLDKFYTELYQQLNDL

EACVIQGVGVTETPLMKEDSILAVRKYFQRITLYLKEKKYSPCAWE VVR

AEIMRSF SLSTNLQESLRSKE) (HHHHHH) (SEQ ID NO: 32)

TABLE 9

Nucleotide Sequence of Pro-Interferon-α-49CS ggccagtctggccagacggacgtggactattatagggagtggtcctggac tcaagtatcaggctcgagcggcggctccgtgcacatgccactgggcttcc tgggtccgggtggcagcatgtgtgatctgcctcaaacccacagcctggt agcaggaggaccttgatgctcctggcacagatgaggagaatctctctttt ctcctgcttgaaggacagacatgactttggatttccccaggaggagtttg gcaaccagttccaaaaggctgaaaccatccctgtcctccatgagatgatc cagcagatcttcaatctcttcagcacaaaggactcatctgctgcttggga tgagaccctcctagacaaattctacactgaactctaccagcagctgaatg acctggaagcctgtgtgatacaggggtggggtgacagagactccctg atgaaggaggactccattctggctgtgaggaaatacttccaaagaatcac tctctatctgaaagagaagaaatacagcccttgtgcctgggaggttgtca gagcagaaatcatgagatcttttctttgtcaacaaacttgcaagaaagt ttaagaagtaaggaacatcaccatcatcaccat (SEQ ID NO: 33)

TABLE 10

Amino Acid Sequence of Pro-Interferon-α-49CS
Parentheses delineate the demarcations between the
various sequence domains: (Linker)--(Masking
Peptide)--(Linker)--(MMP-9 substrate)--(Linker)--
(IFN-α)--(Affinity tag)

(GQSGQ) (TDVDYYREWSWTQVS) (GSSGGS) (VHMPLGFLGP) (GGS)

(MCDLPQTHSLGSRRTLMLLAQ MRRISLF SCLKDRHDFGFPQEEFGNQ

FQKAETIPVLHEMIQQIFNLFSTKDSSAAWDETL LDKFYTELYQQLNDL

EACVIQGVGVTETPLMKEDSILAVRKYFQRITLYLKEKKYSPCAW EVVR

AEIMRSF SLSTNLQESLRSKE) (HHHHHH) (SEQ ID NO: 34)

Example 4

Construction and Testing of a Matriptase or HCV NS3/4 Activatable IFN-α Proprotein Library Displaying Candidate Substrates and Peptide Masks In order to identify IFN-α proproteins having desired activating characteristics (i.e., decreased binding to its IFNRA receptor when in an uncleaved conformation relative to IFNRA receptor binding when in a cleaved conformation), candidate IFN-α proproteins having variable matriptase or HCV NS3/4 cleavable linkers and different variable amino acid sequences in the peptide masks and varying positions of the cysteine in the peptide mask were generated.

Consensus sequences for Matriptase and HCV NS3/4 are provided here in Tables 11-12.

TABLE 11

| Matriptase Consensus Sequences: |
|---|
| XXQAR(A/V)X (SEQ ID NO: 87) |
| AGPR (SEQ ID NO: 2) |

TABLE 12

| HCV NS3/4 Consensus Sequences |
|---|
| DEXXXC(A/S) (SEQ ID NO: 85) |
| DLXXXT(A/S) (SEQ ID NO: 86) |

Interferon-α purification and refolding: Inclusion bodies isolated from 1 Liter of culture were solubilized in 20 mL of IB solubilization buffer (50 peptide mask Tris, 8 M Urea, 1 peptide mask TCEP, pH 8.0). Insoluble protein was removed by centrifugation before adding the solubilized protein to a Ni-NTA column (Qiagen). The bound protein was washed with 5 mL of IB solubilization buffer followed by 5 mL of IB solubilization buffer with 5 peptide mask β-mercaptoethanol instead of TCEP. Purified protein was eluted with Elution Buffer (0.2M Glycine, 8M Urea, pH 3.0) and added in a drop-wise fashion to 100 mL of stirring chilled Refolding Buffer (0.75 M Arginine, 0.055% PEG (w/v), 2.2 mM $CaCl_2$, 2.2 mM $MgCl_2$, 55 mM Tris, 0.44 mM KCL, 10.56M NaCl, 4 mM reduced glutathione, 0.4 mM oxidized glutathione, pH 7.5). Refolding was allowed to proceed overnight at 4° C. with constant slow stirring. Following refolding, the protein was dialyzed extensively into PBS before being applied to a Ni-NTA column. Bound protein was washed with PBS and Eluted with Imidizole Elution Buffer (50 mM Tris, 300 mM NaCl, 250 mM Imidizole). Purified protein was concentrated and buffer exchanged to PBS, pH 7.4 using an Amicon Centrifuge concentrator.

To demonstrate masking of the Pro-IFN-α, the refolded proteins, Mask-Matriptase-IFN-α or Mask-HCV NS3/4-IFN-α were diluted 1:1 in digestion buffer (50 mM Tris, 20 mM NaCl, 2 mM $CaCl_2$, pH 7.2) and half of the sample was digested with about 20 nM of Matriptase or HCV NS3/4 for 3 hrs at 37° C. Subsequently, 60, 40, 20, and 6.6 μl, of the digested and undigested material was added to 400 μl, of 2% non-fat dry milk in PBS-T (PBS, 0.05% TWEEN, pH 7.4) and analyzed by ELISA, as described below.

Interferon ELISA's: A recombinant Interferon receptor 1-Fc (IFNR1-Fc) fusion protein (R & D Systems) was used to detect IFN-α binding. Briefly, the receptor was absorbed to ELISA plates at a concentration of 5 μg/mL in PBS for 1 hr at RT. Wells were then blocked with 2% non-fat dry milk in PBS-T for 1 hr at RT. Interferon-α was added to the well in 100 μl of 2% non-fat dry milk in PBS-T. Wells were washed 3 times with PBS-T and the interferon was detected with an anti-$His_6$ (SEQ ID NO: 84) monoclonal antibody (Invitrogen) at a titer of 1:1000 mixed with an anti-muFc-HRP conjugate (Fisher) at a titer of 1:2000 in a 100 uL of 2% non-fat dry milk in PBS-T per well. The ELISA was developed with 100 μl of TMB (Pierce) following the manufacturer's protocol.

IFN-α masking efficiency assay: IFNR-α is adsorbed to the wells of an ELISA plate overnight at about 4° C. The plate is blocked by addition of about 150 ul 2% non-fat dry milk (NFDM) in PBS, about 0.5% V/V tween 20 (PBST), and incubated at room temperature for about 1 hour. The plate is washed about three times with PBST. About 50 ul superblock (Thermo Scientific) supplemented with protease inhibitors (Complete, Roche) is added. About 50 ul of a solution of pro-IFN-α dissolved in superblock with protease inhibitors (Complete, Roche) is added and incubated at about 37° C. for desired time. The plate is washed about three times with PBST. About 100 ul of anti-His-HRP in 2% NFDM/PBST is added and incubated at room temperature for about 1 hour. The plate is washed about four times with PBST and about twice with PBS. The assay is developed using TMB (Thermo Scientific) as per manufacturer's directions. An efficiently masked pro-IFN-α would be expected to show less than 10% of the binding observed for unmasked IFN-α.

Example 5

Construction of a Masked Soluble Plasmin or MMP-9 Activatable Notch Receptor Protein Sequences to construct a masked plasmin-activatable soluble Notch Receptor fragment and a masked MMP9-activatable soluble Notch Receptor fragment are provided in this example. These proproteins are inactive under normal conditions due to the attached peptide mask. Bacterial cell surface display is used to find suitable peptide masks for the soluble Notch receptor protein. In this example, selected peptide masks are combined with either a plasmin or MMP-9 enzyme substrate to be used as a trigger to create a proprotein construct that becomes competent for targeted binding after enzyme-mediated activation.

The gene encoding human Notch1 EGF-like domains 11-13 ($hN1_{11-13}$) was constructed by PCR assembly of overlapping oligonucleotides CX509-CX528 (Table 13), digested with EcoRI/BglII, and ligated to pINFUSE-hIgG1-Fc2 (InvivoGen) that had been digested with EcoRI/BglII. The resulting plasmid was used for CHO-S expression of $hN1_{11-13}$ fused to the Fc domain of human IgG1 ($hN1_{11\_13}$-hFc). The $hN1_{11\_13}$-hFc was purified from cell culture supernatant by Protein A chromatography and labeled with PEG-biotin or DyLight488 (Thermo Pierce) following standard protocols.

TABLE 13

| Oligonucleotides used for constructing hN111-13 | |
|---|---|
| CX509 | GTCACGAATTCGCAGGACGTCGACGAGTGCTCGCTGGGT (SEQ ID NO: 35) |
| CX510 | GCTCGCAGGGGTTGGCACCCAGCGAGCACTCGT (SEQ ID NO: 36) |
| CX511 | GCCAACCCCTGCGAGCATGCGGGCAAGTGCATCA (SEQ ID NO: 37) |
| CX512 | GAAGGAGCCCAGCGTGTTGATGCACTTGCCCGCAT (SEQ ID NO: 38) |
| CX513 | ACACGCTGGGCTCCTTCGAGTGCCAGTGTCTGCAGG (SEQ ID NO: 39) |
| CX514 | CGGGGGCCCGTGTAGCCCTGCAGACACTGGCACTC (SEQ ID NO: 40) |
| CX515 | GCTACACGGGCCCCCGATGCGAGATCGACGTCAACG (SEQ ID NO: 41) |
| CX516 | ACGGGTTCGAGACGCACTCGTTGACGTCGATCTCGCAT (SEQ ID NO: 42) |
| CX517 | AGTGCGTCTCGAACCCGTGCCAGAACGACGCCACC (SEQ ID NO: 43) |
| CX518 | CCCAATCTGGTCCAGGCAGGTGGCGTCGTTCTGGC (SEQ ID NO: 44) |
| CX519 | TGCCTGGACCAGATTGGGGAGTTCCAGTGCATCTGCATGC (SEQ ID NO: 45) |
| CX520 | CACACCCTCGTAGCCGGGCATGCAGATGCACTGGAACTC (SEQ ID NO: 46) |
| CX521 | CCGGCTACGAGGGTGTGCACTGCGAGGTCAACACAGA (SEQ ID NO: 47) |
| CX522 | GGCTGCTGGCACACTCGTCTGTGTTGACCTCGCAGTG (SEQ ID NO: 48) |
| CX523 | CGAGTGTGCCAGCAGCCCCTGCCTGCACAATGGCC (SEQ ID NO: 49) |

TABLE 13-continued

Oligonucleotides used for constructing hN1 11-13

CX524 TCATTGATCTTGTCCAGGCAGCGGCCATTGTGCAGGCAGG (SEQ ID NO: 50)

CX525 GCTGCCTGGACAAGATCAATGAGTTCCAGTGCGAGTGCCC (SEQ ID NO: 51)

CX526 GCCCAGTGAAGCCCGTGGGGCACTCGCACTGGAAC (SEQ ID NO: 52)

CX527 CACGGGCTTCACTGGGCATCTGTGCCAGGGCAGC (SEQ ID NO: 53)

CX528 GTCGTCTGGTGGATCCACCGCTGCCCTGGCACAGAT (SEQ ID NO: 54)

A library of peptides containing 15 random amino acids displayed on the *E. coli* surface was used for screening for peptides that bind hN1$_{11-13}$-hFc. Approximately 1.5×10$^{11}$ library cells, induced with 0.04% arabinose for 45 minutes at 37° C., were depleted of streptavidin (SA) binders by incubating with 10$^9$ SA-coated magnetic beads (Invitrogen Dynabeads MyOne SA-C1) in Tris-buffered saline (50 mM Tris-HCl ph 7.4, 150 mM NaCl) with 2 mM CaCl$_2$ and 0.5% bovine serum albumin (TBS-Ca-B). The magnetic beads were then removed using a magnet, and the remaining cell population was mixed with 300 nM hN1$_{11-13}$-hFc that had been biotinylated with NHS-PEG-biotin (Thermo Pierce) (hN1$_{11-13}$-hFc-biot) and 5 µM pooled human IgG that had been depleted of *E. coli*-binding antibodies (hIgG). The cells were washed with TBS-Ca-B, and incubated with 10$^9$ SA-coated beads and 5 µM hIgG. The beads were then washed three times, and incubated in LB medium overnight to amplify the hN1$_{11-13}$-hFc-binding population. A second round of magnetic selection was performed as in the first round, starting with 3×10$^8$ cells from the first round enriched population, 600 nM hN1$_{11-13}$-hFc-biot, 10 µM hIgG, and 5×10$^8$ SA-coated beads.

Following two rounds of magnetic selection, the remaining rounds of screening were performed on a Becton Dickinson FACSAria flow cytometer. In the first round of FACS, induced cells were incubated with 500 nM hN1$_{11-13}$-hFc-biot, 10 µM hIgG in TBS-Ca-B, washed, and incubated with fluorescent secondary label neutravidin-phycoerythrin (NAPE) (Invitrogen) at 10 nM, before sorting by flow cytometry for fluorescently labeled cells. Cells amplified from overnight growth of the first round FACS population were induced and subjected to a second round of sorting with the same labeling conditions as in the first round or, alternatively, using 50 nM hN1$_{11-13}$-hFc-biot. A third round of sorting was conducted as in the second round but with 100 nM hN1$_{11-13}$-hFc-biot and the addition of 27 nM Ypet-Mona-SH3 in the secondary labeling step. Mona-SH3 binds an epitope on the C-terminus of the display scaffold, independent of the random peptide on the N-terminus. Cells were then sorted based on the ratio of 576 nm fluorescence (i.e. NAPE binding) to 530 nm fluorescence (i.e. Ypet-Mona binding) in order to normalize for differences in scaffold display level on individual cells.

Alternatively, third round sorting was conducted by incubating induced cells with 10 nM or alternatively, 50 nM unbiotinylated hN1$_{11-13}$-hFc in TBS-Ca-B before washing, labeling with fluorescent secondary 20 µg/ml anti-hIgG-DyLight-488, and sorting based on 530 nm fluorescence. Third round sorting was also conducted using either 50 nM or 250 nM hN1$_{11-13}$-hFc that had been fluorescently labeled with DyLight-488 (Thermo Pierce) (hN1$_{11-13}$-hFc-Dy488), and 10 µM hIgG, with no secondary labeling. Colonies derived from FACS round 3 populations enriched for hN1$_{11-13}$-hFc binding were used for plasmid sequencing in order to discover the sequences of the encoded peptides.

Figures 3, 4:
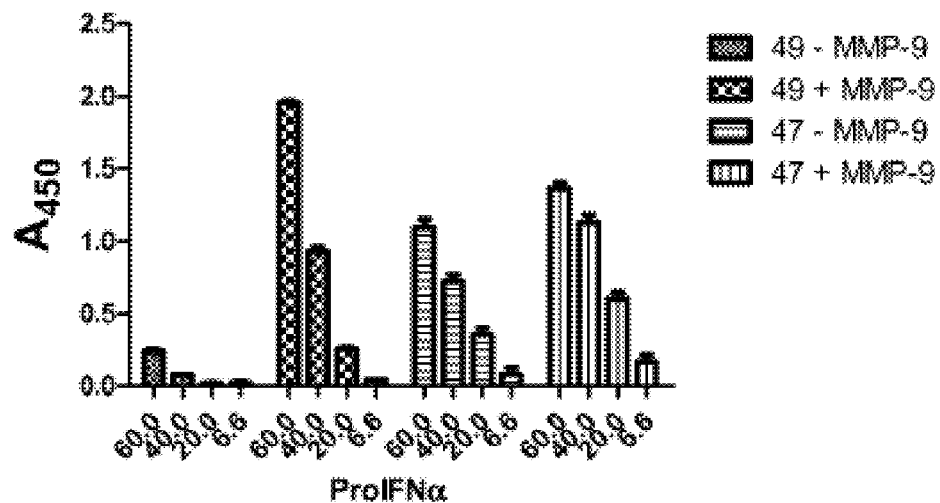
FIG. 3 depicts the binding of two pro-IFN-α molecules, pro-IFN-α-47 and pro-IFN-α-49CS, before and after treatment with MMP-9.
FIG. 4 depicts testing of individual clones for binding to human Notch 1 EGF-like domains 11-13.

Individual clones were tested by flow cytometry for hN1$_{11-13}$-hFc binding by labeling induced cells in TBS-Ca-B with (A.) 50 nM hN1$_{11-13}$-hFc-biot or (B.) 100 nM 50 nM hN1$_{11-13}$-hFc-biot, followed by 10 nM Streptavidin-R-phycoerythrin (SAPE). Cells were separately labeled with 27 nM Ypet-Mona to measure peptide display level. The display scaffold alone (ecpX3) was used as a negative control. Clones Jag-ecpX3 and RJag-ecpX3 display a fragment of JAG1 and a mutated fragment, respectively, which have been shown to bind Notch1$_{11-13}$. (Table 14 and FIG. 4). FIG. 4 shows individual clones that were tested by flow cytometry for hN1$_{11-13}$-hFc binding by labeling induced cells in TBS-Ca-B with 100 nM hN1$_{11-13}$-hFc-biot, followed by 10 nM Streptavidin-R-phycoerythrin (SAPE), and normalized based on the display level of the scaffold. Clone ecpX3 displays the scaffold alone, and clone Jag-ecpX3 displays a peptide derived from Jagged1 (RVTCDDYYYG-FGCNKFGRPA (SEQ ID NO: 55)) that is known to bind Notch1. The clones resulting from library screening bind hN1$_{11-13}$-hFc better than the Jagged1-derived peptide.

TABLE 14

Binders to hN1$_{11-13}$-hFc after two rounds of magnetic selection and three rounds of FACS

PHB3324 FPLNTFDLVHELLSR (SEQ ID NO: 56)

PHB3325 FLNDIHRFLHWTDLM (SEQ ID NO: 57)

PHB3327 PYTFVEQVEYWLHAT (SEQ ID NO: 58)

PHB3333 ACVIHFLDRISNILE (SEQ ID NO: 59)

PHB3334 FCYIAAFSAMQRQSC (SEQ ID NO: 60)

PHB3336 PLYLPEIGWMFGLPT (SEQ ID NO: 61)

PHB3337 TVLVIPDLHYLYVDR (SEQ ID NO: 62)

PHB3340 FINNVETALDTIYNL (SEQ ID NO: 63)

PHB3341 SAKHLHPGRLPPMTK (SEQ ID NO: 64)

PHB3343 ATMYAYLERLEAILS (SEQ ID NO: 65)

PHB3349 IYPLDALLRHLNSLC (SEQ ID NO: 66)

PHB3352 CFPTVVWRELYNLYG (SEQ ID NO: 67)

PHB3476 NLDFYLNHLYNTLAG (SEQ ID NO: 68)

PHB3478 DFINSMRSHLQSSDQ (SEQ ID NO: 69)

PHB3479 EPKCSFCSPLIVPSP (SEQ ID NO: 70)

PHB3480 PNCIESFLSSIHDSL (SEQ ID NO: 71)

TABLE 14-continued

Binders to hN1₁₁₋₁₃-hFc after two rounds of magnetic selection and three rounds of FACS

PHB3482 TDNALFLETVQHYLY (SEQ ID NO: 72)

PHB3485 CYPSISWLFADAPRN (SEQ ID NO: 73)

PHB3486 ELTQLLNALVDVRNC (SEQ ID NO: 74)

PHB3487 LLSSFVETMSSILTC (SEQ ID NO: 75)

PHB3488 YLLRLPSLEELWGPS (SEQ ID NO: 76)

PHB3489 ATCYIINHWVERYII (SEQ ID NO: 77)

TABLE 15

Nucleotide Sequence of the Soluble Notch Receptor Fragment caggacgtcgacgagtgctcgctgggtgccaacccctgcgagcatgcggg caagtgcatcaacacgctgggctccttcgagtgccagtgtctgcagggct acacgggcccccgatgcgagatcgacgtcaacgagtgcgtctcgaacccg tgccagaacgacgccacctgcctggaccagattggggagttccagtgcat ctgcatgcccggctacgagggtgtgcactgcgaggtcaacacagacgagt gtgccagcagccctgcctgcacaatggccgctgcctggacaagatcaat gagttccagtgcgagtgccccacgggcttcactgggcatctgtgccag (SEQ ID NO: 78)

TABLE 16

Amino Acid Sequence of the Soluble Notch Receptor Fragment qdvdecslganpcehagkcintlgsfecqclqgytgprceidvnecvsnp cqndatcldqigefqcicmpgyegvhcevntdecasspclhngrcldkin efqcecptgftghlcq (SEQ ID NO: 79)

TABLE 17

Nucleotide Sequence Plasmin Activatable Masked Soluble Notch Receptor Fragment cgcgtaacttgtgacgattactactacggattcgggtgtaacaagtttgg tagacccgccggcggcggatcaggcggagggtcaggaggcggtagcggcg ggggctccggcggcggttcaggggga ggatcccaaggaccaatgttcaaa agcctatgggacggaggccaggacgtcgacgagtgctcgctgggtgccaa cccctgcgagcatgcgggcaagtgcatcaacacgctgggctccttcgagt gccagtgtctgcagggctacacgggcccccgatgcgagatcgacgtcaac gagtgcgtctcgaacccgtgccagaacgacgccacctgcctggaccagat tggggagttccagtgcatctgcatgcccggctacgagggtgtgcactgcg aggtcaacacagacgagtgtgccagcagccctgcctgcacaatggccgc

TABLE 17-continued

Nucleotide Sequence Plasmin Activatable Masked Soluble Notch Receptor Fragment tgcctggacaagatcaatgagttccagtgcgagtgccccacgggcttcac tgggcatctgtgccag (SEQ ID NO: 80)

TABLE 18

Amino Acid Sequence Plasmin Activatable Masked Soluble Notch Receptor Fragment Parentheses delineate the demarcations between the various sequence domains: (Peptide Mask)-(Linker)-(Plasmin Substrate)-(GG Linker)-(Soluble Notch Receptor Fragment)

(RVTCDDYYYGFGCNKFGRPA) (GGGSGGGSGGGSGGGSGGGSGGGS)

(QGPMFKSLWD) (GG) (QDVDECSLGANPCEHAGKCINTLGSFECQCLQG

YTGPRCEIDVNECVSNPCQNDATCLDQIGEFQCICMPGYEGVHCEVNTDE

CASSPCLHNGRCLDKINEFQCECPTGFTGHLCQ) (SEQ ID NO: 81)

TABLE 19

Nucleotide Acid Sequence MMP9 Activatable Masked Soluble Notch Receptor Fragment cgcgtaacttgtgacgattactactacggattcgggtgtaacaagtttgg tagacccgccggcggcggatcaggcggagggtcaggaggcggtagcggcg ggggctccggcggcggttcaggggga ggatccgttcatatgcccttgggt ttcctggggccaggaggccaggacgtcgacgagtgctcgctgggtgccaa cccctgcgagcatgcgggcaagtgcatcaacacgctgggctccttcgagt gccagtgtctgcagggctacacgggcccccgatgcgagatcgacgtcaac gagtgcgtctcgaacccgtgccagaacgacgccacctgcctggaccagat tggggagttccagtgcatctgcatgcccggctacgagggtgtgcactgcg aggtcaacacagacgagtgtgccagcagccctgcctgcacaatggccgc tgcctggacaagatcaatgagttccagtgcgagtgccccacgggcttcac tgggcatctgtgccag (SEQ ID NO: 82)

TABLE 20

Amino Acid Sequence MMP9 Activatable Masked Soluble Notch Receptor Fragment Parentheses delineate the demarcations between the various sequence domains: (Peptide Mask)-(Linker)-(MMP9 Substrate)-(GG Linker)-(Soluble Notch Receptor Fragment)

(RVTCDDYYYGFGCNKFGRPA) (GGGSGGGSGGGSGGGSGGGSGGGS)

(VHMPLGFLGP) (GG) (QDVDECSLGANPCEHAGKCINTLGSFECQCLQG

YTGPRCEIDVNECVSNPCQNDATCLDQIGEFQCICMPGYEGVHCEVNTDE

CASSPCLHNGRCLDKINEFQCECPTGFTGHLCQ) (SEQ ID NO: 83)

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising an activatable polypeptide comprising a functional protein that is not an antibody or an antibody fragment, wherein the functional protein is a soluble Notch receptor or fragment thereof, wherein the functional protein is coupled to a peptide mask that: (i) inhibits binding of the functional protein to its binding partner and (ii) does not have an amino acid sequence of the binding partner, and wherein the functional protein is further coupled to a cleavable linker, such that: (i) when the activatable polypeptide is in an uncleaved state, the peptide mask inhibits binding of the functional protein to its binding partner and (ii) when the activatable polypeptide is in a cleaved state, the peptide mask does not inhibit binding of the functional protein to its binding partner.

2. The composition of claim 1, wherein the cleavable linker includes one or more substrates selected from the group consisting of: a sequence that is susceptible to specific cleavage by an enzyme, a bond that is susceptible to reductive cleavage by a reducing agent, and a bond that is susceptible to photolytic cleavage.

3. The composition of claim 1, wherein the activatable polypeptide is recombinantly expressed.

4. The composition of claim 1, wherein the peptide mask has one or more of the following characteristics: (i) the peptide mask is unique for the functional protein; (ii) the peptide mask has a therapeutic effect once uncoupled from the functional protein; (iii) the peptide mask is 8-15 amino acids in length; (iv) the peptide mask has less than 50% amino acid sequence homology to the natural binding partner of the functional protein; (v) the peptide mask contains less than 50% genetically non-encoded amino acids; (vi) the peptide mask contains less than 50% genetically non-encoded amino acids, wherein the genetically non-encoded amino acids are D-amino acids, β-amino acids, or γ-amino acids; (vii) the peptide mask inhibits binding of the functional protein to its binding partner allosterically; (viii) the peptide mask inhibits binding of the functional protein to its binding partner sterically; (ix) the binding affinity of the peptide mask to the functional protein is less than the binding affinity of the binding partner to the functional protein; (x) the dissociation constant ($K_d$) of the peptide mask towards the functional protein is at least 100 times greater than the $K_d$ of the functional protein towards its binding partner; or (xi) the $K_d$ of the peptide mask towards the functional protein is lower than about 5 nM.

5. The composition of claim 1, wherein the peptide mask has one or more of the following characteristics: (i) the peptide mask inhibits the binding of the soluble receptor to its ligand; (ii) the peptide mask inhibits the soluble receptor's ligand binding domain; or (iii) the peptide mask contains a sequence selected from those presented in Table 14 or a sequence having at least 90% homology thereof.

6. The composition of claim 1, wherein the Notch receptor is selected from the group consisting Notch1, Notch2, Notch3 and Notch4.

7. The composition of claim 5, wherein the ligand is selected from the group consisting of DLL1, DLL3, DLL4, Jagged1, and Jagged2.

8. The composition of claim 1, wherein the cleavable linker is a substrate for an enzyme selected from Table 2.

9. The composition of claim 1, wherein the cleavable linker is a substrate for an enzyme selected from the group consisting of matriptase, plasmin, MMP-9, uPA, HCV-NS3/4, PSA, and legumain.

10. The composition of claim 9, wherein a sequence for an MMP-9 substrate comprises VHMPLGFLGP (SEQ ID NO: 3).

11. The composition of claim 9, wherein a sequence for a plasmin substrate comprises QGPMFKSLWD (SEQ ID NO: 4).

12. The composition of claim 1 further comprising an Fc region of an immunoglobulin.

13. The composition of claim 2, wherein when the activatable polypeptide is not in the presence of an enzyme that cleaves the cleavable linker, the peptide mask inhibits the binding of the functional protein to its binding partner by at least 90% as compared to when the activatable polypeptide is in the presence of the enzyme that cleaves the cleavable linker and the peptide mask does not inhibit the binding of the functional protein to its binding partner.

14. The composition of claim 2, wherein the cleavable linker is specifically cleaved by an enzyme at a rate of at least $5 \times 10^4$ $M^{-1}$ $s^{-1}$.

15. A pharmaceutical composition, wherein said pharmaceutical composition comprises a therapeutically effective amount of a composition according to claim 1 and a pharmaceutically acceptable excipient.

16. A method of treating a disease or disorder, said method comprising administering to a subject in need thereof a therapeutically effective amount of the pharmaceutical composition of claim 15.

17. The method of claim 16, wherein the disease or disorder is cancer.

18. A method of inhibiting angiogenesis in a mammalian subject, said method comprising administering to a subject in need thereof a therapeutically effective amount of the pharmaceutical composition of claim 15.

19. The composition of claim 2, wherein the enzyme is a protease.

20. The composition of claim 19, wherein the protease is selected from the group consisting of: matriptase, plasmin, MMP-9, uPA, HCV-NS3/4, PSA, and legumain.

21. The composition of claim 1, wherein the activatable polypeptide comprises at least one linker.

22. The composition of claim 21, wherein at least one of the linkers is a glycine-serine rich linker.

23. The composition of claim 22, wherein one or more of the glycine-serine rich linkers is selected from the group consisting of GQSGQ (SEQ ID NO: 88), GSSGGS (SEQ ID NO: 89), GGS (SEQ ID NO: 90), GGGSGGGSGGGSGGGSGGGSGGGS (SEQ ID NO: 91), and GG (SEQ ID NO: 92).

24. The composition of claim 21, wherein the activatable polypeptide comprises at least one linker between the peptide mask and the functional protein.

25. The composition of claim 21, wherein the activatable polypeptide comprises at least one linker between the cleavable linker and the peptide mask.

26. The composition of claim 21, wherein the activatable polypeptide comprises at least one linker between the cleavable linker and the functional protein.

27. The composition of claim 21, wherein the activatable polypeptide comprises at least one linker between the cleavable linker and the functional protein, and at least one linker between the cleavable linker and the peptide mask.

28. The composition of claim 21, wherein the activatable polypeptide comprises an arrangement of the functional protein, the peptide mask, and the cleavable linker from N-terminus to C-terminus, wherein the arrangement is selected from the group consisting of: [peptide mask]-L1-[cleavable linker]-L2-[functional protein], and [functional protein]-L1-[cleavable linker]-L2-[peptide mask], wherein L1 and L2 are linkers.

* * * * *

```
                              SEQUENCE LISTING

<160> NUMBER OF SEQ ID NOS: 92

<210> SEQ ID NO 1
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (10)..(17)
<223> OTHER INFORMATION: Any amino acid

<400> SEQUENCE: 1

Thr Asp Val Asp Tyr Tyr Arg Glu Trp Xaa Xaa Xaa Xaa Xaa Xaa Xaa
1               5                   10                  15

Xaa

<210> SEQ ID NO 2
<211> LENGTH: 4
<212> TYPE: PRT
<213> ORGANISM: Artificial Sequence
<220> FEATURE:
<223> OTHER INFORMATION: chemically synthesized

<400> SEQUENCE: 2

Ala Gly Pro Arg
1

<210> SEQ ID NO 3
<211> LENGTH: 10
<212> TYPE: PRT
<213> ORGANISM: Artificial Sequence
<220> FEATURE:
<223> OTHER INFORMATION: chemically synthesized

<400> SEQUENCE: 3

Val His Met Pro Leu Gly Phe Leu Gly Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: chemically synthesized

<400> SEQUENCE: 4

Gln Gly Pro Met Phe Lys Ser Leu Trp Asp
1               5                   10

<210> SEQ ID NO 5
<211> LENGTH: 5
<212> TYPE: PRT
<213> ORGANISM: Artificial Sequence
<220> FEATURE:
<223> OTHER INFORMATION: chemically synthesized

<400> SEQUENCE: 5

Gly Ser Gly Gly Ser
1               5
```

<210> SEQ ID NO 6
<211> LENGTH: 4
<212> TYPE: PRT
<213> ORGANISM: Artificial Sequence
<220> FEATURE:
<223> OTHER INFORMATION: chemically synthesized

<400> SEQUENCE: 6

Gly Gly Gly Ser
1

<210> SEQ ID NO 7
<211> LENGTH: 4
<212> TYPE: PRT
<213> ORGANISM: Artificial Sequence
<220> FEATURE:
<223> OTHER INFORMATION: chemically synthesized

<400> SEQUENCE: 7

Gly Gly Ser Gly
1

<210> SEQ ID NO 8
<211> LENGTH: 5
<212> TYPE: PRT
<213> ORGANISM: Artificial Sequence
<220> FEATURE:
<223> OTHER INFORMATION: chemically synthesized

<400> SEQUENCE: 8

Gly Gly Ser Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: chemically synthesized

<400> SEQUENCE: 9

Gly Ser Gly Ser Gly
1               5

<210> SEQ ID NO 10
<211> LENGTH: 5
<212> TYPE: PRT
<213> ORGANISM: Artificial Sequence
<220> FEATURE:
<223> OTHER INFORMATION: chemically synthesized

<400> SEQUENCE: 10

Gly Ser Gly Gly Gly
1               5

<210> SEQ ID NO 11
<211> LENGTH: 5
<212> TYPE: PRT
<213> ORGANISM: Artificial Sequence
<220> FEATURE:
<223> OTHER INFORMATION: chemically synthesized

<400> SEQUENCE: 11

Gly Gly Gly Ser Gly
1               5

<210> SEQ ID NO 12
<211> LENGTH: 5
<212> TYPE: PRT
<213> ORGANISM: Artificial Sequence
<220> FEATURE:
<223> OTHER INFORMATION: chemically synthesized

<400> SEQUENCE: 12

Gly Ser Ser Ser Gly
1               5

<210> SEQ ID NO 13
<211> LENGTH: 15
<212> TYPE: PRT
<213> ORGANISM: Artificial Sequence
<220> FEATURE:
<223> OTHER INFORMATION: chemically synthesized

<400> SEQUENCE: 13

Ile Ala Tyr Leu Glu Tyr Tyr Glu His Leu His Met Ala Tyr Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: chemically synthesized

<400> SEQUENCE: 14

Thr Asp Val Asp Tyr Tyr Arg Glu Trp Cys Trp Thr Gln Val Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: chemically synthesized

<400> SEQUENCE: 15

Thr Asp Val Asp Tyr Tyr Arg Glu Trp Ser Trp Thr Gln Val Ser
1               5                   10                  15

<210> SEQ ID NO 16
<211> LENGTH: 40
<212> TYPE: DNA
<213> ORGANISM: Artificial Sequence
<220> FEATURE:
<223> OTHER INFORMATION: chemically synthesized

<400> SEQUENCE: 16
gctttcaccg caggtacttc cgtagctggc cagtctggcc                    40

<210> SEQ ID NO 17
<211> LENGTH: 46
<212> TYPE: DNA
<213> ORGANISM: Artificial Sequence
<220> FEATURE:
<223> OTHER INFORMATION: chemically synthesized

<400> SEQUENCE: 17
gagttttgtc ggatccacca gagccaccgc tgccaccgct cgagcc             46

<210> SEQ ID NO 18
<211> LENGTH: 62
<212> TYPE: DNA

<210> SEQ ID NO 18
<211> LENGTH: 62
<212> TYPE: DNA
<213> ORGANISM: Artificial Sequence
<220> FEATURE:
<223> OTHER INFORMATION: chemically synthesized

<400> SEQUENCE: 18
gcgttatccc gaattcctag tggtgatggt gatgatgttc cttacttctt aaactttctt    60
gc                                                                   62

<210> SEQ ID NO 19
<211> LENGTH: 32
<212> TYPE: DNA
<213> ORGANISM: Artificial Sequence
<220> FEATURE:
<223> OTHER INFORMATION: chemically synthesized

<400> SEQUENCE: 19
agtgaattgt aagctttgga gattatcgtc ac                                  32

<210> SEQ ID NO 20
<211> LENGTH: 54
<212> TYPE: DNA
<213> ORGANISM: Artificial Sequence
<220> FEATURE:
<223> OTHER INFORMATION: chemically synthesized

<400> SEQUENCE: 20
caggctgtgg gtttgaggca gatcacacat tttattttct ccatgtacaa atac          54

<210> SEQ ID NO 21
<211> LENGTH: 27
<212> TYPE: DNA
<213> ORGANISM: Artificial Sequence
<220> FEATURE:
<223> OTHER INFORMATION: chemically synthesized

<400> SEQUENCE: 21
tgtgatctgc ctcaaaccca cagcctg                                        27

<210> SEQ ID NO 22
<211> LENGTH: 33
<212> TYPE: DNA
<213> ORGANISM: Artificial Sequence
<220> FEATURE:
<223> OTHER INFORMATION: chemically synthesized

<400> SEQUENCE: 22
ggtggcagca tgtgtgatct gcctcaaacc cac                                 33

<210> SEQ ID NO 23
<211> LENGTH: 58
<212> TYPE: DNA
<213> ORGANISM: Artificial Sequence
<220> FEATURE:
<223> OTHER INFORMATION: chemically synthesized

<400> SEQUENCE: 23
ggctcgagcg gcggctccgg cggtagcggt ggctctggtg gcagcatgtg tgatctgc      58

<210> SEQ ID NO 24
<211> LENGTH: 67
<212> TYPE: DNA
<213> ORGANISM: Artificial Sequence
<220> FEATURE:
<223> OTHER INFORMATION: chemically synthesized

<400> SEQUENCE: 24
tgcgtatgca ggatccggcc agtctggcca gcaagtcatt ctgagaagcg gctcgagcgg    60
cggctcc                                                              67

<210> SEQ ID NO 25
<211> LENGTH: 54
<212> TYPE: DNA
<213> ORGANISM: Artificial Sequence
<220> FEATURE:
<223> OTHER INFORMATION: chemically synthesized

<400> SEQUENCE: 25
ttccgtagct ggccagtctg gccagacgga cgtggactat tatagggagt ggtc          54

<210> SEQ ID NO 26
<211> LENGTH: 54
<212> TYPE: DNA
<213> ORGANISM: Artificial Sequence
<220> FEATURE:
<223> OTHER INFORMATION: chemically synthesized

<400> SEQUENCE: 26
gctgccaccg ctcgagcctg atacttgagt ccaggaccac tccctataat agtc          54

<210> SEQ ID NO 27
<211> LENGTH: 44
<212> TYPE: DNA
<213> ORGANISM: Artificial Sequence
<220> FEATURE:
<223> OTHER INFORMATION: chemically synthesized

<400> SEQUENCE: 27
catgccactg ggcttcctgg gtccgggtgg cagcatgtgt gatc                      44

<210> SEQ ID NO 28
<211> LENGTH: 45
<212> TYPE: DNA
<213> ORGANISM: Artificial Sequence
<220> FEATURE:
<223> OTHER INFORMATION: chemically synthesized

<400> SEQUENCE: 28
ccaggaagcc cagtggcatg tgcacggagc cgccgctcga gccgc                     45

<210> SEQ ID NO 29
<211> LENGTH: 516
<212> TYPE: DNA
<213> ORGANISM: Artificial Sequence
<220> FEATURE:
<223> OTHER INFORMATION: chemically synthesized

<400> SEQUENCE: 29
atgtgtgatc tgcctcaaac ccacagcctg ggtagcagga ggaccttgat gctcctggca    60
cagatgagga gaatctctct tttctcctgc ttgaaggaca gacatgactt tggatttccc   120
caggaggagt ttggcaacca gttccaaaag gctgaaacca tccctgtcct ccatgagatg   180
atccagcaga tcttcaatct cttcagcaca aaggactcat ctgctgcttg ggatgagacc   240
ctcctagaca aattctacac tgaactctac cagcagctga atgacctgga agcctgtgtg   300 atacagggggg tgggggtgac agagactccc ctgatgaagg aggactccat tctggctgtg   360
aggaaatact tccaaagaat cactctctat ctgaaagaga gaaatacag cccttgtgcc    420 tgggaggttg tcagagcaga aatcatgaga tcttttttctt tgtcaacaaa cttgcaagaa   480
agtttaagaa gtaaggaaca tcaccatcat caccat 516

<210> SEQ ID NO 30
<211> LENGTH: 172
<212> TYPE: PRT
<213> ORGANISM: Artificial Sequence
<220> FEATURE:
<223> OTHER INFORMATION: chemically synthesized

<400> SEQUENCE: 30

```
Met Cys Asp Leu Pro Gln Thr His Ser Leu Gly Ser Arg Arg Thr Leu
1               5                   10                  15
Met Leu Leu Ala Gln Met Arg Arg Ile Ser Leu Phe Ser Cys Leu Lys
            20                  25                  30
Asp Arg His Asp Phe Gly Phe Pro Gln Glu Glu Phe Gly Asn Gln Phe
        35                  40                  45
Gln Lys Ala Glu Thr Ile Pro Val Leu His Glu Met Ile Gln Gln Ile
    50                  55                  60
Phe Asn Leu Phe Ser Thr Lys Asp Ser Ser Ala Ala Trp Asp Glu Thr
65                  70                  75                  80
Leu Leu Asp Lys Phe Tyr Thr Glu Leu Tyr Gln Gln Leu Asn Asp Leu
                85                  90                  95
Glu Ala Cys Val Ile Gln Gly Val Gly Val Thr Glu Thr Pro Leu Met
            100                 105                 110
Lys Glu Asp Ser Ile Leu Ala Val Arg Lys Tyr Phe Gln Arg Ile Thr
        115                 120                 125
Leu Tyr Leu Lys Glu Lys Lys Tyr Ser Pro Cys Ala Trp Glu Val Val
    130                 135                 140
Arg Ala Glu Ile Met Arg Ser Phe Ser Leu Ser Thr Asn Leu Gln Glu
145                 150                 155                 160
Ser Leu Arg Ser Lys Glu His His His His His His
                165                 170
```

<210> SEQ ID NO 31
<211> LENGTH: 630
<212> TYPE: DNA
<213> ORGANISM: Artificial Sequence
<220> FEATURE:
<223> OTHER INFORMATION: chemically synthesized

<400> SEQUENCE: 31
ggccagtctg gccagattgc gtaccttgag tattatgagc acctacatat ggcctacggc    60
tcgagcggcg gctccgtgca catgccactg ggcttcctgg gtccgggtgg cagcatgtgt   120
gatctgcctc aaacccacag cctgggtagc aggaggacct tgatgctcct ggcacagatg   180
aggagaatct ctcttttctc ctgcttgaag gacagacatg actttggatt ccccaggag    240 gagtttggca accagttcca aaaggctgaa accatccctg tcctccatga gatgatccag   300
cagatcttca atctcttcag cacaaaggac tcatctgctg cttgggatga gaccctccta   360
gacaaattct acactgaact ctaccagcag ctgaatgacc tggaagcctg tgtgatacag   420
ggggtggggg tgacagagac tcccctgatg aaggaggact ccattctggc tgtgaggaaa   480
tacttccaaa gaatcactct ctatctgaaa gagaagaaat acagcccttg tgcctgggag   540
gttgtcagag cagaaatcat gagatctttt tctttgtcaa caaacttgca agaaagttta   600
agaagtaagg aacatcacca tcatcaccat                                    630

<210> SEQ ID NO 32

<211> LENGTH: 210
<212> TYPE: PRT
<213> ORGANISM: Artificial Sequence
<220> FEATURE:
<223> OTHER INFORMATION: chemically synthesized

<400> SEQUENCE: 32

Gly Gln Ser Gly Gln Ile Ala Tyr Leu Glu Tyr Glu His Leu His
1               5                   10                  15

Met Ala Tyr Gly Ser Ser Gly Gly Ser Val His Met Pro Leu Gly Phe
            20                  25                  30

Leu Gly Pro Gly Gly Ser Met Cys Asp Leu Pro Gln Thr His Ser Leu
            35                  40                  45

Gly Ser Arg Arg Thr Leu Met Leu Leu Ala Gln Met Arg Arg Ile Ser
        50                  55                  60

Leu Phe Ser Cys Leu Lys Asp Arg His Asp Phe Gly Phe Pro Gln Glu
65                  70                  75                  80

Glu Phe Gly Asn Gln Phe Gln Lys Ala Glu Thr Ile Pro Val Leu His
                85                  90                  95

Glu Met Ile Gln Gln Ile Phe Asn Leu Phe Ser Thr Lys Asp Ser Ser
            100                 105                 110

Ala Ala Trp Asp Glu Thr Leu Leu Asp Lys Phe Tyr Thr Glu Leu Tyr
            115                 120                 125

Gln Gln Leu Asn Asp Leu Glu Ala Cys Val Ile Gln Gly Val Gly Val
        130                 135                 140

Thr Glu Thr Pro Leu Met Lys Glu Asp Ser Ile Leu Ala Val Arg Lys
145                 150                 155                 160

Tyr Phe Gln Arg Ile Thr Leu Tyr Leu Lys Glu Lys Lys Tyr Ser Pro
                165                 170                 175

Cys Ala Trp Glu Val Val Arg Ala Glu Ile Met Arg Ser Phe Ser Leu
            180                 185                 190

Ser Thr Asn Leu Gln Glu Ser Leu Arg Ser Lys Glu His His His His
        195                 200                 205

His His
    210

<210> SEQ ID NO 33
<211> LENGTH: 633
<212> TYPE: DNA
<213> ORGANISM: Artificial Sequence
<220> FEATURE:
<223> OTHER INFORMATION: chemically synthesized

<400> SEQUENCE: 33
ggccagtctg gccagacgga cgtggactat tatagggagt ggtcctggac tcaagtatca    60
ggctcgagcg gcggctccgt gcacatgcca ctgggcttcc tgggtccggg tggcagcatg   120
tgtgatctgc ctcaaaccca cagcctgggt agcaggagga ccttgatgct cctggcacag   180
atgaggagaa tctctctttt ctcctgcttg aaggacagac atgactttgg atttccccag   240
gaggagtttg gcaaccagtt ccaaaaggct gaaaccatcc ctgtcctcca tgagatgatc   300
cagcagatct tcaatctctt cagcacaaag gactcatctg ctgcttggga tgagaccctc   360
ctagacaaat tctacactga actctaccag cagctgaatg acctggaagc tgtgtgata   420 caggggtgg gggtgacaga gactcccctg atgaaggagg actccattct ggctgtgagg   480
aaatacttcc aaagaatcac tctctatctg aagagaaga atacagccc ttgtgcctgg   540 gaggttgtca gagcagaaat catgagatct tttctttgt caacaaactt gcaagaaagt   600

```
ttaagaagta aggaacatca ccatcatcac cat        633
```

<210> SEQ ID NO 34
<211> LENGTH: 211
<212> TYPE: PRT
<213> ORGANISM: Artificial Sequence
<220> FEATURE:
<223> OTHER INFORMATION: chemically synthesized

<400> SEQUENCE: 34

```
Gly Gln Ser Gly Gln Thr Asp Val Asp Tyr Tyr Arg Glu Trp Ser Trp
1               5                   10                  15

Thr Gln Val Ser Gly Ser Ser Gly Gly Ser Val His Met Pro Leu Gly
            20                  25                  30

Phe Leu Gly Pro Gly Gly Ser Met Cys Asp Leu Pro Gln Thr His Ser
        35                  40                  45

Leu Gly Ser Arg Arg Thr Leu Met Leu Leu Ala Gln Met Arg Arg Ile
    50                  55                  60

Ser Leu Phe Ser Cys Leu Lys Asp Arg His Asp Phe Gly Phe Pro Gln
65                  70                  75                  80

Glu Glu Phe Gly Asn Gln Phe Gln Lys Ala Glu Thr Ile Pro Val Leu
                85                  90                  95

His Glu Met Ile Gln Gln Ile Phe Asn Leu Phe Ser Thr Lys Asp Ser
            100                 105                 110

Ser Ala Ala Trp Asp Glu Thr Leu Leu Asp Lys Phe Tyr Thr Glu Leu
        115                 120                 125

Tyr Gln Gln Leu Asn Asp Leu Glu Ala Cys Val Ile Gln Gly Val Gly
    130                 135                 140

Val Thr Glu Thr Pro Leu Met Lys Glu Asp Ser Ile Leu Ala Val Arg
145                 150                 155                 160

Lys Tyr Phe Gln Arg Ile Thr Leu Tyr Leu Lys Glu Lys Lys Tyr Ser
                165                 170                 175

Pro Cys Ala Trp Glu Val Val Arg Ala Glu Ile Met Arg Ser Phe Ser
            180                 185                 190

Leu Ser Thr Asn Leu Gln Glu Ser Leu Arg Ser Lys Glu His His His
        195                 200                 205

His His His
    210
```

<210> SEQ ID NO 35
<211> LENGTH: 39
<212> TYPE: DNA
<213> ORGANISM: Artificial Sequence
<220> FEATURE:
<223> OTHER INFORMATION: chemically synthesized

<400> SEQUENCE: 35

```
gtcacgaatt cgcaggacgt cgacgagtgc tcgctgggt        39
```

<210> SEQ ID NO 36
<211> LENGTH: 33
<212> TYPE: DNA
<213> ORGANISM: Artificial Sequence
<220> FEATURE:
<223> OTHER INFORMATION: chemically synthesized

<400> SEQUENCE: 36

```
gctcgcaggg gttggcaccc agcgagcact cgt        33
```

<210> SEQ ID NO 37
<211> LENGTH: 34
<212> TYPE: DNA
<213> ORGANISM: Artificial Sequence
<220> FEATURE:
<223> OTHER INFORMATION: chemically synthesized

<400> SEQUENCE: 37
gccaacccct gcgagcatgc gggcaagtgc atca                              34

<210> SEQ ID NO 38
<211> LENGTH: 35
<212> TYPE: DNA
<213> ORGANISM: Artificial Sequence
<220> FEATURE:
<223> OTHER INFORMATION: chemically synthesized

<400> SEQUENCE: 38
gaaggagccc agcgtgttga tgcacttgcc cgcat                             35

<210> SEQ ID NO 39
<211> LENGTH: 36
<212> TYPE: DNA
<213> ORGANISM: Artificial Sequence
<220> FEATURE:
<223> OTHER INFORMATION: chemically synthesized

<400> SEQUENCE: 39
acacgctggg ctccttcgag tgccagtgtc tgcagg                            36

<210> SEQ ID NO 40
<211> LENGTH: 35
<212> TYPE: DNA
<213> ORGANISM: Artificial Sequence
<220> FEATURE:
<223> OTHER INFORMATION: chemically synthesized

<400> SEQUENCE: 40
cgggggcccg tgtagccctg cagacactgg cactc                             35

<210> SEQ ID NO 41
<211> LENGTH: 36
<212> TYPE: DNA
<213> ORGANISM: Artificial Sequence
<220> FEATURE:
<223> OTHER INFORMATION: chemically synthesized

<400> SEQUENCE: 41
gctacacggg ccccgatgc gagatcgacg tcaacg                             36

<210> SEQ ID NO 42
<211> LENGTH: 38
<212> TYPE: DNA
<213> ORGANISM: Artificial Sequence
<220> FEATURE:
<223> OTHER INFORMATION: chemically synthesized

<400> SEQUENCE: 42
acgggttcga gacgcactcg ttgacgtcga tctcgcat                          38

<210> SEQ ID NO 43
<211> LENGTH: 35
<212> TYPE: DNA
<213> ORGANISM: Artificial Sequence
<220> FEATURE:
<223> OTHER INFORMATION: chemically synthesized

<400> SEQUENCE: 43
agtgcgtctc gaacccgtgc cagaacgacg ccacc                                35

<210> SEQ ID NO 44
<211> LENGTH: 35
<212> TYPE: DNA
<213> ORGANISM: Artificial Sequence
<220> FEATURE:
<223> OTHER INFORMATION: chemically synthesized

<400> SEQUENCE: 44
cccaatctgg tccaggcagg tggcgtcgtt ctggc                                35

<210> SEQ ID NO 45
<211> LENGTH: 40
<212> TYPE: DNA
<213> ORGANISM: Artificial Sequence
<220> FEATURE:
<223> OTHER INFORMATION: chemically synthesized

<400> SEQUENCE: 45
tgcctggacc agattgggga gttccagtgc atctgcatgc                           40

<210> SEQ ID NO 46
<211> LENGTH: 39
<212> TYPE: DNA
<213> ORGANISM: Artificial Sequence
<220> FEATURE:
<223> OTHER INFORMATION: chemically synthesized

<400> SEQUENCE: 46
cacaccctcg tagccgggca tgcagatgca ctggaactc                            39

<210> SEQ ID NO 47
<211> LENGTH: 37
<212> TYPE: DNA
<213> ORGANISM: Artificial Sequence
<220> FEATURE:
<223> OTHER INFORMATION: chemically synthesized

<400> SEQUENCE: 47
ccggctacga gggtgtgcac tgcgaggtca acacaga                              37

<210> SEQ ID NO 48
<211> LENGTH: 37
<212> TYPE: DNA
<213> ORGANISM: Artificial Sequence
<220> FEATURE:
<223> OTHER INFORMATION: chemically synthesized

<400> SEQUENCE: 48
ggctgctggc acactcgtct gtgttgacct cgcagtg                              37

<210> SEQ ID NO 49
<211> LENGTH: 35
<212> TYPE: DNA
<213> ORGANISM: Artificial Sequence
<220> FEATURE:
<223> OTHER INFORMATION: chemically synthesized

<400> SEQUENCE: 49
cgagtgtgcc agcagcccct gcctgcacaa tggcc                                35

<210> SEQ ID NO 50

```
<211> LENGTH: 40
<212> TYPE: DNA
<213> ORGANISM: Artificial Sequence
<220> FEATURE:
<223> OTHER INFORMATION: chemically synthesized

<400> SEQUENCE: 50
tcattgatct tgtccaggca gcggccattg tgcaggcagg                    40

<210> SEQ ID NO 51
<211> LENGTH: 40
<212> TYPE: DNA
<213> ORGANISM: Artificial Sequence
<220> FEATURE:
<223> OTHER INFORMATION: chemically synthesized

<400> SEQUENCE: 51
gctgcctgga caagatcaat gagttccagt gcgagtgccc                    40

<210> SEQ ID NO 52
<211> LENGTH: 35
<212> TYPE: DNA
<213> ORGANISM: Artificial Sequence
<220> FEATURE:
<223> OTHER INFORMATION: chemically synthesized

<400> SEQUENCE: 52
gcccagtgaa gcccgtgggg cactcgcact ggaac                         35

<210> SEQ ID NO 53
<211> LENGTH: 34
<212> TYPE: DNA
<213> ORGANISM: Artificial Sequence
<220> FEATURE:
<223> OTHER INFORMATION: chemically synthesized

<400> SEQUENCE: 53
cacgggcttc actgggcatc tgtgccaggg cagc                          34

<210> SEQ ID NO 54
<211> LENGTH: 36
<212> TYPE: DNA
<213> ORGANISM: Artificial Sequence
<220> FEATURE:
<223> OTHER INFORMATION: chemically synthesized

<400> SEQUENCE: 54
gtcgtctggt ggatccaccg ctgccctggc acagat                        36

<210> SEQ ID NO 55
<211> LENGTH: 20
<212> TYPE: PRT
<213> ORGANISM: Artificial Sequence
<220> FEATURE:
<223> OTHER INFORMATION: chemically synthesized

<400> SEQUENCE: 55

Arg Val Thr Cys Asp Asp Tyr Tyr Tyr Gly Phe Gly Cys Asn Lys Phe
1               5                   10                  15

Gly Arg Pro Ala
            20

<210> SEQ ID NO 56
<211> LENGTH: 15
<212> TYPE: PRT
<213> ORGANISM: Artificial Sequence
```

```
<220> FEATURE:
<223> OTHER INFORMATION: chemically synthesized

<400> SEQUENCE: 56

Phe Pro Leu Asn Thr Phe Asp Leu Val His Glu Leu Leu Ser Arg
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: chemically synthesized

<400> SEQUENCE: 57

Phe Leu Asn Asp Ile His Arg Phe Leu His Trp Thr Asp Leu Met
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: chemically synthesized

<400> SEQUENCE: 58

Pro Tyr Thr Phe Val Glu Gln Val Glu Tyr Trp Leu His Ala Thr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: chemically synthesized

<400> SEQUENCE: 59

Ala Cys Val Ile His Phe Leu Asp Arg Ile Ser Asn Ile Leu Glu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: chemically synthesized

<400> SEQUENCE: 60

Phe Cys Tyr Ile Ala Ala Phe Ser Ala Met Gln Arg Gln Ser Cys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: chemically synthesized

<400> SEQUENCE: 61

Pro Leu Tyr Leu Pro Glu Ile Gly Trp Met Phe Gly Leu Pro Thr
1               5                   10                  15

<210> SEQ ID NO 62
<211> LENGTH: 15
<212> TYPE: PRT
<213> ORGANISM: Artificial Sequence
<220> FEATURE:
```

```
<223> OTHER INFORMATION: chemically synthesized

<400> SEQUENCE: 62

Thr Val Leu Val Ile Pro Asp Leu His Tyr Leu Tyr Val Asp Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: chemically synthesized

<400> SEQUENCE: 63

Phe Ile Asn Asn Val Glu Thr Ala Leu Asp Thr Ile Tyr Asn Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: chemically synthesized

<400> SEQUENCE: 64

Ser Ala Lys His Leu His Pro Gly Arg Leu Pro Pro Met Thr Lys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: chemically synthesized

<400> SEQUENCE: 65

Ala Thr Met Tyr Ala Tyr Leu Glu Arg Leu Glu Ala Ile Leu Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: chemically synthesized

<400> SEQUENCE: 66

Ile Tyr Pro Leu Asp Ala Leu Leu Arg His Leu Asn Ser Leu Cys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: chemically synthesized

<400> SEQUENCE: 67

Cys Phe Pro Thr Val Val Trp Arg Glu Leu Tyr Asn Leu Tyr Gly
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: chemically synthesized
```

```
<400> SEQUENCE: 68

Asn Leu Asp Phe Tyr Leu Asn His Leu Tyr Asn Thr Leu Ala Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: chemically synthesized

<400> SEQUENCE: 69

Asp Phe Ile Asn Ser Met Arg Ser His Leu Gln Ser Ser Asp Gln
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: chemically synthesized

<400> SEQUENCE: 70

Glu Pro Lys Cys Ser Phe Cys Ser Pro Leu Ile Val Pro Ser Pro
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: chemically synthesized

<400> SEQUENCE: 71

Pro Asn Cys Ile Glu Ser Phe Leu Ser Ser Ile His Asp Ser Leu
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: chemically synthesized

<400> SEQUENCE: 72

Thr Asp Asn Ala Leu Phe Leu Glu Thr Val Gln His Tyr Leu Tyr
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: chemically synthesized

<400> SEQUENCE: 73

Cys Tyr Pro Ser Ile Ser Trp Leu Phe Ala Asp Ala Pro Arg Asn
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: chemically synthesized
```

<400> SEQUENCE: 74

Glu Leu Thr Gln Leu Leu Asn Ala Leu Val Asp Val Arg Asn Cys
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: chemically synthesized

<400> SEQUENCE: 75

Leu Leu Ser Ser Phe Val Glu Thr Met Ser Ser Ile Leu Thr Cys
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: chemically synthesized

<400> SEQUENCE: 76

Tyr Leu Leu Arg Leu Pro Ser Leu Glu Glu Leu Trp Gly Pro Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: chemically synthesized

<400> SEQUENCE: 77

Ala Thr Cys Tyr Ile Ile Asn His Trp Val Glu Arg Tyr Ile Ile
1               5                   10                  15

<210> SEQ ID NO 78
<211> LENGTH: 348
<212> TYPE: DNA
<213> ORGANISM: Artificial Sequence
<220> FEATURE:
<223> OTHER INFORMATION: chemically synthesized

<400> SEQUENCE: 78
caggacgtcg acgagtgctc gctgggtgcc aaccctgcg agcatgcggg caagtgcatc      60
aacacgctgg ctccttcga gtgccagtgt ctgcagggct acacgggccc ccgatgcgag     120
atcgacgtca acgagtgcgt ctcgaacccg tgccagaacg acgccacctg cctggaccag     180
attggggagt ccagtgcat ctgcatgccc ggctacgagg gtgtgcactg cgaggtcaac     240
acagacgagt gtgccagcag cccctgcctg cacaatggcc gctgcctgga caagatcaat     300
gagttccagt gcgagtgccc cacgggcttc actgggcatc tgtgccag                  348

<210> SEQ ID NO 79
<211> LENGTH: 116
<212> TYPE: PRT
<213> ORGANISM: Artificial Sequence
<220> FEATURE:
<223> OTHER INFORMATION: chemically synthesized

<400> SEQUENCE: 79

Gln Asp Val Asp Glu Cys Ser Leu Gly Ala Asn Pro Cys Glu His Ala
1               5                   10                  15

```
Gly Lys Cys Ile Asn Thr Leu Gly Ser Phe Glu Cys Gln Cys Leu Gln
            20                  25                  30

Gly Tyr Thr Gly Pro Arg Cys Glu Ile Asp Val Asn Glu Cys Val Ser
        35                  40                  45

Asn Pro Cys Gln Asn Asp Ala Thr Cys Leu Asp Gln Ile Gly Glu Phe
    50                  55                  60

Gln Cys Ile Cys Met Pro Gly Tyr Glu Gly Val His Cys Glu Val Asn
65              70                  75                  80

Thr Asp Glu Cys Ala Ser Ser Pro Cys Leu His Asn Gly Arg Cys Leu
                85                  90                  95

Asp Lys Ile Asn Glu Phe Gln Cys Glu Cys Pro Thr Gly Phe Thr Gly
            100                 105                 110

His Leu Cys Gln
        115
```

<210> SEQ ID NO 80
<211> LENGTH: 516
<212> TYPE: DNA
<213> ORGANISM: Artificial Sequence
<220> FEATURE:
<223> OTHER INFORMATION: chemically synthesized

<400> SEQUENCE: 80

```
cgcgtaactt gtgacgatta ctactacgga ttcgggtgta acaagtttgg tagacccgcc      60
ggcggcggat caggcggagg gtcaggaggc ggtagcggcg ggggctccgg cggcggttca     120
gggggaggat cccaaggacc aatgttcaaa agcctatggg acggaggcca ggacgtcgac     180
gagtgctcgc tgggtgccaa ccctgcgag catgcgggca agtgcatcaa cacgctgggc     240
tccttcgagt gccagtgtct gcagggctac acgggccccc gatgcgagat cgacgtcaac     300
gagtgcgtct cgaacccgtg ccagaacgac gccacctgcc tggaccagat tggggagttc     360
cagtgcatct gcatgcccgg ctacgagggt gtgcactgcg aggtcaacac agacgagtgt     420
gccagcagcc cctgcctgca caatggccgc tgcctggaca gatcaatga gttccagtgc     480
gagtgcccca cgggcttcac tgggcatctg tgccag                              516
```

<210> SEQ ID NO 81
<211> LENGTH: 172
<212> TYPE: PRT
<213> ORGANISM: Artificial Sequence
<220> FEATURE:
<223> OTHER INFORMATION: chemically synthesized

<400> SEQUENCE: 81

```
Arg Val Thr Cys Asp Asp Tyr Tyr Tyr Gly Phe Gly Cys Asn Lys Phe
1               5                   10                  15

Gly Arg Pro Ala Gly Gly Gly Ser Gly Gly Gly Ser Gly Gly Gly Ser
            20                  25                  30

Gly Gly Gly Ser Gly Gly Gly Ser Gly Gly Gly Ser Gln Gly Pro Met
        35                  40                  45

Phe Lys Ser Leu Trp Asp Gly Gly Gln Asp Val Asp Glu Cys Ser Leu
    50                  55                  60

Gly Ala Asn Pro Cys Glu His Ala Gly Lys Cys Ile Asn Thr Leu Gly
65              70                  75                  80

Ser Phe Glu Cys Gln Cys Leu Gln Gly Tyr Thr Gly Pro Arg Cys Glu
                85                  90                  95

Ile Asp Val Asn Glu Cys Val Ser Asn Pro Cys Gln Asn Asp Ala Thr
            100                 105                 110
```

```
Cys Leu Asp Gln Ile Gly Glu Phe Gln Cys Ile Cys Met Pro Gly Tyr
            115                 120                 125

Glu Gly Val His Cys Glu Val Asn Thr Asp Glu Cys Ala Ser Ser Pro
        130                 135                 140

Cys Leu His Asn Gly Arg Cys Leu Asp Lys Ile Asn Glu Phe Gln Cys
145                 150                 155                 160

Glu Cys Pro Thr Gly Phe Thr Gly His Leu Cys Gln
                165                 170
```

<210> SEQ ID NO 82
<211> LENGTH: 516
<212> TYPE: DNA
<213> ORGANISM: Artificial Sequence
<220> FEATURE:
<223> OTHER INFORMATION: chemically synthesized

<400> SEQUENCE: 82

```
cgcgtaactt gtgacgatta ctactacgga ttcgggtgta acaagtttgg tagacccgcc      60
ggcggcggat caggcggagg gtcaggaggc ggtagcggcg ggggctccgg cggcggttca     120
gggggaggat ccgttcatat gcccttgggt ttcctggggc caggaggcca ggacgtcgac     180
gagtgctcgc tgggtgccaa ccctgcgag catgcgggca agtgcatcaa cacgctgggc     240
tccttcgagt gccagtgtct gcagggctac acgggccccc gatgcgagat cgacgtcaac     300
gagtgcgtct cgaacccgtg ccagaacgac gccacctgcc tggaccagat tggggagttc     360
cagtgcatct gcatgcccgg ctacgagggt gtgcactgcg aggtcaacac agacgagtgt     420
gccagcagcc cctgcctgca caatggccgc tgcctggaca gatcaatga gttccagtgc     480
gagtgcccca cgggcttcac tgggcatctg tgccag                              516
```

<210> SEQ ID NO 83
<211> LENGTH: 172
<212> TYPE: PRT
<213> ORGANISM: Artificial Sequence
<220> FEATURE:
<223> OTHER INFORMATION: chemically synthesized

<400> SEQUENCE: 83

```
Arg Val Thr Cys Asp Asp Tyr Tyr Tyr Gly Phe Gly Cys Asn Lys Phe
1               5                   10                  15

Gly Arg Pro Ala Gly Gly Gly Ser Gly Gly Gly Ser Gly Gly Gly Ser
            20                  25                  30

Gly Gly Gly Ser Gly Gly Gly Ser Gly Gly Gly Ser Val His Met Pro
        35                  40                  45

Leu Gly Phe Leu Gly Pro Gly Gly Gln Asp Val Asp Glu Cys Ser Leu
    50                  55                  60

Gly Ala Asn Pro Cys Glu His Ala Gly Lys Cys Ile Asn Thr Leu Gly
65                  70                  75                  80

Ser Phe Glu Cys Gln Cys Leu Gln Gly Tyr Thr Gly Pro Arg Cys Glu
                85                  90                  95

Ile Asp Val Asn Glu Cys Val Ser Asn Pro Cys Gln Asn Asp Ala Thr
            100                 105                 110

Cys Leu Asp Gln Ile Gly Glu Phe Gln Cys Ile Cys Met Pro Gly Tyr
        115                 120                 125

Glu Gly Val His Cys Glu Val Asn Thr Asp Glu Cys Ala Ser Ser Pro
    130                 135                 140

Cys Leu His Asn Gly Arg Cys Leu Asp Lys Ile Asn Glu Phe Gln Cys
```

```
                145                 150                 155                 160
            Glu Cys Pro Thr Gly Phe Thr Gly His Leu Cys Gln
                            165                 170

<210> SEQ ID NO 84
<211> LENGTH: 6
<212> TYPE: PRT
<213> ORGANISM: Artificial Sequence
<220> FEATURE:
<223> OTHER INFORMATION: chemically synthesized

<400> SEQUENCE: 84

His His His His His His
1               5

<210> SEQ ID NO 85
<211> LENGTH: 7
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(7)
<223> OTHER INFORMATION: Ala or Ser

<400> SEQUENCE: 85

Asp Glu Xaa Xaa Xaa Cys Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(7)
<223> OTHER INFORMATION: Ala or Ser

<400> SEQUENCE: 86

Asp Leu Xaa Xaa Xaa Thr Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(6)
<223> OTHER INFORMATION: Ala or Val
<220> FEATURE:
<221> NAME/KEY: MOD_RES
<222> LOCATION: (7)..(7)
<223> OTHER INFORMATION: Any amino acid
```

```
<400> SEQUENCE: 87

Xaa Xaa Gln Ala Arg Xaa Xaa
1               5

<210> SEQ ID NO 88
<211> LENGTH: 5
<212> TYPE: PRT
<213> ORGANISM: Artificial Sequence
<220> FEATURE:
<223> OTHER INFORMATION: chemically synthesized

<400> SEQUENCE: 88

Gly Gln Ser Gly Gln
1               5

<210> SEQ ID NO 89
<211> LENGTH: 6
<212> TYPE: PRT
<213> ORGANISM: Artificial Sequence
<220> FEATURE:
<223> OTHER INFORMATION: chemically synthesized

<400> SEQUENCE: 89

Gly Ser Ser Gly Gly Ser
1               5

<210> SEQ ID NO 90
<211> LENGTH: 3
<212> TYPE: PRT
<213> ORGANISM: Artificial Sequence
<220> FEATURE:
<223> OTHER INFORMATION: chemically synthesized

<400> SEQUENCE: 90

Gly Gly Ser
1

<210> SEQ ID NO 91
<211> LENGTH: 24
<212> TYPE: PRT
<213> ORGANISM: Artificial Sequence
<220> FEATURE:
<223> OTHER INFORMATION: chemically synthesized

<400> SEQUENCE: 91

Gly Gly Gly Ser Gly Gly Gly Ser Gly Gly Ser Gly Gly Gly Ser
1               5                   10                  15

Gly Gly Gly Ser Gly Gly Gly Ser
            20

<210> SEQ ID NO 92
<211> LENGTH: 2
<212> TYPE: PRT
<213> ORGANISM: Artificial Sequence
<220> FEATURE:
<223> OTHER INFORMATION: chemically synthesized

<400> SEQUENCE: 92

Gly Gly
1
```